(12) United States Patent
Shiver et al.

(10) Patent No.: US 7,744,887 B2
(45) Date of Patent: Jun. 29, 2010

(54) HUMAN ANTIBODIES INTERACTING WITH HIV GP41

(75) Inventors: John W. Shiver, Chalfont, PA (US); Michael D. Miller, Chalfont, PA (US); Romas Geleziunas, Doylestown, PA (US); Daria J. Hazuda, Doylestown, PA (US); Peter S. Kim, Bryn Mawr, PA (US); Debra M. Eckert, Salt Lake City, UT (US); Michael J. Root, Boston, MA (US); Simon N. Lennard, Melbourn (GB); Elisabetta Bianchi, Via Sabotino (IT)

(73) Assignees: Merck & Co., Inc., Rahway, NJ (US); Whitehead Insitute of Biomedical Research, Cambridge, MA (US); MedImmune Limited, Cambridge, Cambridgeshire (GB); Istitute di Ricerche di Biologia Molecolare P. Angeletti S.p.A., Pomesia, Rome (IT)

(*) Notice: Subject to any disclaimer, the term of this patent is extended or adjusted under 35 U.S.C. 154(b) by 0 days.

(21) Appl. No.: 11/628,164

(22) PCT Filed: May 31, 2005

(86) PCT No.: PCT/US2005/019049

§ 371 (c)(1),
(2), (4) Date: Nov. 30, 2006

(87) PCT Pub. No.: WO2005/118887

PCT Pub. Date: Dec. 15, 2005

(65) Prior Publication Data

US 2007/0248613 A1    Oct. 25, 2007

Related U.S. Application Data

(60) Provisional application No. 60/576,012, filed on Jun. 1, 2004.

(51) Int. Cl.
- A61K 39/42 (2006.01)
- G01N 33/53 (2006.01)
- A61K 39/395 (2006.01)
- C12P 16/00 (2006.01)

(52) U.S. Cl. .............. 424/148.1; 424/147.1; 424/130.1; 436/512; 530/387.1

(58) Field of Classification Search .................. None
See application file for complete search history.

(56) References Cited

U.S. PATENT DOCUMENTS

| | | |
|---|---|---|
| 5,444,044 A | 8/1995 | Jiang et al. |
| 5,459,060 A | 10/1995 | Cotropia et al. |
| 5,464,933 A | 11/1995 | Bolognesi et al. |
| 5,656,480 A | 8/1997 | Wild et al. |
| 5,731,189 A | 3/1998 | Zolla-Pazner et al. |
| 5,753,503 A | 5/1998 | Katinger et al. |
| 5,777,074 A | 7/1998 | Cotropia et al. |
| 5,831,034 A | 11/1998 | Katinger et al. |
| 6,008,044 A | 12/1999 | Cotropia et al. |
| 6,083,504 A | 7/2000 | Cotropia et al. |
| 6,150,088 A | 11/2000 | Chan et al. |
| 6,506,554 B1 | 1/2003 | Chan et al. |
| 6,596,497 B1 | 7/2003 | Jiang et al. |
| 6,605,427 B2 | 8/2003 | Wild et al. |
| 6,747,126 B1 | 6/2004 | Eckert et al. |
| 6,818,740 B1 | 11/2004 | Eckert et al. |
| 6,841,657 B2 | 1/2005 | Eckert et al. |
| 7,053,179 B2 | 5/2006 | Root et al. |
| 7,402,396 B2 * | 7/2008 | Chan et al. ................... 435/7.1 |
| 2001/0047080 A1 * | 11/2001 | Root et al. .................. 530/350 |
| 2003/0059862 A1 | 3/2003 | Ruben |
| 2003/0118985 A1 | 6/2003 | Hunt et al. |

FOREIGN PATENT DOCUMENTS

EP    0 335 134    3/1989

(Continued)

OTHER PUBLICATIONS

Keller et al. :Passive immunity in prevention and treatment of infectious diseases. Clin Microbiol Rev. Oct. 2000;13(4):602-14.*
Trkola, et al. "Delay of HIV-1 rebound after cessation of antiretroviral therapy through passive transfer of human neutralizing antibodies." Nat Med, 2005, 11(6):615-22.*
Lemckert A. et al "Challenges in the search for an HIV vaccine". Eur J Epidemiol. 2004;19(6):513-6.*
Tamura et al "Structural correlates of an anticarcinoma antibody: identification of specificity-determining residues (SDRs) and development of a minimally immunogenic antibody variant by retention of SDRs only". J Immunol. Feb. 1, 2000;164(3):1432-41.*
Kashmiri et al. "SDR grafting—a new approach to antibody humanization" Methods. May 2005;36(1):25-34.*

(Continued)

Primary Examiner—Bo Peng
(74) Attorney, Agent, or Firm—Henry P. Wu; Sheldon O. Hober

(57) ABSTRACT

Human scFvs are disclosed which interact with a conformational epitope along the pre-hairpin, N-helix coiled coil structure within the heptad repeat 1 (HR1) region of gp41 of HIV. These antibodies, as well as IgG conversions, are shown to neutralize diverse HIV isolates. Isolated nucleic acid molecules are also disclosed which encode relevant portions of these antibodies, as well as the purified forms of the expressed antibodies or relevant antibody fragments, such as $V_H$ and $V_L$ chains. The antibody compositions disclosed within this specification may provide for a therapeutic treatment against HIV infection by reducing viral load levels within an infected individual, thus prolonging the asymptomatic phase of HIV infection. These antibodies will also be useful in assays to identify HIV antiviral compounds as well as allowing for the identification of candidate HIV vaccines, such as HIV peptide vaccines.

11 Claims, 17 Drawing Sheets

FOREIGN PATENT DOCUMENTS

| WO | WO 89/04370    | 5/1989    |
|----|----------------|-----------|
| WO | WO 90/09805    | 9/1990    |
| WO | WO 94/28920    | 12/1994   |
| WO | WO 98/50431    | * 11/1998 |
| WO | WO 00/40616    | 7/2000    |
| WO | WO 01/44286    | 6/2001    |
| WO | WO 03/052122   | 6/2003    |
| WO | WO 2005/118886 | 12/2005   |

OTHER PUBLICATIONS

Jiang, Shibo, et al, Journal of Virological Methods, "A screening assay for antiviral compounds to the HIV-1 gp41 core structure using a conformation-specific monoclonal antibody", vol. 80, pp. 85-96, 1999.

Louis, John M., et al., The Journal of Biological Chemistry, "Design and Properties of $N_{ccg}$-gp41, a chimeric gp41 molecule with nanomolar HIV fusion inhibitory activity", vol. 276, No. 31, pp. 29485-29489, 2001.

Louis, John M., et al., The Journal of Biological Chemistry, "Covalent trimers of the internal N-terminal trimeric coiled-coil of gp41 and antibodies directed against them are potent inhibitors of HIV envelope-mediated cell fusion", vol. 278, No. 22, pp. 20278-20285, 2003.

Caffrey, Michael, et al., EMBO J., "Three-dimensional solution structure of the 44 kDa ectodomain of SIV gp41", vol. 17, No. 16, pp. 4572-4584, 1998.

Chan, David C., et al., Cell, "Core structure of gp41 from the HIV envelope glycoprotein", vol. 89, pp. 263-273, 1997.

Chan, Davide C., et al., Proc. Natl. Acad. Sci, "Evidence that a prominent cavity in the coiled coil of HIV type I gp41 is an attractive drug target", vol. 95, pp. 15613-15617, 1998.

Chan, David C., et al., Cell, "HIV entry and its inhibition", vol. 93, pp. 681-684, 1998.

Dong, Xiao-Nan, et al., Immunology Letters, "N- and C-domains of HIV-1 gp41: Mutation, structure and functions", vol. 75, pp. 215-220, 2001.

Earl, Patricia L., et al., Journal of Virology, "Epitope map of human immunodeficiency virus type 1 gp41 derived from 47 monoclonal antibodies produced by immunization with oligomeric envelope protein", vol. 71, No. 4, pp. 2674-2684, 1997.

Eckert, Debra M., et al., Cell, "Inhibiting HIV-1 entry: Discovery of D-peptide inhibitors that target the gp41 coiled-coil pocket", vol. 99, pp. 103-115, 1999.

Eckert, Debra M., et al., Annu. Rev. Biochem., "Mechanisms of viral membrane fusion and its inhibition", vol. 70, pp. 777-810, 2001.

Eckhart, Leopold, et al., Journal of General Virology, "Immunogenic presentation of a conserved gp41 epitope of human immunodeficiency virus type 1 on recombinant surface antigen of hepatitis B virus", vol. 77, pp. 2001-2008, 1996.

Ferrer, Marc, et al., Nature Structural Biology, "Selection of gp41-mediated HIV-1 cell entry inhibitors from biased combinatorial libraries of non-natural binding elements", vol. 6, No. 10, pp. 953-960, 1999.

Jiang, Shibo, et al, Journal of Virology, "A conformation-specific monoclonal antibody reacting with fusion-active gp41 from the human immunodeficiency virus type 1 envelope glycoprotein", vol. 72, No. 12, pp. 10213-10217, 1998.

Jiang, Shibo, et al., Biochemical and Biophysical Research Communications, "Development of HIV entry inhibitors targeted to the coiled-coil regions of gp41", vol. 269, pp. 641-646, 2000.

Judice, J. Kevin, et al., Proc. Natl. Acad. Sci., "Inhibition of HIV type 1 infectivity by constrained-helical peptides: Implications for the viral fusion mechanism", vol. 94, pp. 13426-13430, 1997.

Malashkevic, Vladimir N., et al.,Proc. Natl. Acad. Sci., "Crystal structure of the simian immunodeficiency virus (SIV) gp41 core: Conserved helical interactions underlie the broad inhibitory activity of gp41 peptides", vol. 95, pp. 9134-9139, 1998.

Vaughn, Tristan J., et al., Nature Biotechnology, "Human antibodies with sub-nanomolar affinities isolated from a large non-immunized phage display library", vol. 14, pp. 309-314, 1996.

Weissenhorn, Winfried, et al., Proc. Natl. Acad. Sci. USA, "Assembly of a rod-shaped chimera of a trimeric GCN4 zipper and the HIV-1 gp41 ectodomain expressed in *Escherichia coli*", vol. 94, pp. 6065-6069, 1997.

Weissenhorn, Winfried, et al., Nature, "Atomic structure of the ectodomain from HIV-1 gp41", vol. 387, pp. 426-429, 1997.

Wild, Carl T., et al., Proc. Natl. Acad. Sci. USA, "Peptides corresponding to a predictive α-helical domain of human immunodeficiency virus type 1 gp41 are potent inhibitors of virus infection", vol. 97, pp. 9770-9774, 1994.

Zwick, Michael B., et al., Journal of Virology, "Broadly neutralizing antibodies targeted to the membrane-proximal external region of human immunodeficiency virus type 1 glycoprotein gp41", vol. 75, No. 22, pp. 10892-10905 2001.

Eckert et al., "Design of potent inhibitors of HIV-1 entry from the gp41 N-peptide region", Proceedings Nat'l Academy of Sciences, vol. 98, No. 20, pp. 11187-11192 (2001).

Golding et al., "Dissection of Human Immunodeficiency Virus Type 1 Entry with Neutralizing Antibodies to gp41 Fusion Intermediates", Journal of Virology, vol. 76, No. 13, pp. 6780-6790 (2002).

Miller et al., "A human monoclonal antibody neutralizes diverse HIV-1 isolates by binding a critical gp4 I epitope", Proceedings Nat'l Academy of Sciences, vol. 102, No. 41, pp. 14759-14764 (2005).

* cited by examiner

A. scFv D5 (nucleotide sequence)
```
CAGGTGCAGC TGGTGCAGTC TGGGGCTGAG GTGAGGAAGC CTGGGGCCTC
AGTGAAGGTC TCCTGCAAGG CTTCTGGAGA CACCTTCAGC AGCTATGCTA
TCAGCTGGGT GCGACAGGCC CCTGGACAAG GCTTGAGTG GATGGGAGGG
ATCATCCCTA TTTTTGGTAC AGCAAACTAC GCACAGAAGT TCCAGGGCAG
AGTCACGATT ACCGCGGACG AATCCACGAG TACAGCCTAC ATGGAGCTGA
GCAGCCTGAG ATCTGAAGAC ACGGCCATTT ATTACTGCGC GAGAGATAAC
CCGACACTAC TCGGCTCTGA CTACTGGGGC AAGGGAACCC TGGTCACCGT
CTCGAGTGGT GGAGGCGGTT CAGGCGGAGG TGGCAGCGGC GGTGGCGGAT
CGGACATCCA GATGACCCAG TCTCCTTCCA CCCTGTCTGC ATCTATTGGA
GACAGAGTCA CCATCACCTG CCGGGCCAGT GAGGGTATTT ATCACTGGTT
GGCCTGGTAT CAGCAGAAGC CAGGGAAAGC CCCTAAACTC CTGATCTATA
AGGCCTCTAG TTAGCCAGT GGGGCCCCAT CAAGGTTCAG CGGCAGTGGA
TCTGGGACAG ATTTCACTCT CACCATCAGC AGCCTGCAGC CTGATGATTT
TGCAACTTAT TACTGCCAAC AATATAGTAA TTATCCGCTC ACTTTCGGCG
GAGGGACCAA GCTGGAGATC AAA (SEQ ID NO:1)
```

B. scFv D5 (amino acid sequence)
```
QVQLVQSGAE VRKPGASVKV SCKASGDTFS SYAISWVRQA PGQGLEWMGG
IIPIFGTANY AQKFQGRVTI TADESTSTAY MELSSLRSED TAIYYCARDN
PTLLGSDYWG KGTLVTVSSG GGSGGGGSG GGGSDIQMTQ SPSTLSASIG
DRVTITCRAS EGIYHWLAWY QQKPGKAPKL LIYKASSLAS GAPSRFSGSG
SGTDFTLTIS SLQPDDFATY YCQQYSNYPL TFGGGTKLEI K (SEQ ID NO:2)
```

C. D5 V$_H$ Coding Region (nucleotide sequence)
```
CAGGTGCAGC TGGTGCAGTC TGGGGCTGAG GTGAGGAAGC CTGGGGCCTC
AGTGAAGGTC TCCTGCAAGG CTTCTGGAGA CACCTTCAGC AGCTATGCTA
TCAGCTGGGT GCGACAGGCC CCTGGACAAG GCTTGAGTG GATGGGAGGG
ATCATCCCTA TTTTTGGTAC AGCAAACTAC GCACAGAAGT TCCAGGGCAG
AGTCACGATT ACCGCGGACG AATCCACGAG TACAGCCTAC ATGGAGCTGA
GCAGCCTGAG ATCTGAAGAC ACGGCCATTT ATTACTGCGC GAGAGATAAC
CCGACACTAC TCGGCTCTGA CTACTGGGGC AAGGGAACCC TGGTCACCGT
CTCGAGT (SEQ ID NO:3, contained within SEQ ID NO:1)
```

D. D5 V$_H$ Coding Region (amino acid sequence)
```
QVQLVQSGAE VRKPGASVKV SCKASGDTFS SYAISWVRQA PGQGLEWMGG
IIPIFGTANY AQKFQGRVTI TADESTSTAY MELSSLRSED TAIYYCARDN
PTLLGSDYWG KGTLVTVSS (SEQ ID NO:4, contained within SEQ ID
NO:2)
```

E. D5 V$_L$ Coding Region (nucleotide sequence)
```
GACATCCAGA TGACCCAGTC TCCTTCCACC CTGTCTGCAT CTATTGGAGA
CAGAGTCACC ATCACCTGCC GGGCCAGTGA GGGTATTTAT CACTGGTTGG
CCTGGTATCA GCAGAAGCCA GGGAAAGCCC CTAAACTCCT GATCTATAAG
GCCTCTAGTT TAGCCAGTGG GGCCCCATCA AGGTTCAGCG GCAGTGGATC
TGGGACAGAT TCACTCTCA CCATCAGCAG CCTGCAGCCT GATGATTTTG
CAACTTATTA CTGCCAACAA TATAGTAATT ATCCGCTCAC TTTCGGCGGA
GGGACCAAGC TGGAGATCAA A (SEQ ID NO:5, contained within SEQ ID
NO:1)
```

F. D5 V$_L$ Coding Region (amino acid sequence)
```
DIQMTQSPST LSASIGDRVT ITCRASEGIY HWLAWYQQKP GKAPKLLIYK
ASSLASGAPS RFSGSGSGTD FTLTISSLQP DDFATYYCQQ YSNYPLTFGG
GTKLEIK (SEQ ID NO:6, contained within SEQ ID NO:2)
```

Fig. 2A-F

A. scFv B11 (nucleotide sequence)
CAGGTGCAGC TGGTGCAATC TGGGGCTGAG GTGAAGAAGC CTGGGTCCTC
GGTGAAGGTC TCCTGCAAGG CTTCTGGAGG CACCTTCAGC AGCTATGCTA
TCAGCTGGGT GCGACAGGCC CCTGGACAAG GGCTTGAGTG GATGGGAGGG
ATCATCCCTC TCTTTGATAC ATCAAACTAC GCACAGAACT TCCAGGGCAG
AATCACGATA ACTGCGGACA AATCCACGAG TACAGCCTAC ATGGAACTGA
GCAGCCTGAG ATTTGAGGAC ACGGCCATTT ATTACTGTGC GAGAGATAAC
CCTTTACTTC TCGCTATGGA TGTCTGGGGG AAAGGGACCA CGGTCACCGT
CTCGAGTGGT GGAGGCGGTT CAGGCGGAGG TGGCAGCGGC GGTGGCGGAT
CGGACATCCA GATGACCCAG TCTCCTTCCA CCCTGTCTGC ATCTATTGGA
GACAGAGTCA CCATCACCTG CCGGGCCAGT GAGGGTATTT ATCACTGGTT
GGCCTGGTAT CAGCAGAAGC CAGGGAAAGC CCCTAAACTC CTGATCTATA
AGGCCTCTAG TTTAGCCAGT GGGGCCCCAT CAAGGTTCAG CGGCAGTGGA
TCTGGGACAG ATTTCACTCT CACCATCAGC AGCCTGCAGC CTGATGATTT
TGCAACTTAT TACTGCCAAC AATATAGTAA TTATCCGCTC ACTTTCGGCG
GAGGGACCAA GCTGGAGATC AAA (SEQ ID NO:7)

B. scFv B11 (amino acid sequence)
QVQLVQSGAE VKKPGSSVKV SCKASGGTFS SYAISWVRQA PGQGLEWMGG
IIPLFDTSNY AQNFQGRITI TADKSTSTAY MELSSLRFED TAIYYCARDN
PLLLAMDVWG KGTTVTVSSG GGGSGGGGSG GGGSDIQMTQ SPSTLSASIG
DRVTITCRAS EGIYHWLAWY QQKPGKAPKL LIYKASSLAS GAPSRFSGSG
SGTDFTLTIS SLQPDDFATY YCQQYSNYPL TFGGGTKLEI K (SEQ ID NO:8)

C. B11 V$_H$ Coding Region (nucleotide sequence)
CAGGTGCAGC TGGTGCAATC TGGGGCTGAG GTGAAGAAGC CTGGGTCCTC
GGTGAAGGTC TCCTGCAAGG CTTCTGGAGG CACCTTCAGC AGCTATGCTA
TCAGCTGGGT GCGACAGGCC CCTGGACAAG GGCTTGAGTG GATGGGAGGG
ATCATCCCTC TCTTTGATAC ATCAAACTAC GCACAGAACT TCCAGGGCAG
AATCACGATA ACTGCGGACA AATCCACGAG TACAGCCTAC ATGGAACTGA
GCAGCCTGAG ATTTGAGGAC ACGGCCATTT ATTACTGTGC GAGAGATAAC
CCTTTACTTC TCGCTATGGA TGTCTGGGGG AAAGGGACCA CGGTCACCGT
CTCGAGT (SEQ ID NO:9, contained within SEQ ID NO:7)

D. B11 V$_H$ Coding Region (amino acid sequence)
QVQLVQSGAE VKKPGSSVKV SCKASGGTFS SYAISWVRQA PGQGLEWMGG
IIPLFDTSNY AQNFQGRITI TADKSTSTAY MELSSLRFED TAIYYCARDN
PLLLAMDVWG KGTTVTVSS (SEQ ID NO:10, contained within SEQ ID NO:8)

E. B11 V$_L$ Coding Region (nucleotide sequence)
GACATCCAGA TGACCCAGTC TCCTTCCACC CTGTCTGCAT CTATTGGAGA
CAGAGTCACC ATCACCTGCC GGGCCAGTGA GGGTATTTAT CACTGGTTGG
CCTGGTATCA GCAGAAGCCA GGGAAAGCCC CTAAACTCCT GATCTATAAG
GCCTCTAGTT TAGCCAGTGG GGCCCCATCA AGGTTCAGCG GCAGTGGATC
TGGGACAGAT TTCACTCTCA CCATCAGCAG CCTGCAGCCT GATGATTTTG
CAACTTATTA CTGCCAACAA TATAGTAATT ATCCGCTCAC TTTCGGCGGA
GGGACCAAGC TGGAGATCAA A (SEQ ID NO:11, contained within SEQ ID NO:7)

F. B11 V$_L$ Coding Region (amino acid sequence)
DIQMTQSPST LSASIGDRVT ITCRASEGIY HWLAWYQQKP GKAPKLLIYK
ASSLASGAPS RFSGSGSGTD FTLTISSLQP DDFATYYCQQ YSNYPLTFGG
GTKLEIK (SEQ ID NO:12, contained within SEQ ID NO:8)

Fig. 3A-F

```
                                    V_H
       [       V_H FW1           ][CDR1][    V_H FW2      ]
D5     QVQLVQSGAEVRKPGASVKVSCKASGDTFS SYAIS WVRQAPGQGLEWMG
B11    QVQLVQSGAEVKKPGSSVKVSCKASGGTFS SYAIS WVRQAPGQGLEWMG
       **********:***.**********.*** ***** **************

[   V_H CDR2      ] [      V_H FW3              ]
D5     GIIPIFGTANYAQKFQG RVTITADESTSTAYMELSSLRSEDTAIYYCAR
B11    GIIPLFDTSNYAQNFQG RITITADKSTSTAYMELSSLRFEDTAIYYCAR
       ****:*.*:****.*** *:*****:************ **********

[ V_H CDR3 ][   V_H FW4   ][(G_4S)_3 Linker   ]
D5     DNPTLLGSDY WGKGTLVTVSS GGGGSGGGGSGGGGS
B11    DNPLLLAMDV WGKGTTVTVSS GGGGSGGGGSGGGGS
       ***.**. * ***** ***** ***************

[        V_L FW1           ][ V_L CDR1 ] [   V_L FW2    ]
D5     DIQMTQSPSTLSASIGDRVTITC RASEGIYHWLA WYQQKPGKAPKLLIY
B11    DIQMTQSPSTLSASIGDRVTITC RASEGIYHWLA WYQQKPGKAPKLLIY
       ********************** *********** ***************

V_L
       [ CDR2] [       V_L FW3               ][VL CDR3 ]
D5     KASSLAS GAPSRFSGSGSGTDFTLTISSLQPDDFATYYC QQYSNYPLT
B11    KASSLAS GAPSRFSGSGSGTDFTLTISSLQPDDFATYYC QQYSNYPLT
       ******* ****************************** *********

[ V_L FW4 ]
D5     FGGGTKLEIK (SEQ ID NO:2)
B11    FGGGTKLEIK (SEQ ID NO:8)
       **********
```

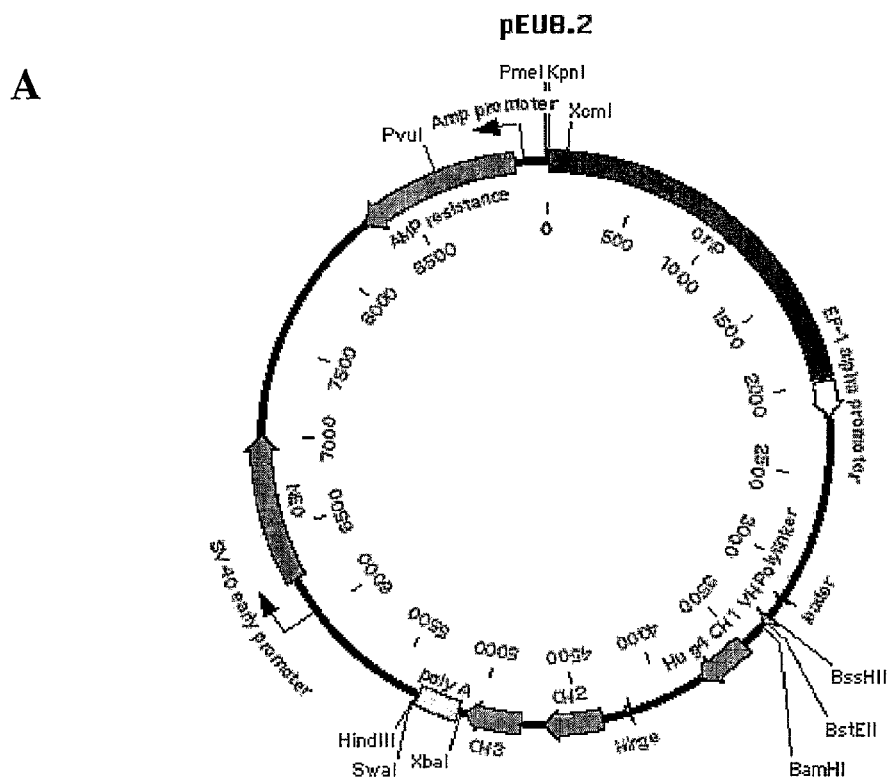

B

```
              BssH II
5'-   CTCTCCACAG GCGCGCACTC CCAGGTGCAG CTGGTGCAGT CTGGGGCTGA GGTGAGGAAG
      CCTGGGGCCT CAGTGAAGGT CTCCTGCAAG GCTTCTGGAG ACACCTTCAG CAGCTATGCT
      ATCAGCTGGG TGCGACAGGC CCCTGGACAA GGGCTTGAGT GGATGGGAGG GATCATCCCT
      ATTTTTGGTA CAGCAAACTA CGCACAGAAG TTCCAGGGCA GAGTCACGAT TACCGCGGAC
      GAATCCACGA GTACAGCCTA CATGGAGCTG AGCAGCCTGA GATCTGAAGA CACGGCCATT
      TATTACTGCG CGAGAGATAA CCCGACACTA CTCGGCTCTG ACTACTGGGG CAAGGGAACC
      CTGGTCACCG TCTCCTCAGG TGGAGTCCTG TCGA (SEQ ID NO:19)
      BstE II
```

Fig. 5A-B

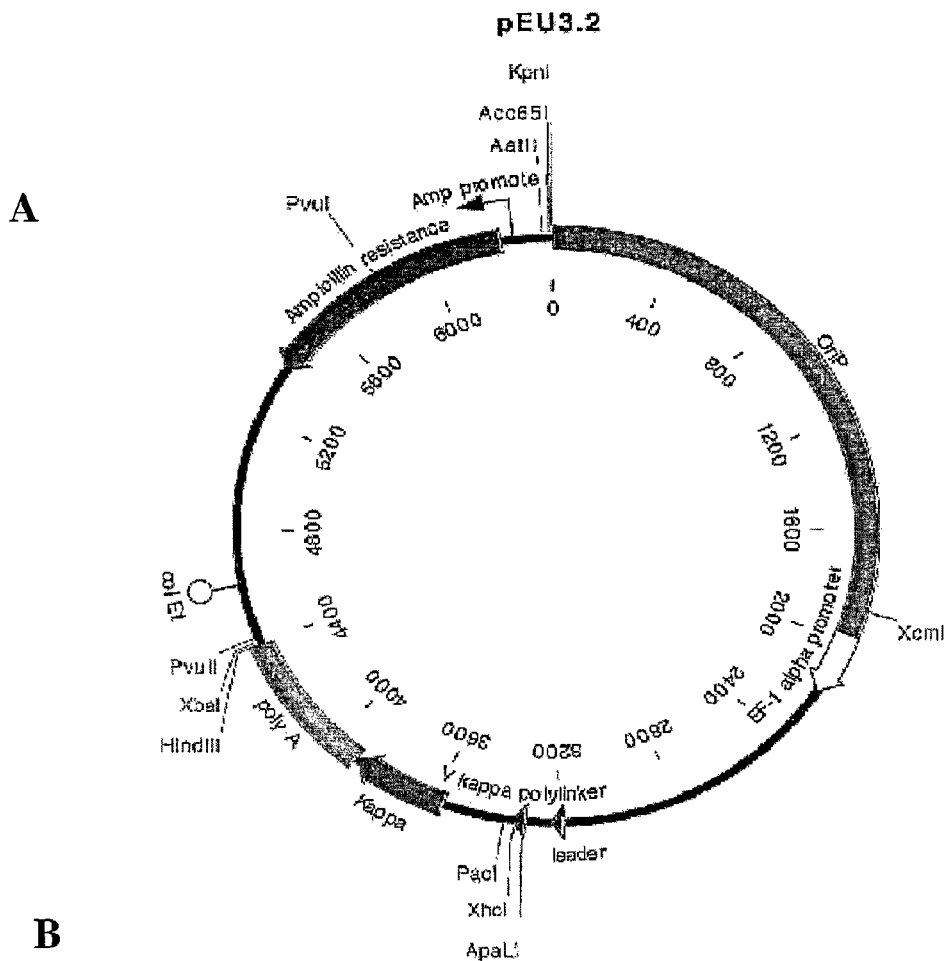

```
              ApaL I
5'-GATCGATGGT  GTGCACTCGG  ACATCCAGAT  GACCCAGTCT  CCTTCCACCC  TGTCTGCATC
   TATTGGAGAC  AGAGTCACCA  TCACCTGCCG  GGCCAGTGAG  GGTATTTATC  ACTGGTTGGC
   CTGGTATCAG  CAGAAGCCAG  GGAAAGCCCC  TAAACTCCTG  ATCTATAAGG  CCTCTAGTTT
   AGCCAGTGGG  GCCCCATCAA  GGTTCAGCGG  CAGTGGATCT  GGGACAGATT  TCACTCTCAC
   CATCAGCAGC  CTGCAGCCTG  ATGATTTTGC  AACTTATTAC  TGCCAACAAT  ATAGTAATTA
   TCCGCTCACT  TTCGGCGGAG  GGACCAAGCT  GGAGATCAAA  CGTGAGTAGA  ATAGATCTAA
   CTTAATT AAGGAATAG (SEQ ID NO:20)
   Pac I
```

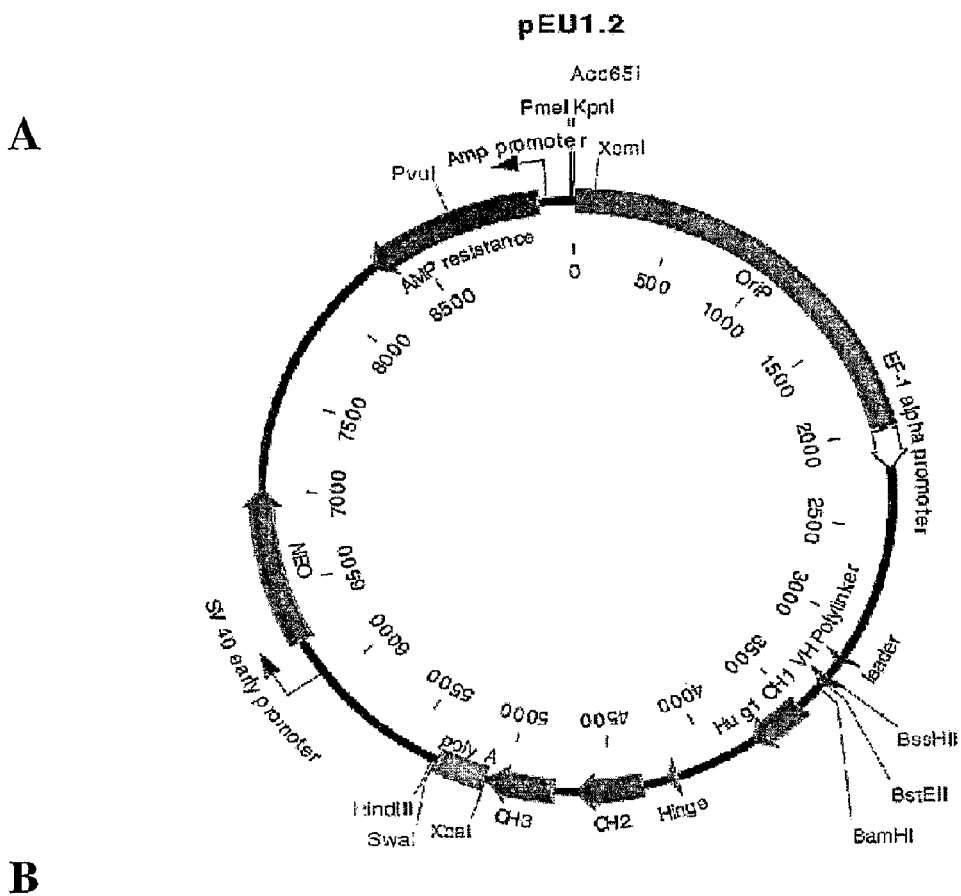

pEU1.2

B

```
          BssH II
5'-CTCTCCACAG GCGCGCACTC CCAGGTGCAG CTGGTGCAAT CTGGGGCTGA GGTGAAGAAG
   CCTGGGTCCT CGGTGAAGGT CTCCTGCAAG GCTTCTGGAG GCACCTTCAG CAGCTATGCT
   ATCAGCTGGG TGCGACAGGC CCCTGGACAA GGGCTTGAGT GGATGGGAGG GATCATCCCT
   CTCTTTGATA CATCAAACTA CGCACAGAAC TTCCAGGGCA GAATCACGAT AACTGCGGAC
   AAATCCACGA GTACAGCCTA CATGGAACTG AGCAGCCTGA GATTTGAGGA CACGGCCATT
   TATTACTGTG CGAGAGATAA CCCTTTACTT CTCGCTATGG ATGTCTGGGG GAAAGGGACC
   ACGGTCACCG TCTCGAGTGG TGGAGGCGGT TCAGGCGGAG GTGGCTCTGG CGGT-3'
     BstE II                                                (SEQ ID NO:26)
```

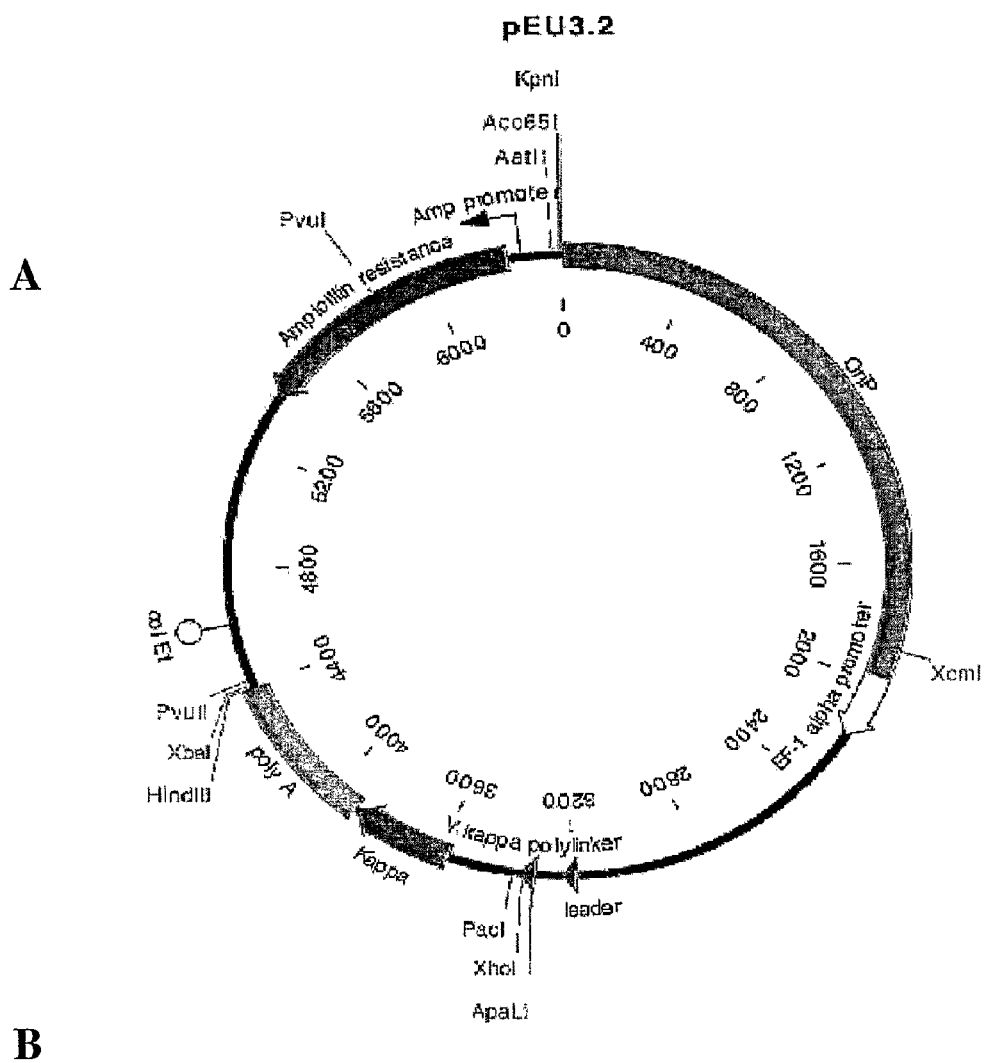

B

```
         ApaL I
5'-GATCGATGGT GTGCACTCGG ACATCCAGAT GACCCAGTCT CCTTCCACCC TGTCTGCATC
   TATTGGAGAC AGAGTCACCA TCACCTGCCG GGCCAGTGAG GGTATTTATC ACTGGTTGGC
   CTGGTATCAG CAGAAGCCAG GGAAAGCCCC TAAACTCCTG ATCTATAAGG CCTCTAGTTT
   AGCCAGTGGG GCCCCATCAA GGTTCAGCGG CAGTGGATCT GGGACAGATT TCACTCTCAC
   CATCAGCAGC CTGCAGCCTG ATGATTTTGC AACTTATTAC TGCCAACAAT ATAGTAATTA
   TCCGCTCACT TTCGGCGGAG GGACCAAGCT GGAGATCAAA CGTGAGTAGA ATAGATCTAA
   CTTAATTAAG GAATAG (SEQ ID NO:27)
    Pac I
```

Fig. 8A-B

A
B
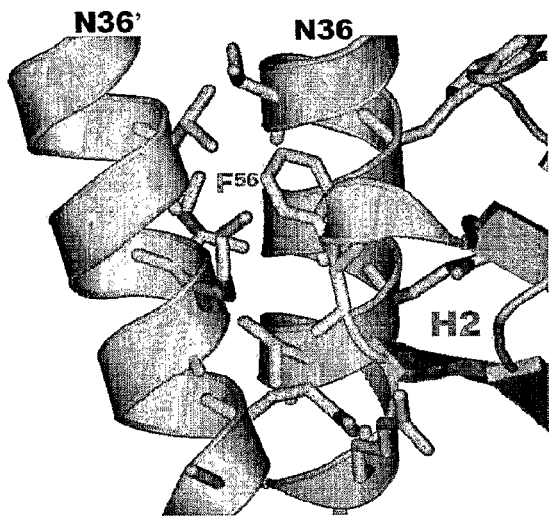
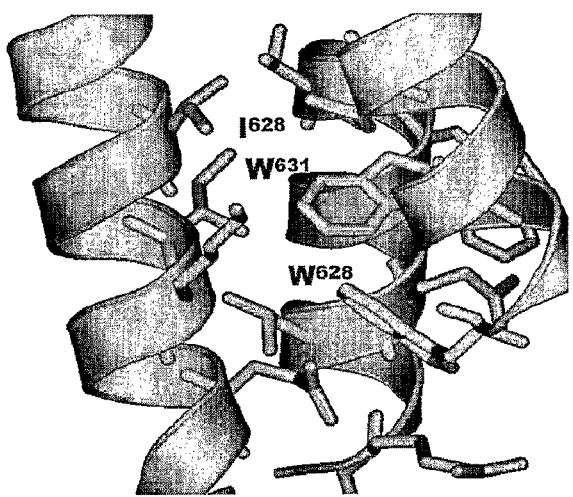
Fig. 16

US 7,744,887 B2

HUMAN ANTIBODIES INTERACTING WITH HIV GP41

CROSS-REFERENCE TO RELATED APPLICATIONS

The present application is the §371 National Stage application of PCT International Application serial no. PCT/US2005/019049, having an international filing date of May 31, 2005, which claims priority to U.S. Provisional Application Ser. No. 60/576,012, filed Jun. 1, 2004.

STATEMENT REGARDING FEDERALLY-SPONSORED R&D

Not Applicable

REFERENCE TO MICROFICHE APPENDIX

Not Applicable

FIELD OF THE INVENTION

The present invention relates to a human immunodeficiency virus (HIV) neutralizing antibody that interacts with a conformational epitope along adjacent coils of a trimeric pre-hairpin, N-helix coiled coil structure within the heptad repeat 1 (HR1) region of gp41. Multiple forms of these isolated antibodies are disclosed and exemplified. Isolated nucleic acid molecules expressing relevant portions of these antibodies, as well as the purified forms of the expressed antibodies or relevant fragments thereof are also within the scope of the present invention. The present disclosure presents methods of selecting for neutralizing antibodies against fusion intermediate mimetics, such as the hydrophobic pocket region of gp41. The disclosure of the antibodies of the present invention also provide methods of identifying HIV antiviral compounds. These antibodies may be utilized in conjunction with one or more mimetics of the hydrophobic pocket within the heptad repeat 1 (HR1) region of the gp41 ectodomain to screen and select for test compounds as an HIV antiviral as well as allowing for the identification of candidate HIV vaccines, such as HIV peptide vaccines. The antibody compositions of the present invention may provide for a therapeutic treatment against HIV infection by reducing viral load levels within an infected individual, thus prolonging the asymptomatic phase of HIV infection.

BACKGROUND OF TEE INVENTION

Human Immunodeficiency Virus (HIV) is the etiological agent of acquired human immune deficiency syndrome (AIDS) and related disorders. HIV-1/HIV-2 are RNA viruses of the Retroviridae family and exhibits the 5' LTR-gag-pol-env-LTR 3' organization of all retroviruses. The integrated form of HIV, known as the provirus, is approximately 9.8 Kb in length. Each end of the viral genome contains flanking sequences known as long terminal repeats (LTRs). The HIV genes encode at least nine proteins and are divided into three classes; the major structural proteins (Gag, Pol, and Env), the regulatory proteins (Tat and Rev); and the accessory proteins (Vpu, Vpr, Vif and Nef).

The env gene encodes the viral envelope glycoprotein that is translated as a 160-kilodalton (kDa) precursor (gp160) and then cleaved by a cellular protease to yield the external 120-kDa envelope glycoprotein (gp120) and the transmembrane 41-kDa envelope glycoprotein (gp41). Gp120 and gp41 remain associated and are displayed on the viral particles and the surface of HIV-infected cells. Gp120 binds to the CD4/chemokine receptor present on the surface of helper T-lymphocytes, macrophages and other target cells in addition to other co-receptor molecules. X4 (macrophage tropic) virus show tropism for CD4/CXCR4 complexes while a R5 (T-cell line tropic) virus interacts with a CD4/CCR5 receptor complex. After gp120 binds to CD4, gp41 mediates the fusion event responsible for virus entry. The virus fuses with and enters the target cell, followed by reverse transcription of its single stranded RNA genome into the double-stranded DNA via a RNA dependent DNA polymerase. The viral DNA, known as provirus, enters the cell nucleus, where the viral DNA directs the production of new viral RNA within the nucleus, expression of early and late HIV viral proteins, and subsequently the production and cellular release of new virus particles.

Gp41-mediated fusion is a complex process involving three essential components located in the ectodomain of the glycoprotein: an $NH_2$-terminal fusion peptide, an $NH_2$-terminal heptad repeat ("N-helix") and a COOH-terminal heptad repeat ("C-helix"). The two heptad repeat regions ($NH_2$:HR1; COOH: HR2) impart periodic hydrophobicity to the glycoprotein and are predictive of alpha-helical structures that interact with each other to form a fusogenic (i.e., fusion-active) conformation of gp41 called the "trimer-of hairpins," a common structural motif involved in the fusion mechanism of many enveloped viruses. The trimer-of-hairpins structure is a bundle of six α-helices: three α-helices (formed by C-helix regions from three gp41 ectodomains) packed in an anti-parallel manner against a central, three-stranded coiled-coil (formed by N-helix regions from three gp41 ectodomains). The fusion process progresses via the formation of a "pre-hairpin" conformation of gp41 that places the $NH_2$-terminal fusion peptide near/in the target cell membrane, exposing the N-helix coiled-coil. The trimer-of-hairpins forms when three C-helices fold back to associate with the central, N-helix coiled-coil, drawing the viral and host cell membranes into close contact as a prelude to membrane fusion.

Effective treatment regimens for HIV infected individuals have become available recently. However, these drugs will not have a significant impact on the disease in many parts of the world and they will have a minimal impact in halting the spread of infection within the human population. One additional arm to add to the treatment arsenal would be an antibody that acts as an anti-viral agent for the treatment of HIV-associated disease. To the best of the inventors knowledge, there is currently no known isolated anti-viral antibody targeting the gp41 HR1 pre-hairpin with the ability to block HIV infection. It would also be advantageous to select for additional HIV antiviral agents and/or peptide vaccines for use in treating HIV infected individuals. Selection of an antibody targeting this region would allow for high throughput screening assays which would be useful in selecting new HIV antiviral agents.

U.S. Pat. No. 5,459,060 (issued 17 Oct. 1995), U.S. Pat. No. 6,008,044 (issued 28 Dec. 1999) and U.S. Pat. No. 6,983,504 (issued 4 Jul. 2000), each to J. P. Cotropia, disclose a human monoclonal antibody that interacts with the region around amino acids 602-611 of gp41.

U.S. Pat. No. 5,731,189 (issued 24 Mar. 1998 to Zolla-Pazuer and Gorny) discloses a series of gp41 specific human monoclonal antibodies that interact somewhere within a region from amino acids 579-663, depending upon the antibody.

U.S. Pat. Nos. 5,753,503 (issued 19 May 1998) and 5,831,034 (3 Nov. 1998), each to H. W. D. Katinger, disclose a series of human monoclonal antibodies raised against gp41. The '034 patent discloses hybridomas which produce 2F5 and 4E10 antibodies, which interact with epitopes downstream of the C-Heptad repeat of gp41.

U.S. Patent Application Publication US 2003/0118985 (published 26 Jun. 2003 in the name of Hunt et al.) discloses a human monoclonal antibody that interacts with the region around amino acids 649-672.

Louis et al. (2003, *J. Biol. Chem.* 278(22): 20278-20285) suggest that a fraction of a polyclonal sera raised against a covalent trimer of the gp41 trimeric coiled-coil region inhibits HIV envelope mediated cell fusion in vitro.

It would be of great import in the battle against AIDS to produce a therapeutic-based HIV anti-viral antibody targeting gp41 that possesses the ability to therapeutically reduce viral load levels within an infected individual, thus prolonging the asymptomatic phase of HIV infection. The present invention addresses and meets this needs by disclosing a class of neutralizing anti-HIV antibodies which interact with the HR1 region of the pre-hairpin, pre-fusion gp41 intermediate, and associated screening assays.

SUMMARY OF THE INVENTION

The present invention relates to a HIV neutralizing antibody that interacts with a conformational epitope within a groove of adjacent coils of a trimeric N-peptide pre-hairpin intermediate structure of the heptad repeat 1 (HR1) region of the ectodomain of the HIV transmembrane glycoprotein gp41.

The present invention further relates to a HIV neutralizing antibody that interacts with a conformational epitope within the trimeric N-peptide pre-hairpin coiled coil intermediate structure of the HR1 region of the ectodomain of the HIV transmembrane glycoprotein gp41, wherein the gp41 epitope for the neutralizing antibody comprises at least one of the following gp41 amino acid residues contributed by one or the other of adjacent coils within the trimeric HR1-based structure: Leu565, Gln567, Leu568, Thr569, Val570, Trp571, Gly572, Lys574, Gln575, Gln577, Ala578, Arg579, and Leu581.

The present invention further relates to a HIV neutralizing antibody that interacts with a conformational epitope within a groove of a trimeric N-peptide pre-fusion intermediate structure of the HR1 region of the ectodomain of the HIV transmembrane glycoprotein gp41, wherein the gp41 epitope for the neutralizing antibody comprises at least one of the following gp41 amino acid residues contributed by one or the other of adjacent coils within the trimeric HR1-based structure: Leu568, Thr569, Val570, Trp571, Gly572, and Lys574.

The present invention also relates to a HIV neutralizing antibody that interacts with a hydrophobic pocket within a groove of the gp41 trimeric HR1 pre-fusion intermediate, wherein the gp41 epitope within this hydrophobic pocket for the neutralizing antibody comprises at least one of the following gp41 amino acid residues contributed by one or the other of adjacent coils within the trimeric HR1-based structure: Leu568, Val570, Trp571, and Lys574, with Gly572 contributing a spatial integrity to this region of the pre-fusion trimer.

The present invention also relates to a HIV neutralizing antibody that interacts with a hydrophobic pocket within a groove of the gp41 trimeric HR1 pre-fusion intermediate, wherein the gp41 epitope within this hydrophobic pocket for the neutralizing antibody comprises the following gp41 amino acid residues contributed by one or the other of adjacent coils within the trimeric HR1-based structure: Leu568, Val570, Trp571, and Lys574, with Gly572 contributing a spatial integrity to this region of the pre-fusion trimer structure.

To this end, the present invention relates to any form of a HIV neutralizing antibody that possesses at least substantially as effective gp41 epitope binding and virus neutralizing characteristics as the D5 and B11 antibodies exemplified herein, including but not limited to affinity matured versions of these exemplified antibodies.

The present invention further relates to an antibody which comprises at least one CDR region from either the variable light and/or heavy chain from D5, B11, or an affinity matured form of either.

The present invention also relates to the HIV neutralizing human antibody D5, and any affinity matured form of D5.

The present invention also relates to the HIV neutralizing human antibody B11, and any affinity matured form of B11.

The present invention provides for several methodologies which may allow for identification of a HIV neutralizing antibody from a source other than an individual infected with HIV. It is disclosed herein the ability to use a synthetic antigen(s) to isolate a HIV neutralizing antibody. Therefore, both the products and the associated methodology of the present invention may allow for additional strategies regarding the development of an HIV vaccine, including but not necessarily limited to a method of identifying a neutralizing antibody; a method for identifying an HIV vaccine candidate(s) (including but not limited to small molecule inhibitors of viral membrane fusion and/or peptide vaccines). As an example, but not a limitation, the present invention further contemplates the use of D5- or B11-like antibodies in an antibody/peptide interaction assay involving a D5- or B11-like antibody and at least one HR1 hydrophobic pocket-containing peptide mimetic.

The present invention also relates to a therapeutic method for treating a HIV positive subject comprising the administration to the subject a composition which comprises a D5/B11-like antibody, and optionally one or more carriers, one or more excipients, and/or one or more chemical derivatives. Administration of such a composition will be of therapeutic value by leading to a reduction in viral load and thus prolonging the asymptomatic phase of the disease. To this end, the present invention also relates further to a method of blocking fusion of the human immunodeficiency virus to human cells and a method of preventing infection of human cells by HIV which comprises contacting HIV with an effective amount of a D5/B11-like antibody composition, such that the composition effectively blocks formation of the 6-helical, pre-fusion gp41 structure which normally promotes fusion of the virus with the host cell.

The present invention further relates to the isolation and characterization of a HIV neutralizing antibody selected from a source other than an individual infected with HIV, including but not limited to an antibody interacting with a conformational epitope within a groove of adjacent coils of the trimeric N-peptide pre-hairpin intermediate HR1 structure from gp41. This specification represents a disclosure of the ability to use an antigen to isolate a neutralizing antibody, an antibody which possesses multiple utilities disclosed herein, including but not limited to methodology surrounding the development of an efficacious HIV vaccine with either prophylactic or therapeutic properties. Such methodology includes but is not limited to identifying additional broad spectrum HIV antibodies, methods of identifying HIV vaccine candidates, as well as methods associated with prophylactic or therapeutic HIV vaccination regimes. Therefore, the neutralizing antibodies of the present invention have potential at least for the following uses: (1) as a prophylactic or therapeutic agent to directly prevent or reduce infection or treat HIV infected individuals, either alone or in conjunction with any combination therapy that may provide for a suppression of viral replication and, hence, reduce viral load within an infected individual; (2) in designing peptide immunogens that may be used to elicit neutralizing antibody responses in prophylactic or therapeutic vaccination strategies, resulting in either a lower transmission rate to previously uninfected individuals and/or a reduction in the levels of the viral loads within an infected individual, so as to prolong the asymptomatic phase of HIV-1 infection; (3) in an antibody/peptide interaction assay involving the D5- or B11-like antibody and various HR1 hydrophobic pocket-containing peptides; (4) to generate a prophylactic or therapeutic anti-idiotypic antibody (Ab2) mimicking the cryptic epitope(s) that bind the neutralizing antibodies of the present invention; and, (5) in designing peptides derived from the complementarity determining regions (CDRs) of the neutralizing antibodies of the present invention for use in either screening inhibitors of HIV or for use in prophylactic and/or therapeutic regimes. These CDR-derived peptides, and improved derivatives thereof, can be used as therapeutics to treat HIV-infected individuals or, by conjugation to a carrier protein, to generate antibodies with similar specificity and function as the anti-idiotypic Ab2 antibodies described above. Specific knowledge of this antigen-antibody interaction described throughout this specification will allow for design of a peptide immunogen comprising this region to the exclusion of portion of the N-peptide which would induce the formation in vivo of non-neutralizing antibodies. Such peptides may contain mutations at residues which do not bind D5 or may be 'trimmed' to delete 'non-D5' binding regions in order to reduce generation of non-neutralizing antibodies. Putative new designed molecules may be validated as immunogens by screening for binding to the broadly neutralizing HIV antibodies disclosed herein. The binders with the highest affinity are candidates as a peptide eliciting a relevant D5/B11 immune response and for representing a faithful mimetic of gp41 N-region hydrophobic pocket in the fusion intermediate. Additionally, gp41 HR1 peptide mimetics may be identified by panning a D5/B11 antibody or relevant derivative against a library generated from various known enrichment technologies, including but not limited to a phage-display peptide library (e.g., a knottin or similar rock-type library to obtain a mimetic peptide within a scaffold that delimits its flexibility). This peptide might serve either as an immunogen as part of a conjugate, or as anti-viral drags themselves, including but not limited to a naked form, a form conjugated to PEG, or a form incorporated in carrier, such as recombinantly inserting this peptide mimetic into a carrier protein such as HepB core (into one of the loops) or similar such virion-based carrier systems (e.g., HIV).

It is an object of the present invention to provide for antibodies that neutralize HIV, and in effect combat a HIV infection by reducing viral load levels within an infected individual and thus leading to prolonging the asymptomatic phase of HIV infection. These neutralizing antibodies recognize a conformational epitope formed from adjacent coiled structures of a trimeric pre-fusion intermediate within the HR1 region of the ectodomain of the HIV transmembrane glycoprotein gp41.

It is a further object of the present invention to provide for HIV neutralizing antibodies that interact with a conformational epitope within a groove of a trimeric N-peptide pre-hairpin intermediate structure of the heptad repeat (HR1) region of the ectodomain of the HIV transmembrane glycoprotein gp41, wherein the gp41 epitope for the neutralizing antibody comprises at least one of the following gp41 amino acid residues contributed by one or the other adjoining coils from two of the three gp41 HR1 regions: Leu565, Gln567, Leu568, Thr569, Val570, Trp571, Gly572, Lys574, Gln575, Gln577, Ala578, Arg579, and Leu581, and especially at least one of amino acid residues Leu568, Thr569, Val570, Trp571, Gly572, and Lys574.

It is also an object of the present invention to provide for a HIV neutralizing antibody that possesses at least substantially as effective gp41 epitope binding and virus neutralizing characteristics as antibodies D5, B11 or affinity matured versions thereof, including but not limited to a commercially viable form such as the IgG class, a murine monoclonal, a murine-human chimeric antibody, a humanized antibody and/or a human antibody sourced from either a humanized transgenic mouse or an antibody or antibody fragment initially selected from libraries utilizing enrichment technologies, including but not limited to an antibody identified through phage display technology, as exemplified herein.

An object of the present invention is to provide the HIV neutralizing human antibody D5 and/or B11, and affinity matured forms thereof.

Another object of the present invention provides for assays utilizing the D5/B11 antibodies of the present invention in antibody/peptide/test compound interaction assays to select antiviral compounds, such as small molecule inhibitors of viral fusion and/or peptides which will promote a neutralizing response upon host administration.

The term "trimeric" as used in conjunction with the gp41 N-heptad pre-fusion intermediate, may be used interchangeably with terms such as "N-helices" or "gp41 N-peptide hairpins" or "N-helix coiled coil", "N-terminal heptad repeat", and like phrases.

As used herein, the term "D5/B11", "D5/B11-like antibody", "D5/B11-like antibody or affinity matured version thereof", or similar terms is meant to include any form of a D5 or B11 antibody and/or antibody conjugate, any altered form (i.e., through for example, mutations to the $V_H$, $V_L$ or various constant regions of the antibody wherein the antibody retains essentially the same affinity to a gp41 pre-hairpin trimeric structure D5 or B11, and in turn having a neutralizing effect on various HIV strains) of a D5 or B11 antibody, including but not limited to any affinity matured version of a D5, B11, or like antibody, specific binding member and/or antibody conjugate.

Us used herein, "Ka" is intended to refer to the association constant of a particular antibody-antigen interaction, "Kd" is intended to refer to the dissociation constant of a particular antibody-antigen interaction, and "$IC_{50}$" is the concentration of antibody required to neutralize 50% of a HIV viral population in vitro.

As used herein, "HIV" is meant to represent either HIV-1, HIV-2, or HIV-1 and/or HIV-2. Amino acid numbering of HIV gp41 residues used herein relies on the numbering of Ratner et al. (1985, Nature 313: 277-283).

As used herein, "neutralizing" is used as in the art, namely to denote the ability of an isolated antibody to prevent viral infection in an in vitro cell/virus-based assay. Neutralizing activity may be measured quantitatively as the $IC_{50}$ value for that specific antibody. An antibody of the present invention is a "neutralizing antibody" or an "HIV neutralizing antibody" if that antibody is shown in an art accepted infectivity assay to neutralize at least one HIV isolate. A neutralizing antibody of the present invention may provide for increased utility by possessing a broader spectrum of HIV neutralizing activity. Such a broad neutralizing antibody will be an antibody which neutralizes more than one HIV isolate being diverse at the amino acid level (e.g., such as Bal, 89.6 and/or HOB). Preferably, a broadly neutralizing antibody is an antibody that will neutralize a mix of X4, R5, and X4/R5 isolates and/or have the ability to neutralize HIV strains from different cades. An antibody is determined to neutralize a specific HIV isolate if the $IC_{50}$ for that antibody is in a range up to about 100 uM.

As used herein, "transfection" is meant to include any method known in the art for introducing a nucleic acid molecule (e.g., expression vector) into host cells. For example, transfection includes calcium phosphate or calcium chloride mediated transfection, lipofection, infection with a viral vector construct and/or electroporation. The prokaryotic or eukaryotic cells disclosed herein and those host cells contemplated for use with the components of the present invention may either be transiently transfected or stably transformed with expression vectors disclosed herein. Such host cells may also be "transformed", meaning a genetic change to the target cell resulting from an incorporation of a nucleic acid molecule (e.g., expression vector).

BRIEF DESCRIPTION OF THE DRAWINGS

FIG. 2A-F shows the nucleotide and amino acid sequences for 5H/I1-BMV-D5 ("D5").

FIG. 3A-F shows the nucleotide and amino acid sequences for 5H/I1-BMV-B11 ("B11").

FIG. 4 shows a comparison of the amino acid sequence for 5H/I1-BMV-D5 ("D5") and 5H/I1-BMV-B11 ("B11").

FIGS. 5A and 5B show the subcloning strategy for generating a mammalian expression vector expressing the $V_H$ chain of an IgG4 immunoglobulin: (A) plasmid pEU8.2 (CAT), containing unique restriction sites BssHII and BstEII within the polylinker sequence; (B) the nucleotide sequence representing the D5 $V_H$ PCR product, with restriction sites for BssHII and BstEII.

FIGS. 6A and 6B show the subcloning strategy for generating a mammalian expression vector expressing the $V_L$ chain of an IgG4 immunoglobulin: (A) plasmid pEU3.2 (CAT), containing unique restriction sites ApaLI and PacI within the polylinker sequence; (B) the nucleotide sequence representing the D5 $V_L$ PCR product, with restriction sites for ApaLI and PacI.

FIGS. 7A and 7B show the subcloning strategy for generating a mammalian expression vector expressing the $V_H$ chain of an IgG1 immunoglobulin: (A) plasmid pEU1.2 (CAT), containing unique restriction sites BssHII and BstEII within the polylinker sequence; (B) the nucleotide sequence representing the B11 $V_H$ PCR product, with restriction sites for BssHII and BstEII.

FIGS. 8A and 8B show the subcloning strategy for generating a mammalian expression vector expressing the $V_L$ chain of an IgG1 immunoglobulin: (A) plasmid pEU3.2 (CAT), containing unique restriction sites ApaLI and PacI within the polylinker sequence; (B) the nucleotide sequence representing the B11 $V_L$ PCR product, with restriction sites for ApaLI and PacI.

FIG. 16 shows the gp41 pocket with (A) VHCDR3Phe56 binding into the "gp41 pocket", and (B) Trp628 and Trp631 of the C-peptide occupying the same position of Phe56 in gp41.

DETAILED DESCRIPTION OF THE INVENTION

Figure 14:
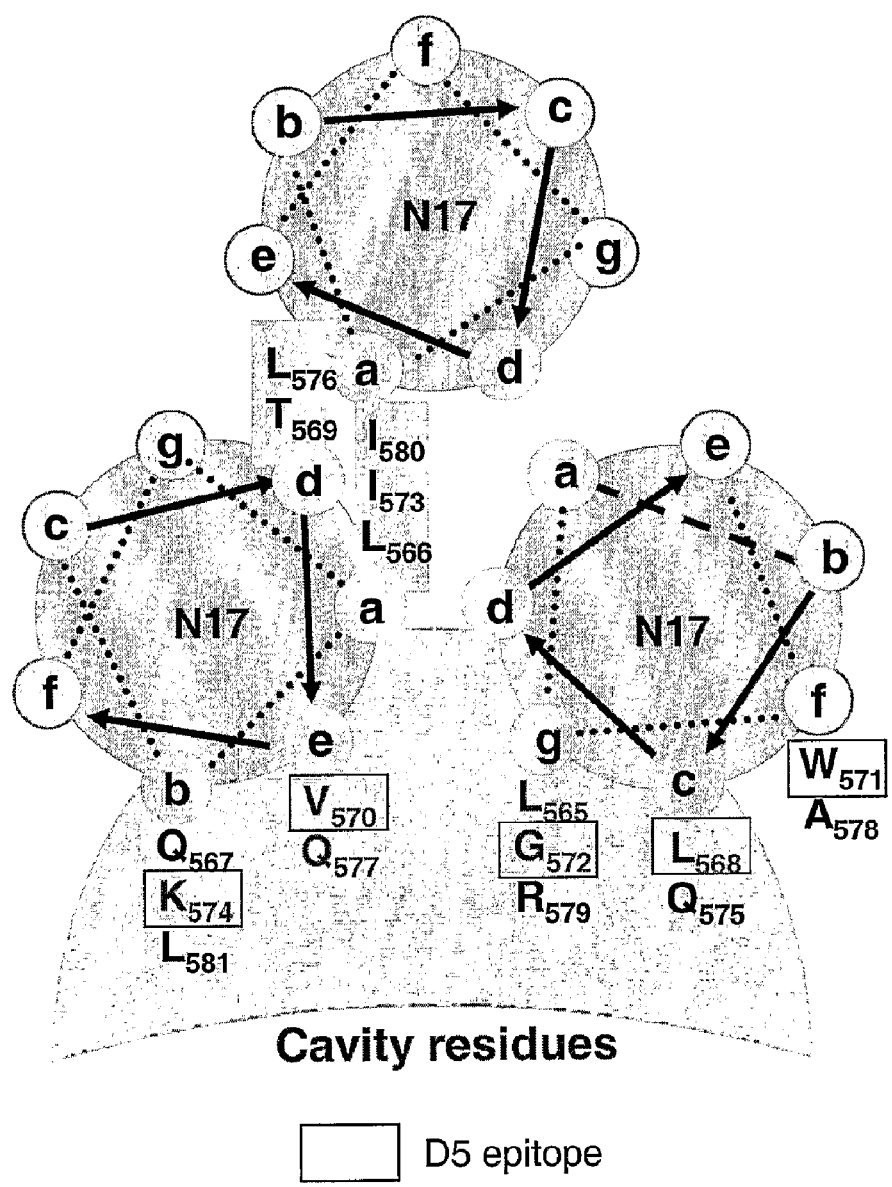
FIG. 14 shows a trimeric helical wheel model for the N17 pre-hairpin intermediate. The three critical residues (L568, W571, K574), a less critical residue (V570), and G572 are shown (boxed residues) to represent a conformational epitope on the gp41 trimeric, pre-hairpin structure.
Figure 15:
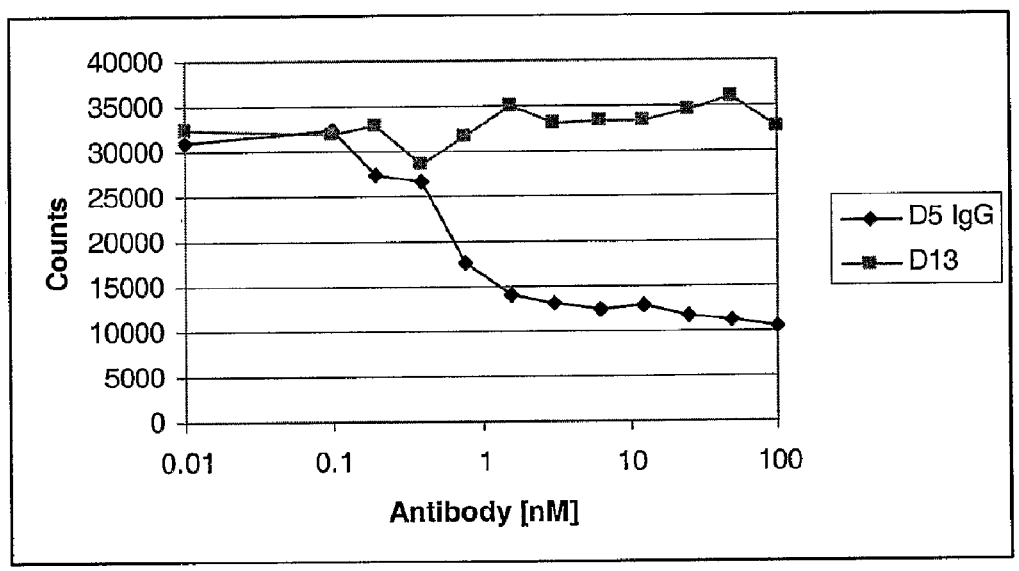
FIG. 15 shows an Alpha Screen assay suggesting that D5 IgG may function like T20/Fuzeon by preventing HR2 from engaging HR1. D5 IgG4 prevents the interaction of biotinylated IZN36 with C34-HA, which mimic the pre-fusion HR1/HR2 interaction in vitro. D13 is a mouse monoclonal antibody raised against 5-helix, but which does not bind the hydrophobic pocket of adjacent N17 trimer coils.

The present invention relates to a HIV neutralizing antibody that interacts with a hydrophobic pocket within the heptad repeat 1 (HR1) region of the ectodomain of the HIV transmembrane glycoprotein gp41. The interaction of the HIV surface glycoprotein gp120 with CD4 and a chemokine co-receptor (CXCR4 or CCR5) ultimately leads to displacement of gp120 and exposure of the transmembrane protein gp41. Conformational changes in gp41 ensue allowing HIV to fuse with a target cell membrane and enter the cell. For a review, see Eckert and Kim, 2001, *Annual Review Biochemistry* 70: 777-810. During this gp41-mediated membrane fusion process, the ecto-domain of gp41 transitions through various conformational intermediates that are believed to include a pre-hairpin structure. This pre-hairpin intermediate exposes the N-terminal fusion peptide which inserts into the target cell membrane. The ecto-domain proceeds to form a hairpin structure, which results in the juxtaposition of the target cell plasma membrane and the virion envelope. Gp41 exists in a trimeric state on the surface of the virion. The gp41 ecto-domain contains two distinct BR regions, designated HR1 and HR2. The HR1 region from three independent gp41 proteins interact with each other to form a trimeric coiled-coil structure that exposes on its surface three symmetrical grooves. To form the trimeric hairpin structure (or six-helical bundle), the HR2 regions fold back and interacts with the grooves present on the surface of the coiled-coil structure. In the groove, the C-terminal halves of adjacent HR1 segments form a hydrophobic pocket which accommodates three key residues from the N-terminal portion of the HR2 region. The integrity of this pocket is critical for fusion and HIV infectivity. It is an object of the present invention to identify human antibodies that target this pre-hairpin, pre-fusogenic N-helix coiled intermediate structure (see FIG. 14). This gp41-mediated fusion process represents an excellent target for the development of therapeutic antibodies. To identify such antibodies, phage display technology from Cambridge Antibody Technology (CAT) was utilized in conjunction with two specific selecting peptides, 5-Helix and IZN36, which both present the groove structure formed by adjacent HR1 regions. 5-Helix is composed of a series of three alternating N-peptides and two C-peptides derived from HR1 and HR2, respectively which are united by small peptidic linkers. The amino acid sequence of 5-helix, with peptide linkers and a COOH-terminal His tag, is as follows:

MQLLSGIVQQQNNLLRAIEAQQHLLQLTVWGIKQL QARILAGGSGGHTTWMEWDREINNYTSLIHSLIEE SQNQQEKNEQELLEGSSGGQLLSGIVQQQNNLLR AIEAQQHLLQLTVWGIKQLQARILAGGSGGHTTW MEWDREINNYTSLIHSLIEESQNQQEKNEQELLEG SSGGQLLSGIVQQQNNLLRAIEAQQHLLQLTVWG IKQLQARILAGGHHHHHHG (SEQ ID NO:13). The portion of 5-Helix in single underline represents the three N40 regions while the double underlined portion represents the two C38 regions, with the appropriate linkers and a His tag at the COOH terminus (i.e., -M-N40-N to C linker-C38-C to N linker-N40-N to C linker-C38-C to N linker-N40-His tag; see Root, et al., 2001, *Science* 291: 884-888). This artificial peptide folds into a 5-helical bundle due to the absence of one C-peptide, thus exposing one of three potential grooves. IZN36 is a chimeric peptide composed of a segment of amino acids that form a Leucine zipper (IZ) and the N peptide region from HR1 (N36). The amino acid sequence of IZN36 is as follows:

Ac—IKKEIEAIKKEQEAIKKKIEAIEKEISGIVQQQNN LLRAIEAQQHLLQLTVWGIKQLQARIL—NH$_2$ (SEQ ID NO:14; see Eckert and Kim, 2001, *Proc. Natl. Acad. Sci.* 98(20): 11187-11192). Both peptides represent inhibitors of HIV infection, likely due to their ability to engage the native HR2 region which becomes transiently exposed during the process of virion-mediated fusion.

Libraries of bacteriophages encoding selected regions of human IgG heavy and light variable chains (scFvs) were screened using biotinylated-5-Helix and IZN36 peptides. ScFvs that bound both peptides were tested for neutralizing capacity in an HIV-Reporter Particle assay. scFv-associated anti-viral activity was subsequently confirmed in a single cycle HIV infectivity assay (VERTICAL). Two scFvs, 5H/I1-BMV-D5 and 5H/I1-BMV-B11 (herein also referred to as "D5" and "B11", respectively), are exemplified herein to act as inhibitors of HIV entry. Transfer of variable heavy ($V_H$) and variable light ($V_L$) regions from these scFvs into full length IgGs preserved anti-viral activity.

The epitope for D5 antibody binding is localized to the hydrophobic pocket region formed by the carboxy terminal half of the HR1 region. Amino acids L568, W571 and K574 of gp41 appear critical for antibody binding and V570 appears to also contribute but to a lesser extent. By interacting with the hydrophobic pocket of the HR1 region, D5 IgG possesses the functional capacity of preventing the in vitro interaction of HR-derived N and C peptides. Antibody D5 may inhibit this HIV fusion with target cell membranes by interfering with the intramolecular interactions occurring between the gp41 HR1 and HR2 regions that lead to the formation of the 6-helical bundle. To this end, the present invention relates to a HIV neutralizing antibody that interacts at least partially with an epitope located within the hydrophobic pocket of the HR1 region of the trimeric, pre-hairpin, pre-fusogenic portion of the gp41 ectodomain, particularly in a "N17" region from about amino acid 565 to about amino acid 581 of gp41, and more particularly a HIV neutralizing antibody that interacts with a conformational epitope of the N-helices coil structure representing this pre-hairpin, pre-fusogenic structure. This epitope will comprise at least one, and preferably more than one, of the gp41 amino acid residues L568, V570, W571 and/or K574, and especially three amino acid residues: L568, W571; and K574 or all four amino acid residues: L568, V570, W571 and K574 in adjoining grooves present in the trimeric N-helices coiled structure encompassing the HR1 region of the gp41 ectodomain, with Gly572 contributing a spatial integrity to this region of the pre-fusion trimer. While the exemplified forms of D5 and B11 are single-chain (scFv) fragments and an IgG4 and IgG1 immunoglobulin, respectively, the antibodies of the present invention may take any form known to the artisan which preserves the binding specificity exemplified herein with both D5 and B11 scFvs and IgG2 antibodies. Such an HIV neutralizing antibody may be any antibody known in the art that binds to a disclosed gp41 N-helices coil epitope. The term "antibody" as used in any context within this specification is meant to include, but not be limited to, any specific binding member (defined infra), immunoglobulin class and/or isotype (e.g., IgG1, IgG2, IgG3, IgG4, IgM, IgA, IgD, IgE and IgM); and biologically relevant fragment or specific binding member thereof, including but not limited to Fab, F(ab')2, Fv and scFv, which are capable of binding the same epitope within the HR1-based hydrophobic pocket of the gp41 ectodomain as scFv and IgG2 forms of D5 and B11. Therefore, it is well known in the art, and is included as review only, that an "antibody" refers to a glycoprotein comprising at least two heavy (H) chains and two light (L) chains inter-connected by disulfide bonds, or an antigen binding portion thereof. A heavy chain is comprised of a heavy chain variable region ($V_H$) and a heavy chain constant region ($C_{H1}$, $C_{H2}$ and $C_{H3}$). A light chain is comprised of a light chain variable region ($V_L$) and a light chain constant region ($C_L$). The variable regions of both the heavy and light chains comprise a framework (FW) and complementarity determining regions (CDR). The four (4) FW regions are relatively conversed while CDR regions (CDR1, CDR2 and CDR3) represent hypervariable regions and are arranged from NH2 terminus to the COOH terminus as follows: FW1, CDR1, FW2, CDR2, FW3, CDR3, FW4. The variable regions of the heavy and light chains contain a binding domain that interacts with an antigen while, depending of the isotype, the constant region(s) may mediate the binding of the immunoglobulin to host tissues or factors. That said, also included in the working definition of "antibody" are chimeric antibodies, humanized antibodies, a recombinant antibody which, as an example but not a limitation, may comprise a D5 or B11 $V_H$ CDR3 fused to a partial or non-D5/B11 antibody; as well as human antibodies generated from a transgenic non-human animal as well as antibodies selected from libraries using enrichment technologies available to the artisan. Antibody fragments are obtained using techniques readily known and available to those of ordinary skill in the art, as reviewed below. Therefore, an "antibody", as defined herein is any such entity or specific binding member, which specifically binds to the gp41 epitope as described herein. Any such entity is a candidate for therapeutic applications. Referring to an antibody as an example of a "specific binding member", it is noted that an antigen-antibody interaction is a subset of what may be generally referred to as a "specific binding pair", which consists of at least two components referred to as this "specific binding member." A specific binding member describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. Of course, this specification discloses an antigen-antibody type interaction. As discussed throughout this specification, an "antibody" represents a specific binding member that may take on any relevant form which promotes biological activity similar to or more pronounced than for D5/B11 scFv and/or IGg forms. Therefore, the term "antibody" describes an immunoglobulin, whether natural or partly or wholly synthetically produced; any polypeptide or protein having a binding domain which is, or is substantially homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd and diabodies, as discussed without limitation infra. It is known in the art that it is possible to manipulate monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced. To this end and as discussed herein, as antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Thus, the "antibody" of the present invention is an antibody that comprises an "antigen-binding portion" or "specific binding member" that retains the ability to bind to the HR1 region of gp41 as disclosed herein for a D5 and/or a B11 antibody. Such an entity may be a binding fragment encompassed within the term "antigen-binding portion" or "specific binding member" of an antibody including but not limited to (i) a Fab fragment, a monovalent fragment consisting of the $V_L$, $V_H$, $C_L$ and $C_H$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment, which comprises a $V_H$ domain; (vi) an isolated complementarily determining region (CDR); (vii) a 'scAb', an antibody fragment containing $V_H$ and $V_L$ as well as either $C_L$ or $C_{H1}$; and (viii) artificial antibodies based upon protein scaffolds, including but not limited to fibronectin type III polypeptide antibodies (e.g., see U.S. Pat. No. 6,703,199, issued to Koide on Mar. 9, 2004 and PCT International Application publication no. WO 02/32925). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv), as disclosed herein for scFv versions of D5 and B11). As supported by the data presented herein, such a scFvS antibody contains the appropriate "antigen-binding portion" of an antibody. Therefore, any component of D5/B14-like antibodies as disclosed herein (i.e., one or more of the CDR1, 2 and/or 3 regions from the $V_H$ and/or $V_L$ regions of D5/B11-like antibody) are candidates for inclusion, alone or in combination, with the various antibody forms disclosed throughout this specification.

Another antibody suggested by the present disclosure is an antibody which comprises at least one CDR region from either the variable light and/or heavy chain from D5, B11, or an affinity matured form of either. CDR regions which are contemplated for transfer to a relevant "antibody" scaffold comprise at least one of the respective $V_H$ and $V_L$ CDR regions as disclosed in FIG. 4, namely D5 and B11 $V_H$ CDR1 (SYAIS; contained within SEQ ID NO:2 and 8, respectively); D5 $V_H$ CDR2 GIIPIFGTANYAQKFQG; contained within SEQ ID NO:2); B11 $V_H$ CDR2 (GIIPLFDTSNYAQNFQG; contained within SEQ ID NO: 8); D5 $V_H$ CDR3 (DNPTLLGSDY; contained within SEQ ID NO:2); B11 $V_H$ CDR3 (DNPLLLAMDV; contained within SEQ ID NO: 8); as well as D5 and B11 $V_H$ CDR1 (RASEGIYHWLA); $V_H$ CDR2 (KASSLAS); and $V_H$ CDR3 (QQYSNYPLT), each contained within both SEQ ID NOs: 2 and 8. Any combination of one or more of these CDR regions may be utilized as part and parcel of any acceptable scaffold as discussed herein, such that any antibody/specific binding member is one that comprises at least substantially similar neutralizing activity against HIV infection of host cells.

As used herein, the term "epitope" relates to a protein determinant (such as the hydrophobic pocket formed within the trimeric N-helix coil structure present as a pre-hairpin, pre-fusogenic intermediate within the gp41 heptad repeat 1 (HR1) region which interacts with a D5 and/or B11 antibody) capable of specific binding to an antibody (such as an antibody or antibody-binding portion which mimics D5 and/or B11 specific binding). It is well known that epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Alone, a D5 and/or B11 antibody or an affinity matured version thereof may be used as a therapeutic agent to treat persons infected with HIV. This antibody would be administered to an individual, preferably by intravenous injection, either alone or in combination with other anti-HIV therapy. Therefore, D5 and/or B11, or an affinity matured version thereof, or a small molecule inhibitor of D5- or B11-like binding with HIV-fusion inhibiting properties, could potentially be used in conjunction with one or more anti-retroviral compounds. Additionally, antigenic peptides designed for the purpose of eliciting D5-/B11-like antibody responses in the setting of therapeutic immunization could be co-administered with a variety of anti-retrovirals. Such peptides could elicit, from the immunized individual, D5-/B11-like antibodies that could function in combination with a variety of anti-retrovirals to inhibit HIV replication. Classes of anti-retrovirals that could be used with D5-based agents include, but are not limited to, nucleoside reverse transcriptase inhibitors (NRTIs), non-nucleoside reverse transcriptase inhibitors (NNRTIs) and protease inhibitors (PIs). The epitope defined for this antibody will help in the design of peptide immunogens that may be used to elicit neutralizing antibody responses in prophylactic or therapeutic vaccination strategies. Additionally, an antibody/peptide interaction assay involving D5 and/or B11 antibody, or related antibody thereof, and various HR1 hydrophobic pocket-containing peptides may be devised. Examples of peptide substrates include 5-Helix, IZN36, IZN23 and IZN17. Such interaction assays may be utilized for the purpose of high throughput screening to identify small molecules that occupy the hydrophobic pocket of HR1 and displace the antibody. Such small molecules may, in turn, represent HIV fusion inhibitors if they successfully prevent the intramolecular interaction of HR1 and HR2. The antibodies of the present invention may also be utilized as a research tool in immunochemical assays, such as Western blots, ELISAs, radioimmunoassays, immunohistochemical assays, immunoprecipitations, or other immunochemical assays known in the art (see, for example, *Immunological Techniques Laboratory Manual*, ed. Goers, J. 1993, Academic Press).

Additional polyclonal or monoclonal antibodies within the scope of the present invention may be raised by known techniques. Monospecific murine (mouse) antibodies showing specificity to the gp41 conformational epitope disclosed herein may be purified from mammalian antisera containing antibodies reactive against this region, or may be prepared as monoclonal antibodies using the technique of Kohler and Milstein (1975, Nature 256: 495-497). Monospecific antibody as used herein is defined as a single antibody species or multiple antibody species with homogenous binding characteristics similar to that exemplified herein for D5 and/or B11. The monoclonal antibody initially generated by the Kohler and Milstein technology is a murine monoclonal antibody derived entirely from mice; more specifically murine hybridomas generated from the fusion of mouse myeloma and mouse spleen cells. Homogenous binding as used herein refers to the ability of the antibody species to bind to a specific antigen or epitope, such as the hydrophobic pocket of the HR1 region of the gp41 pre-hairpin, trimeric coiled coil structure. Such Mabs are raised by immunizing animals such as mice, rats, guinea pigs, rabbits, goats, horses and the like, with an appropriate concentration of antigen, such as a peptide representing the hydrophobic pocket of the HR1 region of gp41 (e.g., including but in no way limited to 5-Helix or IZN36) or a synthetic peptide generated from a this portion of gp41 with or without an immune adjuvant. Preimmune serum is collected prior to the first immunization. Each animal receives between about 0.1 mg and about 1000 mg of gp41 antigen associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of gp41 antigen thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of gp41 antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C. The mice receive an initial immunization on day 0 and are rested for about 3 to about 30 weeks. Immunized mice are given one or more booster immunizations of about 1 to about 100 mg of gp41 antigen in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused and selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using a relevant portion of gp41 as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press. Mab specificity similar to that exemplified herein may be determined using assays similar to those described herein, such as a Biocore assay using 5-helix and/or IZN36. Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8-12 days after cell transfer and the monoclonal antibodies are purified by techniques known in the art. In vitro production of anti-gp41 mAb is carried out by growing the hybridoma in DMEM containing about 2% fetal calf serum to obtain sufficient quantities of the specific mAb. The mAb are purified by techniques known in the art. Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques.

Beyond species specific monoclonal antibodies described above, the antibodies of the present invention may also be in the form of a "chimeric antibody", a monoclonal antibody constructed from the variable regions derived from say, the murine source, and constant regions derived from the intended host source (e.g., human; for a review, see Morrison and Oi, 1989, *Advances in Immunology,* 44: 65-92). The use of recombinant DNA technology to generate a chimeric antibody is a result from a long time inability of researchers to generate human Mabs with conventional hybridoma techniques. It has been known in the art for years that a mouse Mab can be engineered to make the antibody humanlike (i.e., substitution of the constant regions of the mouse Mab with human segments). To this end, the artisan may use known techniques to generate a chimeric antibody with the binding characteristics of antibodies disclosed herein. The variable light and heavy genes from the rodent (e.g., mouse) antibody are cloned into a mammalian expression vector which contains an appropriate human light chain and heavy chain coding region, respectively. These heavy and light "chimeric" expression vectors are cotransfected into a recipient cell line and selected and expanded by known techniques. This cell line may then be subjected to known cell culture techniques, resulting in production of both the light and heavy chains of a chimeric antibody. Such chimeric antibodies have historically been shown to have the antigen-binding capacity of the original rodent monoclonal while significantly reducing immunogenicity problems upon host administration.

A logical improvement to the chimeric antibody is the "humanized antibody", which arguably reduces the chance of the patient mounting an immune response against a therapeutic antibody when compared to use of a chimeric or full murine monoclonal antibody. The strategy of "humanizing" a murine Mab is based on replacing amino acid residues which differ from those in the human sequences by site directed mutagenesis of individual residues or by grafting of entire complementarily determining regions (Jones et al., 1986, *Nature* 321: 522-526). This technology is again now well known in the art and is represented by numerous strategies to improve on this technology, namely by implementing strategies including, but not limited to, "reshaping" (see Verhoeyen, et al., 1988, *Science* 239: 1534-1536), "hyperchimerization" (see Queen, et al., 1991, *Proc. Natl. Acad. Sci.* 88:2869-2873) or "veneering" (Mark, et al., 1994, *Derivation of Therapeutically Active Humanized and Veneered anti-CD18 Antibodies*. In: Metcalf and Dalton, eds. *Cellular Adhesion: Molecular Definition to Therapeutic Potential*. New York: Plenum Press, 291-312). These strategies all involve to some degree sequence comparison between rodent and human sequences to determine whether specific amino acid substitutions from a rodent to human consensus is appropriate. Whatever the variations, the central theme involved in generating a humanized antibody relies on CDR grafting, where these three antigen binding sites from both the light and heavy chain are effectively removed from the rodent expressing antibody clone and subcloned (or "grafted") into an expression vector coding for the framework region of the human antibody. Therefore, a "humanized antibody" is effectively an antibody constructed with only murine CDRs (minus any additional improvements generated by incorporating one or more of the above-mentioned strategies), with the remainder of the variable region and all of the constant region being derived from a human source.

Yet another improvement over re-engineered antibodies as reviewed above is the generation of fully human monoclonal antibodies by two distinct methodologies. The first involves the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, fully human monoclonal antibodies. This technology is again now well known in the art and is fully detailed in various publications, including but not limited to U.S. Pat. Nos. 5,939,598; 6,075,181; 6,114,598; 6,150,584 and related family members (assigned to Abgenix, disclosing their XENOMOUSE® technology); as well as U.S. Pat. Nos. 5,545,806; 5,569,825; 5,625,126; 5,633,425; 5,789,650; 5,877,397; 5,661,016; 5,814,318; 5,874,299; and 5,770,429 (assigned to GenPharm International and available through Medarex, under the umbrella of the "UltraMab Human Antibody Development System"). See also a review from Kellerman and Green, 2002, *Curr. Opinion in Biotechnology* 13: 593-597.

Finally, techniques available to the artisan for the selection of antibody fragments from libraries using enrichment technologies, including but not limited to phage display, ribosome display (Hanes and Pluckthün, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies which specifically bind to the HR1 region of gp41. As exemplified herein, single-chain antibodies are selected from a library of single chain antibodies produced directly utilizing filamentous phage technology. Phage display technology is known in the art (e.g., see technology from Cambridge Antibody Technology (CAT)) as utilized herein and initially disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members and/or application which rely on priority filing GB 9206318, filed 24 May 1992; see also Vaughn, et al. 1996, *Nature Biotechnology* 14: 309-314). Example 1 shows the selection of D5 and B11 single chain antibodies from a filamentous phage library based on Vaughan, et al., supra. Single chain antibodies may also be designed and constructed using available recombinant DNA technology, such as a DNA amplification method (e.g., PCR), or possibly by using a respective hybridoma cDNA as a template. Single-chain antibodies can be mono- or bispecific; bivalent or tetravalent. A nucleotide sequence encoding a single-chain antibody can be constructed using manual or automated nucleotide synthesis, cloned into an expression construct using standard recombinant DNA methods, and introduced into a cell to express the coding sequence, as described below.

The term "recombinant human antibody", represents a viable subset of "antibodies" generated by various means of recombinant DNA technology and non-human transgenics that are well known in the art. Such methodology is utilized to generate an antibody from one or the following origins: (i) a scFv or alternative antibody isolated from a combinatorial human antibody library, such as the CAT phage display library used to generate D5 and B11; (ii) a partial or complete antibody generated from a respective expression vector stably or transiently transfected into a host cell, preferably a mammalian host cell; and/or (iii) an antibody isolated from a non-human transgenic animal which contains human immunoglobulin genes, or by any other known methodology which relies of the recombinant 'mixing and matching' of human immunoglobulin gene sequences to other DNA sequences in order to generate the human recombinant antibody of interest.

As introduced supra, the antibodies of the present invention, while exemplified herein as scFvs, IgG4 (D5) or IgG1 (B11), may take the form of any type of antibody, relevant antibody fragment, antibody binding portion, specific binding member, or any other relevant terminology known in the art which refers to an entity which at least substantially retains the binding specificity/neutralization activity as shown for D5 and/or B11. As noted above, the initial D5 and B11 antibody was identified by screening a Cambridge Antibody Technology phage display library. A primary screen was run against 5-Helix, followed by a secondary screen against IZN36. ScFvs that bound both peptides were tested for neutralizing and anti-viral activity in a HIV-Reporter Particle assay and VERTICAL assay, respectively. These assays resulted in the confirmation of two scFvs, 5H/I1-BMV-D5 ("D5") and 5H/I1-BMV-B11 ("B11") as inhibitors of HIV entry. To this end, the present invention also relates to the nucleic acid molecules and associated amino acid sequences which relate to the scFvs, D5 and B11, and more specifically, an isolated nucleic acid molecule (polynucleotide) which encodes a biologically relevant portion of D5, B11, or affinity matured version or otherwise mutated version of D5 or B11 antibody. These isolated or purified nucleic acid molecules will represent the $V_H$ and/or $V_L$ portions of a D5 or B11 antibody, as identified by screening a phage display library with 5-helix and IZN36, as described herein. These nucleic acids are substantially free from other nucleic acids. For most cloning purposes, DNA is a preferred nucleic acid. These DNA molecules may be subcloned into an expression vector and subsequently transfected into a host cell of choice wherein the recombinant host cell provides a source for substantial levels of a relevant portion of the D5, B11, or affinity matured version thereof. Such procedures may be used for a variety of utilities, such as generating scFvs or for co-expressing these $V_H$ and $V_L$ chains in a mammalian expression vector system which encodes human $C_H$ and $C_L$ regions, of say, an IgG antibody (e.g., see Example Sections 2 and 3).

The degeneracy of the genetic code is such that, for all but two amino acids, more than a single codon encodes a particular amino acid. This allows for the construction of synthetic DNA that encodes an antibody of the present invention where the nucleotide sequence of the synthetic DNA differs significantly from the nucleotide sequences disclosed herein, but still encodes such an antibody. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the an antibody of the present invention. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His =Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutarmine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU The present invention relates to an isolated DNA molecule as well as the representative mRNA expressing a biologically relevant portion of an antibody (i.e., $V_H$ and $V_L$ chain, joined by a $(G_4S)_3$ linker) that interacts with a hydrophobic pocket within adjacent coils of the heptad repeat 1 (HR1) region of the ectodomain of the HIV transmembrane glycoprotein gp41, this DNA molecule comprising the nucleotide sequence of D5, disclosed herein as SEQ ID NO:1, as follows:

```
                                    (SEQ ID NO: 1)
CAGGTGCAGC TGGTGCAGTC TGGGGCTGAG GTGAGGAAGC
CTGGGGCCTC AGTGAAGGTC TCCTGCAAGG CTTCTGGAGA
CACCTTCAGC AGCTATGCTA TCAGCTGGGT GCGACAGGCC
CCTGGACAAG GGCTTGAGTG GATGGGAGGG ATCATCCCTA
TTTTTGGTAC AGCAAACTAC GCACAGAAGT TCCAGGGCAG
AGTCACGATT ACCGCGGACG AATCCACGAG TACAGCCTAC
ATGGAGCTGA GCAGCCTGAG ATCTGAAGAC ACGGCCATTT
ATTACTGCGC GAGAGATAAC CCGACACTAC TCGGCTCTGA
CTACTGGGGC AAGGGAACCC TGGTCACCGT CTCGAGTGGT
GGAGGCGGTT CAGGCGGAGG TGGCAGCGGC GGTGGCGGAT
CGGACATCCA GATGACCCAG TCTCCTTCCA CCCTGTCTGC
ATCTATTGGA GACAGAGTCA CCATCACCTG CCGGGCCAGT
GAGGGTATTT ATCACTGGTT GGCCTGGTAT CAGCAGAAGC
CAGGGAAAGC CCCTAAACTC CTGATCTATA AGGCCTCTAG
TTTAGCCAGT GGGGCCCCAT CAAGGTTCAG CGGCAGTGGA
TCTGGGACAG ATTTCACTCT CACCATCAGC AGCCTGCAGC
CTGATGATTT TGCAACTTAT TACTGCCAAC AATATAGTAA
TTATCCGCTC ACTTTCGGCG GAGGGACCAA GCTGGAGATC
AAA.
```

This nucleotide sequence, as noted above, encodes for the $V_H$ and $V_L$ chains of D5, joined with a series of codons expressing a $(G_4S)_3$ linker. Therefore, SEQ ID NO:1 represents a entire open reading frame encoding for the isolated D5 scFv as follows:

```
                                    (SEQ ID NO: 2)
QVQLVQSGAE VRKPGASVKV SCKASGDTFS SYAISWVRQA
PGQGLEWMGG IIPIFGTANY AQKFQGRVTI TADESTSTAY
MELSSLRSED TAIYYCARDN PTLLGSDYWG KGTLVTVSSG
GGGSGGGGSG GGGSDIQMTQ SPSTLSASIG DRVTITCRAS
EGIYHWLAWY QQKPGKAPKL LIYKASSLAS GAPSRFSGSG
SGTDFTLTIS SLQPDDFATY YCQQYSNYPL TFGGGTKLEI
K
```

The $(G_4S)_3$ linker between the $NH_2$-terminal $V_H$ chain and the COOH-terminal $V_L$ chain is underlined. To this end, the $NH_2$-terminal $V_H$ chain comprises the following amino acid sequence:

```
    (SEQ ID NO: 4, contained within SEQ ID NO: 2)
QVQLVQSGAE VRKPGASVKV SCKASGDTFS SYAISWVRQA
PGQGLEWMGG IIPIFGTANY AQKFQGRVTI TADESTSTAY
MELSSLRSED TAIYYCARDN PTLLGSDYWG KGTLVTVSS;
``` while the COOH-terminal $V_L$ chain comprises the following amino acid sequence:

(SEQ ID NO: 6, contained within SEQ ID NO: 2)
DIQMTQSPST LSASIGDRVT ITCRASEGIY HWLAWYQQKP

GKAPKLLIYK ASSLASGAPS RFSGSGSGTD FTLTISSLQP

DDFATYYCQQ YSNYPLTFGG GTKLEIK.

The complete breakdown for nucleotide and amino acids sequences which represent the $V_H$, $V_L$ and linker sequences is shown in FIG. 2A-F, representing SEQ ID NOs:1-6, respectively. More specifically, SEQ ID NO:3 represents nucleotides 1-357 (FIG. 2C) of SEQ ID NO:1 and SEQ ID NO:5 represents nucleotides 403-723 (FIG. 2E) of SEQ ID NO:1.

Similar to D5 supra, the present invention relates to an isolated DNA molecule as well as the representative mRNA expressing a biologically relevant portion of the scFv antibody B11, which also interacts with the adjacent coils of the trimeric HR1 region of the gp41 ectodomain. This DNA molecule comprises the scFv encoding nucleotide sequence disclosed herein as SEQ ID NO:7, as follows:

(SEQ ID NO: 7)
CAGGTGCAGC TGGTGCAATC TGGGGCTGAG GTGAAGAAGC

CTGGGTCCTC GGTGAAGGTC TCCTGCAAGG CTTCTGGAGG

CACCTTCAGC AGCTATGCTA TCAGCTGGGT GCGACAGGCC

CCTGGACAAG GGCTTGAGTG GATGGGAGGG ATCATCCCTC

TCTTTGATAC ATCAAACTAC GCACAGAACT TCCAGGGCAG

AATCACGATA ACTGCGGACA AATCCACGAG TACAGCCTAC

ATGGAACTGA GCAGCCTGAG ATTTGAGGAC ACGGCCATTT

ATTACTGTGC GAGAGATAAC CCTTTACTTC TCGCTATGGA

TGTCTGGGGG AAAGGGACCA CGGTCACCGT CTCGAGTGGT

GGAGGCGGTT CAGGCGGAGG TGGCAGCGGC GGTGGCGGAT

CGGACATCCA GATGACCCAG TCTCCTTCCA CCCTGTCTGC

ATCTATTGGA GACAGAGTCA CCATCACCTG CCGGGCCAGT

GAGGGTATTT ATCACTGGTT GGCCTGGTAT CAGCAGAAGC

CAGGGAAAGC CCCTAAACTC CTGATCTATA AGGCCTCTAG

TTTAGCCAGT GGGGCCCCAT CAAGGTTCAG CGGCAGTGGA

TCTGGGACAG ATTTCACTCT CACCATCAGC AGCCTGCAGC

CTGATGATTT TGCAACTTAT TACTGCCAAC AATATAGTAA

TTATCCGCTC ACTTTCGGCG GAGGGACCAA GCTGGAGATC

AAA.

This nucleotide sequence encodes for the $V_H$ and $V_L$ chains of B11, and as with D5, joined with a series of codons expressing a $(G_4S)_3$ linker. Therefore, SEQ ID NO:7 represents a entire open reading frame encoding for the isolated B11 scFv as follows:

(SEQ ID NO: 8)
QVQLVQSGAE VKKPGSSVKV SCKASGGTFS SYAISWVRQA

PGQGLEWMGG IIPLFDTSNY AQNFQGRITI TADKSTSTAY

MELSSLRFED TAIYYCARDN PLLLAMDVWG KGTTVTVSS<u>G</u>

GGGSGGGGSG GGGS</u>DIQMTQ SPSTLSASIG DRVTITCRAS

EGIYHWLAWY QQKPGKAPKL LIYKASSLAS GAPSRFSGSG

SGTDFTLTIS SLQPDDFATY YCQQYSNYPL TFGGGTKLEI

K.

The $(G_4S)_3$ linker between the NH$_2$-terminal $V_H$ chain and the COOH-terminal $V_L$ chain is underlined. To this end, the NH$_2$-terminal $V_H$ chain comprises the following amino acid sequence:

(SEQ ID NO: 10, contained within SEQ ID NO: 8)
QVQLVQSGAE VKKPGSSVKV SCKASGGTFS SYAISWVRQA

PGQGLEWMGG IIPLFDTSNY AQNFQGRITI TADKSTSTAY

MELSSLRFED TAIYYCARDN PLLLAMDVWG KGTTVTVSS;

while the COOH-terminal $V_L$ chain comprises the following amino acid sequence:

(SEQ ID NO: 12, contained within SEQ ID NO: 8)
DIQMTQSPST LSASIGDRVT ITCRASEGIY HWLAWYQQKP

GKAPKLLIYK ASSLASGAPS RFSGSGSGTD FTLTISSLQP

DDFATYYCQQ YSNYPLTFGG GTKLEIK.

The complete breakdown for nucleotide and amino acids sequences which represent the $V_H$, $V_L$ and linker sequences is shown in FIG. 3A-F, representing SEQ ID NOs: 7-12, respectively. More specifically, SEQ ID NO:9 represents nucleotides 1-357 (FIG. 3C) of SEQ ID NO:7 and SEQ ID NO:9 represents nucleotides 403-723 (FIG. 3E) of SEQ ID NO:7.

The isolation and characterization of the D5 and B11 scFV encoding nucleic acid molecules of the present invention were identified as described in detail in Example Sections 1 and 2. These DNA and mRNA molecules, as discussed herein, are especially useful for direct use as a scFv, or as described herein and well known in the art, to use for the generation of recombinant human antibody constructions. Such recombinant expression vectors may then be stably or transiently transfected into an appropriate cell line for the generation of alternative antibody form, such as the IgG4 (D5) and IgG1 (B11) version exemplified in Example Sections 1 and 2.

The present invention also relates to a substantially purified form of a respective D5, B11, or D5- or B11-like antibody binding proteins, or functional equivalents thereof, including but not limited to a substantially purified form as disclosed in FIG. 2A-F (i.e., SEQ ID NOs: 2, 4 and 6) and in FIG. 3A-F (i.e., SEQ ID NOs: 8, 10 and 12) as well as respective light and/or heavy chain CDR regions (e.g., $V_H$CDR3) as shown in FIG. 4. An "isolated antibody," or "substantially isolated protein" or "substantially purified protein" or "substantially purified form" or any like statement, as used herein, is intended to refer to an antibody/protein or relevant portion therein (e.g., such as an alternative form which comprises a biologically relevant portion of D5 or B11 (e.g., such as the CDR3 region from the D5 or B11 heavy chain) which is substantially free of other antibodies/proteins having different antigenic specificities or amino acid makeup as a respective D5, B11, or D5- or B11-like antibody binding proteins. Therefore, the term "isolated" is used herein as it is used within the art. Namely, the state in which antibodies/specific binding members, nucleic acid molecules and the such are found. Antibodies/specific binding members and nucleic acid molecules will be free or substantially free of material with which they are naturally associated such as other polypeptides or nucleic acids with which they are found in their natural environment, or the environment in which they are prepared (e.g. cell culture) when such preparation is by recombinant DNA technology (practiced in vitro) or in vivo. Isolated" covers any form containing the identified and characterized component(s) of the present invention following removal from that initial environment. Examples, but certainly not limitations, include pharmaceutical formulations, formulation with diluents, adjuvants and the such, antibodies/specific binding members, nucleic acid molecules and portions thereof which have been modified (e.g., antibody glycosylation) either in vitro or in vivo and removed from that environment.

The present invention also relates to biologically active fragments and/or mutants of the D5, B11, or D5- or B11-like antibody binding proteins comprising the amino acid sequence as set forth in SEQ ID NOs:2, 4, 6, 8, 10 and 12, including but not necessarily limited to amino acid substitutions (e.g., as a directed form of affinity maturation of the $V_H$ or $V_L$ regions), deletions, additions, amino terminal truncations and carboxy-terminal truncations such that these mutations provide a basis for an antibody or antibody binding portion that results in a similar or improved version of a D5, B11, or D5- or B1 like antibody binding proteins.

The present invention notes the existence of codon redundancy which may result in differing DNA molecules expressing an identical antibody or portion thereof (e.g., alternative nucleic acid molecules encoding an identical scFv or a $V_H$ and/or $V_L$ portion of an IgG). For purposes of this specification, a sequence bearing one or more replaced codons will be defined as a degenerate variation. Another source of sequence variation may occur through RNA editing. Such RNA editing may result in another form of codon redundancy, wherein a change in the open reading frame does not result in an altered amino acid residue in the expressed protein. Also included within the scope of this invention are mutations either in the DNA sequence or the translated antibody which improve the ultimate physical properties of the expressed antibody. To this end, the present invention relates to (i) affinity matured versions of D5 and/or B11; and/or (ii) mutated forms of D5 and/or B11, including but not limited to one or more mutations in the CDR1, CDR2 an/or CDR3 regions as generated through known affinity maturation methodology and recombinant DNA techniques known for introducing site specific mutation. Such alternative antibodies will retain basic interaction characteristics described herein for D5 and/or B11 but will result in a more effective biological response, including but not limited to one or more of increased anti-viral activity (increased HIV neutralizing activity as measured in a decreased $IC_{50}$), improved Ka and/or or Kd rates for interaction with the hydrophobic pocket of the N-helices within the HR1 region of gp41, etc.

Table 1 shows the nucleotide sequence comparison between D5 and B11 while Table 2 shows the amino acid comparison between D5 and B11.

TABLE 1

```
D5  CAGGTGCAGCTGGTGCAGTCTGGGGCTGAGGTGAGGAAGCCTGGGGCCTCAGTGAAGGTC    (SEQ ID NO:
                                                                   1)
B11 CAGGTGCAGCTGGTGCAATCTGGGGCTGAGGTGAAGAAGCCTGGGTCCTCGGTGAAGGTC    (SEQ ID NO:
                                                                   7)
    *************** **************** ********* **** ********

D5  TCCTGCAAGGCTTCTGGAGACACCTTCAGCAGCTATGCTATCAGCTGGGTGCGACAGGCC
B11 TCCTGCAAGGCTTCTGGAGGCACCTTCAGCAGCTATGCTATCAGCTGGGTGCGACAGGCC
    ******************* ****************************************

D5  CCTGGACAAGGGCTTGAGTGGATGGGAGGGATCATCCCTATTTTTGGTACAGCAAACTAC
B11 CCTGGACAAGGGCTTGAGTGGATGGGAGGGATCATCCCTCTCTTTGATACATCAAACTAC
    *************************************** * **** **** ********

D5  GCACAGAAGTTCCAGGGCAGAGTCACGATTACCGCGGACGAATCCACGAGTACAGCCTAC
B11 GCACAGAACTTCCAGGGCAGAATCACGATAACTGCGGACAAATCCACGAGTACAGCCTAC
    ******** ************ ****** ** ****** *********************

D5  ATGGAGCTGAGCAGCCTGAGATCTGAAGCACGGCCATTTATTACTGCGCGAGAGATAAC
B11 ATGGAACTGAGCAGCCTGAGATTTGAGGACACGGCCATTTATTACTGTGCGAGAGATAAC
    ***** *************** *** *********************   ***********

D5  CCGACACTACTCGGCTCTGACTACTGGGGCAAGGGAACCCTGGTCACCGTCTCGAGTGGT
B11 CCTTTACTTCTCGCTATGGATGTCTGGGGAAAGGGACCACGGTCACCGTCTGGAGTGGT
    **  *** ****    ****** ** ** ***   ******************

D5  GGAGGCGGTTCAGGCGGAGGTGGCAGCGGCGGTGGCGGATCGGACATCCAGATGACCCAG
B11 GGAGGCGGTTCAGGCGGAGGTGGCAGCGGCGGTGGCGGATCGGACATCCAGATGACCCAG
    ************************************************************

D5  TCTCCTTCCACCCTGTCTGCATCTATTGGAGACAGAGTCACCATCACCTGCCGGGCCAGT
B11 TCTCCTTCCACCCTGTCTGCATCTATTGGAGACAGAGTCACCATCACCTGCCGGGCCAGT
    ************************************************************

D5  GAGGGTATTTATCACTGGTTGGCCTGGTATCAGCAGAAGCCAGGGAAAGCCCCTAAACTC
B11 GAGGGTATTTATCACTGGTTGGCCTGGTATCAGCAGAAGCCAGGGAAAGCCCCTAAACTC
    ************************************************************

D5  CTGATCTATAAGGCCTCTAGTTTAGCCAGTGGGGCCCCATCAAGGTTCAGCGGCAGTGGA
```

TABLE 1-continued

```
B11 CTGATCTATAAGGCCTCTAGTTTAGCCAGTGGGGCCCCATCAAGGTTCAGCGGCAGTGGA
    ************************************************************

D5  TCTGGGACAGATTTCACTCTCACCATCAGCAGCCTGCAGCCTGATGATTTTGCAACTTAT
B11 TCTGGGACAGATTTCACTCTCACCATCAGCAGCCTGCAGCCTGATGATTTTGCAACTTAT
    ************************************************************

D5  TACTGCCAACAATATAGTAATTATCCGCTCACTTTCGGCGGAGGGACCAAGCTGGAGATC
B11 TACTGCCAACAATATAGTAATTATCCGCTCACTTTCGGCGGAGGGACCAAGCTGGAGATC
    ************************************************************

D5  AAA
B11 AAA
```

TABLE 2

```
D5  QVQLVQSGAEVRKPGASVKVSCKASGDTFSSYAISWVRQAPGQGLEWMGGIIPIFGTANY   (SEQ ID NO:
                                                                  2)
B11 QVQLVQSGAEVKKPGSSVKVSCKASGGTFSSYAISWVRQAPGQGLEWMGGIIPLFDTSNY   (SEQ ID NO:
                                                                  8)
    **********:***:*********** .*****************************:*.*:**

D5  AQKFQGRVTITADESTSTAYMELSSLRSEDTAIYYCARDNPTLLGSDYWGKGTLVTVSSG
B11 AQNFQGRITITADKSTSTAYMELSSLRFEDTAIYYCARDNPLLLAMDVWGKGTTVTVSSG
    **:****:*****:************ ************ **. * ***** ******

D5  GGGSGGGGSGGGGSDIQMTQSPSTLSASIGDRVTITCRASEGIYHWLAWYQQKPGKAPKL
B11 GGGSGGGGSGGGGSDIQMTQSPSTLSASIGDRVTITCRASEGIYHWLAWYQQKPGKAPKL
    ************************************************************

D5  LIYKASSLASGAPSRFSGSGSGTDFTLTISSLQPDDFATYYCQQYSNYPLTFGGGTKLEI
B11 LIYKASSLASGAPSRFSGSGSGTDFTLTISSLQPDDFATYYCQQYSNYPLTFGGGTKLEI
    ************************************************************

D5  K
B11 K
    *
```

The present invention also relates to recombinant vectors and recombinant hosts, both prokaryotic and eukaryotic, which contain the nucleic acid molecules disclosed throughout this specification. The nucleic acid molecules of the present invention encoding a the heavy and/or light regions of D5/B11, in whole or in part, can be linked with other DNA molecules, i.e., DNA molecules which encompass immunoglobulin genes used for generation of a recombinant human antibody) that are not naturally linked, to form "recombinant DNA molecules" which encode a respective human recombinant antibody. The DNA sequences of the present invention can be inserted into vectors which comprise nucleic acids encoding D5, B11, or D5- or B11-like antibody binding regions, or functional equivalents thereof. These vectors may be comprised of DNA or RNA. For most cloning purposes DNA vectors are preferred. Typical vectors include plasmids, modified viruses, bacteriophage, cosmids, yeast artificial chromosomes, and other forms of episomal or integrated DNA. It is well within the purview of the skilled artisan to determine an appropriate vector for a particular gene transfer, generation of a recombinant human antibody or other use. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The antibody (such as an IgG recombinant human antibody) so produced may be harvested from the host cells in conventional ways. Therefore, the present invention also relates to methods of expressing the D5, B11, or D5- or B11-like antibody binding regions, or functional equivalents thereof, assays employing these gene products, recombinant host cells which comprise DNA constructs which express these proteins, and compounds identified through assays which utilize these components.

Any known expression vector may be utilized to practice this portion of the invention, including any vector containing a suitable promoter and other appropriate transcription regulatory elements. The resulting expression construct (containing the relevant DNA sequences encoding D5, B11, or D5- or B11-like antibody binding regions) are transferred into a prokaryotic or eukaryotic host cell to produce recombinant protein. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Techniques for such manipulations can be found described in Sambrook, et al. (1989, *Molecular Clon-* ing: *A Laboratory Manual*; Cold Spring Harbor Laboratory, Cold Spring Harbor, N.Y.) are well known and available to the artisan of ordinary skill in the art. Therefore, another aspect of the present invention includes host cells that have been engineered to contain and/or express DNA sequences encoding the D5, B11, or D5- or B11-like antibody binding region/specific binding member. Such an expression vector is cultured in a recombinant host cell under suitable conditions known in the art. Expression vectors may include, but are not limited to, cloning vectors, modified cloning vectors, specifically designed plasmids or viruses. Commercially available mammalian expression vectors which may be suitable, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565). Also, a variety of bacterial expression vectors are available, including but not limited to pCR2.1 (Invitrogen), pET11a (Novagen), lambda gt11 (Invitrogen), and pKK223-3 (Pharmacia). In addition, a variety of fungal cell expression vectors may be used, including but not limited to pYES2 (Invitrogen) and *Pichia* expression vector (Invitrogen). Also, a variety of insect cell expression vectors may be used, including but are not limited to pBlueBacIII and pBlueBacHis2 (Invitrogen), and pAcG2T (Pharringen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells. Mammalian species which may be suitable, include but are not limited to, L cells L-M(TK⁻) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K$^1$ (ATCC CCL 61), 3T3 (ATCC CCL 92), NIH/3T3 (ATCC CRL 1658), HeLa (ATCC CCL 2), C127I (ATCC CRL 1616), BS—C-1 (ATCC CCL 26), MRC-5 (ATCC CCL 171) and CPAE (ATCC CCL 209).

The present invention relates to methods of screening for and selecting HIV antiviral compounds, either in the form of a direct inhibitor of viral membrane fusion or possible in the form of a peptide vaccine which upon host administration stimulates a neutralizing antibody response. Such a methodology comprises utilizing a D5- or B11-like antibody/specific binding member and one or more known HR1 hydrophobic pocket-containing peptides in various antibody/peptide/test compound interaction assays in order to select a compound which acts as a HIV antiviral. The compound may be a peptide (e.g., as a potential prophylactic or therapeutic peptide vaccine), a protein, a non-proteinaceous organic or inorganic molecule, DNA (single or double stranded) or RNA (such as siRNA or shRNA). An antiviral compound identified by the methodology disclosed herein by nature will be a compound that actively competes D5/B11 for binding to the hydrophobic pocket of the HR1 region of gp41. A preferred antiviral compound selected by the methodology disclosed herein will be a compound which competes with a D5/B11 antibody at the like epitope. As discussed infra, peptide substrates, including but not limited to 5-Helix, IZN36, IQN36, IZN23, IQN23, IQN17 and IZN17 may be used but are not necessarily required in screening assays to select for such a HIV antiviral compound or peptide vaccine candidate (see Eckert and Kim, 2001, *Proc. Natl. Acad. Sci.* 98(20): 11187-11192 for relevant peptide sequences). It will become evident upon review of the disclosure and teachings of this specification that any such peptide or small molecule which effectively competes with D5/B11 antibodies for binding to this hydrophobic pocket of the N-helix trimeric coil structure of gp41 represents a possible HIV antiviral or vaccine lead. To this end, interaction assays may be utilized for the purpose of high throughput screening to identify compounds that occupy the hydrophobic pocket of HR1 and displace the antibody. The compounds may, in turn, represent HIV fusion inhibitors if they successfully prevent the intramolecular interaction of HR1 and HR2.

Various antibody/antigen-based assays known in the art may be used which incorporate and rely on a D5/B11 antibody of the present invention as an essential reagent in screening for a new HIV antiviral compound (e.g., a small inorganic molecule or candidate peptide vaccine), including but not limited to an ELISA assay, a RIA assays, a Western blot analysis, any homogenous assay relying on a detectable biological interaction not requiring separation or wash steps (e.g., see ALPHASCREEN™ from PERKINELMER® (Wellesley, MA)) and/or SPR-based technology (e.g., see BIACore). To this end, the present invention relates to any such assay, regardless of the known methodology employed, which measures the ability of a test compound to compete with D5/B11 to an appropriate peptide or protein mimetic of the hydrophobic pocket of the HR1 region of gp41. In addition to acting as an antiviral compound, epitope mapping and competitive binding assays have shown that D5 also functions as a probe for the conserved hydrophobic pocket observed in the crystal structure of the gp41mimetic IZN17 (Eckert, et al., 1999, *Cell* 99: 103-115). This property serves as the basis for a screening assay designed to detect small molecules that bind the hydrophobic pocket and thereby prevent D5 from binding to the pocket. For screening, one component (component 1) of the assay would consist of any peptide or protein bearing the gp41 pocket region, including but not limited to 5-helix, IZN36, IQN36, IZN23, IQN23, IQN17, or IZN17 (see Eckert et al, supra for respective amino acids sequences, as well as Eckert and Kim, 2001, *Proc. Nati. Acad. Sci.* 98(20): 11187-11192). These proteins and peptides could also be modified by covalent addition of a moiety to enable detection; such moieties include but are not limited to biotin. The other primary assay component (component 2) would include the specific binding site of the D5 MAb; such components could include, but not be limited to, the scFv form of D5, the Fab form of D5, the IgG form of D5, and bacteriophage bearing the D5 scFv as a fusion protein. To facilitate detection, this component could also be modified by covalent addition of moieties such as fluorescein, AlexaFluor647 (AlexaFluor647-NHS from Molecular Probes), or Europium chelates (e.g., Eu-LANCE-NHS from Wallac Perkin Elmer).

A screening assay designed to detect D5 binding to one of these partners would take any number of forms, of which only a few examples are presented herein for clarification, and not limitation. One mode would be a traditional enzyme-linked immunosorbent assay (ELISA) in which the biotin-labeled component is immobilized in a microtiter plate well coated with streptavidin, D5 IgG is allowed to react in the presence or absence of competitors, and antibody remaining bound (after washing) is detected using an enzyme-labeled anti-human IgG or an enzyme-labeled Protein A. A second format, discussed infra, uses ALPHASCREEN™ assay technology (PERKINELMER® (Wellesley, Mass.)) in which the donor bead is coated with Streptavidin and the acceptor bead is coated with Protein A. In this format, biotinylated component 1 is mixed with component 2 (D5 IgG in this case) in the presence or absence of competitor and allowed to react. After binding, complexes of component 1 and component 2 are detected by adding the donor and acceptor beads, waiting for binding, and measuring emitted light in a Fusion detector (Wallac Perkin Elmer) according to the manufacturer's instructions. A third format, also a homogeneous binding format, could rely on homogeneous time-resolved fluorescence (HTRF) technology. In this format, biotinylated component 1 is mixed, in the presence or absence of a competitor, with component 2 that has been covalently derivatized with AlexaFluor647. After binding, complexes of component 1 and component 2 are detected by adding Streptavidin (derivatized with Europium chelates, from Molecular Probes) and measuring fluorescence resonance energy transfer (FRET) in a microplate fluorometer according to the manufacturer's instructions. Alternatively, the HTRF assay could be done using component 2 derivatized with Europium chelate and Streptavidin derivatized with XL-665. Other assay technologies could also be applied to the application of detecting D5 bound to its partner.

One embodiment of the present invention relates to use of a homogenous assay involving the use of a biotinylated gp41 ectodomain peptide mimetic (including but not limited to 5-Helix, IZN36, IZN23, IQN36, IQN23, IQN17 and IZN17 or related scaffold-stabilized peptides which comprise at least a portion of the HR1 region of the ectodomain of gp41, and portions thereof which form stable gp41 mimetics) and a D5/B11 antibody in a high throughput competition assay with a large population of test compounds. This assay will quantitatively measure the ability of a specific test compound to compete with the known affinity between the peptide and the D5/B11 antibody. For example, in an ALPHASCREEN™-based homogenous indirect assay, biotinylated 5-helix peptide may be coupled to donor beads conjugated to streptavidin while the D5/B11 antibody is captured by Protein A or a secondary antibody (such as anti-human IgG antibody) coupled to acceptor beads. The coated bead complexes are mixed together in the presence of test compounds wherein each distinct test compound occupies a single well of a 96-well plate. The population of 96-well plates may then be incubated overnight in the dark at room temperature. The plates are then analyzed on a Fusion α-FP HT instrument, which excites the donor beads at 680 nm. A singlet oxygen is emitted by the donor beads and if the acceptor beads are in proximity, due to a peptide/antibody interaction, the singlet oxygen is captured by the acceptor beads, which emit light at 520-620 nm. The instrument records these emissions. When a respective test compound effectively competes with the D5/B 11 antibody for binding to the peptide, a decrease in signal is observed. In the absence of compound/antibody competition by a test compound, a maximal signal is detected.

Another available screening strategy which allows for incorporation of the antibodies of the present invention is the use surface plasmon resonance (SPR)-based biomolecular interaction analysis, such as with a BIACore 3000 instrument. Such an instrument provides several advantages over traditional immunoassays. First, use of SPR technology removes the need to use labeled reagents. Instead, an assay reagent is immobilized on a sensor chip (e.g., a streptavidin (SA) or carboxymethyldextran (CM5)), which are available from BIACore (Piscataway, N.J.). Second, formation of antibody/antigen/test compound complexes can be followed in real time, allowing for retrieval of information regarding reaction kinetics and affinity measurements (Kd). This technology is also amenable to analysis of test compounds, such as small organic molecules, to select a test compound which interacts with the epitope similar to a D5 or B11-like antibody. A biotinylated peptide (including but in no way limited to IZN17, IQN17, 5-Helix, IQN36, IZN36, IQN23 and/or IZN23) providing for a stable, faithful, mimetic of the gp41 fusion intermediate will be useful in BIACore-based screens of inhibitors targeting the N-helix of the HIV gp41 ectodomain will be useful in the assays of the present invention. These peptides can be immobilized by flowing a solution of 1 nM peptide in HBS (Hepes Buffered Saline) plus 10× Tween for 1-4 minutes over a SA chip. Manual injection is used until the bound peptide reaches 10 resonance units (RU), sufficient to bind 100 RU of analyte full antibody. Alternatively, a BIACore assay may be based upon immobilization of an antibody of the present invention on, preferably, a CM5 chip. Such as sensor chip if first surfaced activated by EDC (N-ethyl-N'-(3-dimethyl aminopropyl)-carbodiimide hydrochloride) and NHS(N-hydroxysuccinimide) following the manufacturer's instructions. Immobilization of a D5/B11-IgG may be carried out at 1-5 µg/mL in acetate buffer, pH 4.8 (mixing BIACore supplied buffers) using the inbuilt immobilization wizard control template, with target immobilization set at 1500-1800 RU. This will immobilize sufficient active D5-IgG to bind up to 100 RU of analyte peptide. Flow rates are normally 20 µl/min during association-dissociation phases, and 50 µl/min during surface regeneration with a single wash of 15 mM HCl. The kinetics wizard may be used to design the affinity measurement experiments, with duplicates and controls run as prompted to detect diffusion-limited kinetics. Analyte concentrations are chosen to give data for concentrations above and below the Kd value, with two-fold or four-fold dilution series. The association time is typically 3 min, dissociation 5-10 min while association-dissociation measurements are made at 25° C. in HBS+10×Tween, which should eliminate non-specific binding events. Analysis of data is by the BIACore curve-fitting software, selecting data from smooth regions with significant change in RU. It will be evident to the artisan that BIACore technology will allow for multiple assay formats in the context of a screen for HIV fusion inhibitors. A direct binding assay may be used where one or the other of either a D5/B11 antibody or a gp41 HR1 mimetic is immobilized to an appropriate sensor chip. With a chip containing immobilized D5/B11, either an assay which measures the direct binding of a test compound to D5/B11 or a surface competition assay measuring binding competition between a test compound and a gp41 mimetic of the epitope of interest in contemplated. Alternatively, a peptide such as, but again not limited to, 5-Helix, IZN17, IQN17, IQN36, IZN36, IQN23, and/or IZN23 may be immobilized on a sensor chip and used in either a direct binding assay to measure affinity of test compounds for the N-helix of the HIV gp41 ectodomain or in a surface competition assay with a test compound and a D5/B11 antibody. Compounds that compete with D5/B11 for association with the gp41 mimetic of choice will represent a candidate test compound for additional kinetic studies and/or animal studies.

Antiviral compounds and/or peptide vaccine candidates identified by D5/B11 antibody/protein or peptide mimetic/test compound may be detected by a variety of assays. The assay may be a simple "yes/no" assay to determine whether there is a change in the ability to form the known antibody/antigen complex. The assay is easily made quantitative by utilizing any number of assays, especially an ELISA-based assay, a homogenous assay, or an SPR-based assay. To this end, the present invention relates in part to methods of identifying an antiviral compound that occupies hydrophobic pocket of the HR1 coiled trimer, and displaces a D5/B11 antibody, thus preventing intramolecular interaction of the HR1 and HR2 regions of the gp41 ectodomain. Such methodology comprises (a) incubating a test compound along with (i) a D5/B11 antibody and (ii) a peptide or protein that mimics the hydrophobic pocket from the trimer coil-based HR1 region of the gp41 ectodomain; (b) measuring the effect the test compound has on the affinity of component (i) for component (ii); and (c) comparing that effect the test compound has on the affinity of component (i) for component (ii) versus the affinity of component (i) for component (ii) in the absence of the test compound. A decrease in component (i) and component (ii) affinity in the presence of the test compound, indicates that the test compound is a compound which interacts with and possesses a quantitative (i.e., measurable) affinity for the hydrophobic pocket of the gp41 BR1 region. Any such test compound is considered a potential HIV antiviral lead compound. Component (ii) may be any entity that at least substantially mimics the hydrophobic pocket of the trimer coiled HR1 region of the gp41 ectodomain, either in solution or immobilized on a substrate of choice. Again, examples of such entities at least include, but are not limited to, scaffold-based peptides which comprise at least portions of the gp41 sequence which span the gp41 ectodomain, such as 5-Helix, IZN17, IQN17, IQN36, IZN36, IZN23, IQN23, or portions thereof.

The various methodologies described herein which utilize either components and/or teachings of the present invention provide for possible identification of additional HIV neutralizing antibodies, an HIV antiviral compound and/or an HIV peptide-based vaccine. Methods for the selection of such additional products will allow for treatment of an HIV positive individual in a therapeutic treatment regime or for the prophylactic administration of a peptide-based vaccine identified through disclosed methodology. As noted supra, the present invention provides for several methodologies which may allow for identification of an HIV neutralizing antibody from a source other than an individual infected with HIV. It is disclosed herein the ability to use a synthetic antigen(s) to isolate a HIV neutralizing antibody. Both the products and the associated methodology of the present invention may allow for additional strategies regarding the development of an HIV vaccine, including but not necessarily limited to a method of identifying a neutralizing antibody; a method for identifying an HIV vaccine candidate(s) (including but not limited to small molecule inhibitors of viral membrane fusion and/or peptide vaccines). As an example, but not a limitation, the present invention further contemplates the use of D5- or B11-like antibodies in an antibody/peptide interaction assay involving a D5- or B11-like antibody and at least one HR1 hydrophobic pocket-containing peptide mimetic.

The present invention further relates to an antibody-based pharmaceutical composition comprising an effective amount D5, B11, a D5/B11-like antibody, or an affinity matured version which provides for a therapeutic treatment against HIV infection by reducing viral load levels within an infected individual, thus prolonging the asymptomatic phase of HIV infection. The antibody-based pharmaceutical composition of the present invention may be formulated by any number of strategies known in the art (e.g., see McGoff and Scher, 2000, *Solution Formulation of Proteins/Peptides*: In—McNally, E. J., ed. *Protein Formulation and Delivery*. New York, N.Y.: Marcel Dekker; pp. 139-158; Akers and Defilippis, 2000, *Peptides and Proteins as Parenteral Solutions*. In—*Pharmaceutical Formulation Development of Peptides and Proteins*. Philadelphia, Pa.: Talyor and Francis; pp. 145-177; Akers, et al., 2002, *Pharm. Biotechnol.* 14:47-127). A pharmaceutically acceptable composition suitable for patient administration will contain an effective amount of the antibody in a formulation which both retains biological activity while also promoting maximal stability during storage within an acceptable temperature range. This antibody-based pharmaceutical composition may optionally comprise a pharmaceutically acceptable carrier. Examples of such carriers are well known in the art and are described in a variety of texts, such as Remington's Pharmaceutical Sciences. The antibody formulation may be in liquid form or solid form. A solid formulation is generally lyophilized and brought into solution prior to administration for either single or multiple dosing. The formulations should not be exposed to extreme temperature or pH so as to avoid thermal denaturation. Thus, it is essential to formulate an antibody composition of the present invention within a biologically relevant pH range. A solution buffered to maintain a proper pH range during storage is indicated, especially for liquid formulations stored for longer periods of time between formulation and administration. To date, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. An effective range of total osmolarity (the total number of molecules in solution) is from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may contain from about 5% to about 25% sucrose, with a preferred range of sucrose from about 7% to about 15%, with an especially preferred sucrose concentration in a salt free formulation being from 10% to 12%. Alternatively, a salt free sorbitol-based formulation may contain sorbitol within a range from about 3% to about 12%, with a preferred range from about 4% to 7%, and an especially preferred range is from about 5% to about 6% sorbitol in a salt-free formulation. Salt-free formulations will of course warrant increased ranges of the respective cryoprotectant in order to maintain effective osmolarity levels. These formulation may also contain a divalent cation (including but not necessarily limited to $MgCl_2$, $CaCl_2$ and $MnCl_2$); and a nonionic surfactant (including but not necessarily limited to TWEEN 80® (polysorbate-80), TWEEN 60® (polysorbate-60), TWEEN 40® (polysorbate-40) and TWEEN 20® (polysorbate-20),(polyoxyethylene alkyl ethers, including but not limited to BRIJ®58 (polyoxyethylene (20) cetyl ether), BRIJ®35 (polyoxyethyleneglycol dodecyl ether), as well as others such as TRITON® X-100 (polyethylene glycol p-(1,1,3,3-tetramethylbutyl)-phenyl ether), TRITON® X-114 (polyethylene glycol tert-octylphenyl ether), NP40®

(nonyl phenoxylpolyethoxylethanol), Span 85 and the Pluronic series of non-ionic surfactants (e.g., Pluronic 121)). Any combination of such components, including probable inclusion of a bacteriostat, may be useful to fill the antibody-containing formulations of the present invention.

The antibody composition of the present invention may also be a "chemical derivative", which describes an antibody that contains additional chemical moieties which are not normally a part of the immunoglobulin molecule (e.g., pegylation). Such moieties may improve the solubility, half-life, absorption, etc. of the base molecule. Alternatively the moieties may attenuate undesirable side effects of the base molecule or decrease the toxicity of the base molecule. Examples of such moieties are again described in a variety of texts, such as Remington's Pharmaceutical Sciences.

The present invention also relates to at least (i) a therapeutic method for treating a HIV positive subject comprising the administration to the subject a composition which comprises a D5/B11-like antibody, and optionally one or more carriers, one or more excipients, and/or one or more chemical derivatives; (ii) a therapeutic method for treating a HIV positive subject comprising the administration to the subject a composition which comprises a HIV antiviral (including but not limited to an inorganic small molecule) selected by use of either the components and/or teachings of the present disclosure, optionally containing a pharmaceutically active carrier, wherein administration of the pharmaceutical composition results in a reduction of viral load within the patient; and, (iii) a prophylactic method for vaccinating a human subject against infection or progression of HIV which comprises administration of a peptide-based vaccine selected by use of either the components and/or teachings of the present disclosure, optionally containing a pharmaceutically active carrier, wherein administration of the pharmaceutical composition results in generation of an immune response against HIV infection. Administration of such a composition will be of result in a reduction in existing viral load (therapeutic) and thus prolonging the asymptomatic phase of the disease and/or by generating a substantial immune response (prophylactic) against HIV infection, namely generation of HIV neutralizing antibodies against the gp41 trimer region so as to prevent or substantially reduce the ability of HIV to fuse with a host cell. Such response may be documented by in vitro assays, in vivo non-human animal studies and/or further supported from human clinical trials. To this end, the present invention also relates further to a method of blocking fusion of the human immunodeficiency virus-1 to human cells and a method of preventing infection of human cells by HIV which comprises contacting HIV with an effective amount of a D5/B11-like antibody composition, such that the composition effectively blocks completion of 6-helical, pre-fusion gp41 structure which normally promotes fusion of the virus with the host cell. The compositions of the present invention may be administered to the host in any manner, strategy and/or combination available in the art in amounts sufficient to offer a therapeutic treatment against HIV infection by reducing viral load levels within an infected individual, thus prolonging the asymptomatic phase of HIV infection. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be utilized in a regimen which may include a monovalent or multivalent composition, various combined modality applications, and/or a prime/boost regimen to as to optimize, for example in a gene vaccination scenario, antigen expression and a concomitant cellular-mediated and/or humoral immune response. Therefore, these formulations may be administered as separate or multiple doses (i.e., administration of the antibody at staggered times by maintaining the sterile condition of the formulation through the treatment regime). The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular antibody thereof employed. A physician or veterinarian of ordinary skill can readily determine and prescribe the effective therapeutic amount of the antibody. Optimal precision in achieving concentrations of antibody within the range that yields efficacy without toxicity requires a regimen based on the kinetics of the drug's availability to target sites. This involves a consideration of the distribution, equilibrium, and elimination of a drug. Antibodies described herein may be used alone at appropriate dosages. Alternatively, co-administration or sequential administration of other agents may be desirable. It will be possible to present a therapeutic dosing regime for the antibodies of the present invention in conjunction with alternative antiviral or HIV vaccine administration regimes. The antiviral agent preferably is an antiviral agent that directly targets HIV at an alternate source away from gp41, such as a protease inhibitor, an inhibitor of reverse transcriptase, an integrase inhibitor, host cell receptor (CD40) or co-receptors (CXCR4 or CCR5), and/or gp120. The antiviral agent may be administered to the individual in some combination of effective antiviral therapeutics such as that present in highly active anti-retroviral therapy ("HAART"). The term "HAART" is generally used in the art to refer to a cocktail of 3 or more antiviral drugs, including but not limited to combinations of inhibitors of viral protease and reverse transcriptase. A dosing regime may also be contemplated for the antibody composition of the present invention during a similar time frame as administration of an DNA-, protein-, or peptide-based HIV vaccine (e.g., such as a peptide vaccine identified through a screening assay utilizing the D5/B11 components of the present invention) within a therapeutic window in an attempt to reduce the patient's viral load. Such a vaccine may be administered within a similar time frame as any antibody-based treatment plan, with either a single vaccine administration or within the confines of a prime/boost-type vaccine regimen. The priming dose effectively primes the immune response so that, upon subsequent identification of the antigen(s) in the circulating immune system, the immune response is capable of immediately recognizing and responding to the antigen(s) within the host. Preferably, the vaccine priming and boosting administrations are different in order to evade any host immunity directed against the first delivered vaccine, especially if that vaccine is delivered as part of a 'non-self' recombinant vehicle, such as a recombinant non-viral (e.g., plasmid) or viral (e.g., adenovirus, AAV, etc.) vehicle. Such a mixed modality prime and boost inoculation scheme may will result in an enhanced immune response. Prime-boost administrations typically involve priming the subject (by viral vector, plasmid, protein, peptide, antibody, etc.) at least one time, allowing a predetermined length of time to pass, and then boosting (by viral vector, plasmid, protein, peptide, antibody, etc.). Multiple primings, typically 1-4, are usually employed, although more may be used. The length of time between priming and boost may typically vary from about four months to a year, albeit other time frames may be used as one of ordinary skill in the art will appreciate. The follow-up or boosting administration may as well be repeated at selected time intervals. In other words, DNA- or protein-vaccine prime/boost regimes are now commonplace in HIV vaccine strategies and may be integrated with a treatment regimen utilizing a therapeutic antibody of the present invention. The artisan may incorporate therapeutic capabilities of the present invention into now commonplace prophylactic-based prime-boost regimes for the treatment of HIV. Alternatively, the core components of the present invention allow for, as discussed supra, assays to identify peptide vaccine candidates. Such a peptide vaccine identified utilizing these core components may be inserted into a therapeutic regime in combination with a D5/B1-like antibody or alone as a prophylactic-based peptide vaccine. Any potential hosts/vaccinees/individuals include but are not limited to primates and especially humans and non-human primates, and include any non-human mammal of commercial or domestic veterinary importance.

The following examples are provided to illustrate the present invention without, however, limiting the same hereto.

EXAMPLE 1

Isolation and Characterization of ScFvs D5 and B11

Clones 5H/I1-BMV-D5 and 5H/I1-BMV-B11 were isolated from scFv libraries by selection on 5-Helix and IZN36 peptides. The terms "5H" and "5-Helix" are used interchangeably throughout this application. Also, the terms "I1" and "IZN36" are used interchangeably throughout this application. An scFv phagemid library, which is an expanded version of the $1.38 \times 10^{10}$ library described by Vaughan et al., (Vaughan et al., 1996, Nature Biotech. 14: 309-314) was used to select antibodies specific for peptides representing HIV gp41 structures.

First Round scFv Panning Selection—The biotinylated 5 Helix (5H) peptide (SEQ ID NO: 13; 0.27 mg/ml) was diluted to 10 µg/ml in phosphate buffered saline solution, pH 7.2 (PBS) and a volume of 100 µl was coated on to a well of an Abgene streptavidin plate (Cat No. AB-0509) and incubated for two hours at room temperature (RT). After incubation, the plate washed once with PBS. The antigen coated wells were blocked by addition of 300 µl of a 3% (w/v) 'Marvel' skimmed milk powder suspension in phosphate buffered saline (MPBS) and incubation at room temperature for 1 hour. Purified scFv phage ($10^{12}$ transducing units (tu)) were blocked in 100 µl 3% 'Marvel' skimmed milk powder in phosphate buffered saline (MPBS) for 15 minutes at room temperature before being added to the antigen wells, which had been washed once with PBS. The phage were incubated on the coated antigen well for 1 hour at room temperature. Irrelevant phage were washed off and the specific-binding phage eluted as described by Vaughan et al., supra. The eluted phage were used to infect 5 ml exponentially growing E. coli TG-1 cells. Cells and phage were incubated for 1 hour at 37° C. (30 minutes stationary, 30 minutes shaking at 250 rpm), then spread on 2TYAG. All the titer and bioassay plates were incubated overnight at 30° C. Output colonies were scraped off the plates into 10 ml 2TY broth and 15% glycerol added for storage at –70° C. Glycerol stock cultures from the first round panning selection were super infected with helper phage and rescued to give scFv antibody-expressing phage particles for the second round of selection (Vaughan et al., 1996, Nature Biotech.: 14: 309-314).

Second Round scFv Soluble Selection—Soluble selections were carried out using biotinylated IZN36 (SEQ ID NO:14) in 1 µM stock solution in 150 mM sodium chloride, 50 mM sodium phosphate, pH 7.4). Bio-IZN36 was used at a concentration of 250 nM. A rescued scFv-phage output, as described above, was used. Overnight bacterial growths containing rescued phagemid outputs from the first round of selection were centrifuged at 300 rpm in a Stovall RT7 benchtop centrifuge for 10 minutes at room temperature. The supernatant, (containing output phage) were blocked with an equal volume of 6% (w/v) Marvel dried skimmed milk powder in 2× concentrated PBS. Additionally, IZN36 scaffold peptide (10 µM stock in PBS) was added to a concentration of 20 µg/ml to act as a sink for phage expressing scFv specific for the scaffold protein, rather than the gp41 portion of IZN36. The blocked phage were incubated for 30 minutes at room temperature, then biotinylated antigen (IZN36) was added and incubated at room temperature for a further 1 hour. Phage/antigen was added to 50 µl of Dylan M280 Streptavidin magnetic beads (previously blocked for 1 hour at 37° C. in 1 ml of 3% MPBS) and incubated for a further 15 minutes at room temperature, with gentle agitation. Beads were captured using a magnetic rack and washed 4× in 1 ml of 3% MPBS/ 0.1% (v/v) Tween 20 followed by three washes in PBS. After the last PBS wash, beads were resuspended in 100 µl PBS and used to infect 5 mil exponentially growing E. coli TG-1 cells. Cells and phage were incubated for 1 hour at 37° C. (30 minutes stationary, 30 minutes shaking at 250 rpm), then spread on 2TYAG plates. Plates were incubated at 30° C. overnight and colonies visualized the next day. Output colonies were scraped off into 10 ml 2TY broth and 15% glycerol added for storage at –70° C. Additionally, colonies were picked from output plates and were analyzed by specificity phage ELISA.

Specificity phage ELISA—To determine the specificity of antibodies isolated from the selections, a phage ELISA was performed against biotinylated 5H, biotinylated IZN36 and irrelevant peptide (biotinylated IZN36 scaffold). Individual E. coli colonies containing phagemid were inoculated into 96 well plates containing 100 µl 12TYAG medium per well and were incubated at 37° C., shaking at 250 rpm until exponential growth phase (taken to be when the optical density of the culture measured at 600 nm ($OD_{600}$)=0.5). M13K07 helper phage were added to a multiplicity of infection (moi) of 10 to the exponentially growing culture and the plates incubated a further 1 hour at 37° C. Plates were centrifuged in a benchtop centrifuge at 2000 rpm for 10 minutes. The supernatant was removed and cell pellets were resuspended in 100 µl 2TYAK and incubated at 30° C. overnight with shaking at 250 rpm. The next day, plates were centrifuged at 2000 rpm for 10 minutes and 100 µl phage-containing supernatant from each well transferred to a fresh 96 well plate. Phage samples were blocked in a final concentration of 3% MPBS for 30 minutes at room temperature, prior to ELISA.

Figure 1:
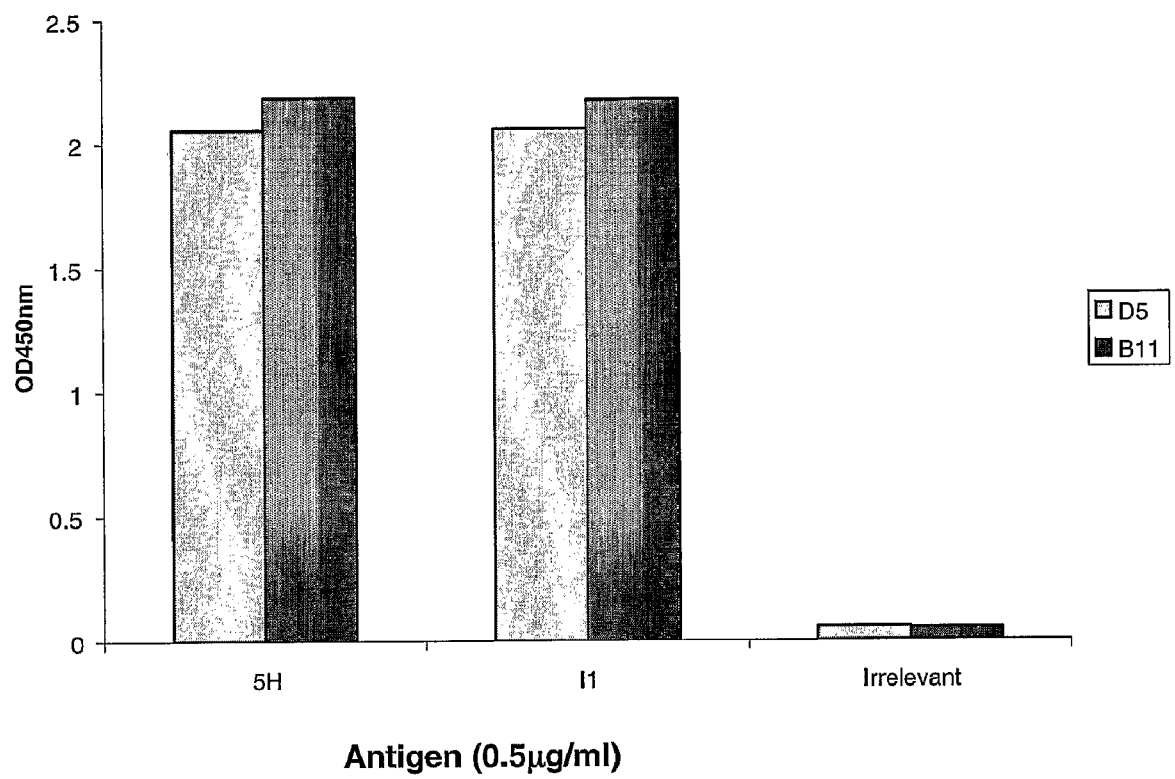
FIG. 1 shows the cross-specificity of scFv isolated 5H/I1-BMV-D5 ("D5") and 5H/I1-BMV-B11 ("B11"). The "irrelevant" antigen is the IZN scaffold alone from the IZN36 peptide mimetic.

One hundred microliters of biotinylated 5-Helix, biotinylated IZN36 (as described supra) or biotinylated I scaffold (as described supra; all at 2 µg/ml in PBS) were coated onto 96-well Abgene streptavidin plates (Cat No. AB-0509) for 1 hour, at room temperature. After coating, the wells were washed once in PBS and the plates blocked for 1 hour at room temperature in 3% MPBS. Plates were rinsed with PBS then 50 µl of pre-blocked phage added to each well. The plates were incubated at room temperature for 1 hour and then washed with 3 changes of PBS containing 0.1% (v/v) Tween 20 (PBST) followed by 3 changes of PBS. To each well, 50 µl of a 1:5000 dilution (in MPBS) of anti-M13-HRP conjugate (Pharmacia) was added and the plates incubated at room temperature for 1 hour. Each plate washed three times with PBST then three times with PBS. Fifty microliters of TMB substrate (Sigma, catalogue number T0440) was added to each well and incubated until color development. The reaction was stopped by the addition of 25 µl of 0.5 M H₂SO₄. The signal generated was measured by reading the absorbance at 450 nm using a microtiter plate reader. Cross-specific binding to 5-Helix and IZN36 was confirmed in this way and is shown in FIG. 1.

Sequencing of 5-Helix/IZN36-cross-specific scFv-5-Helix/IZN36-cross-specific scFv E. coli clones were streaked out onto 2TYAG plates and incubated overnight at 30° C. Triplicate colonies from these plates were sequenced using pCANTAB6 vector sequence oligos to amplify the VI, and V$_L$ regions from the scFv clone. The nucleotide and corresponding amino acid sequences for D5 and B11 are shown in various configurations in FIG. 2A-F (D5), FIG. 3A-F (B11), and FIG. 4 (comparison of scFv D5 and B11 amino acid sequences).

EXAMPLE 2

Conversion of D5 scFv to IgG4

Heavy and light chain V regions from a D5 scFv clone was amplified using PCR and clone-specific primers. PCR products were digested with appropriate restriction enzymes and subcloned into a vector containing human IgG4 heavy chain constant domain (plasmid pEU8.2) for the V$_H$ domain or a vector containing human kappa light chain constant domain (plasmid pEU3.2) for the V$_L$ domain of D5. Correct insertion of the respective D5 V$_H$, and V$_L$ region domains into plasmids was verified by sequencing of plasmid DNA from individual E. coli colonies. Plasmids were then prepared from E. coli cultures by standard techniques and heavy and light chain constructs co-transfected into human embryonic kidney (HEK-293) cells using standard techniques. Secreted IgG4 was purified using protein A sepharose (Pharmacia) and buffer exchanged into PBS. Similar protocols are described in Example section 2 for conversion of the B11 scFv to IgG1, but for clarity are presented in both Example sections. The D5 scFv DNA sequence is as follows:

PCR amplification of D5 scFv V$_H$ and V$_L$ regions—Bacterial colonies containing scFv D5 were inoculated in 2YTA medium into the wells of a microtiter plate and grown overnight at 30° C., 120 rpm. PCR reactions contained 2× PCR mastermix (Abgene) and 10 µM of both the forward and reverse primers. V$_H$ and V$_L$ primers were as follows:

V$_H$-5', primer AF18

(SEQ ID NO: 15)

```
5'-CTCTCCACAGGCGCGCACTCCCAGGT (GC) CAGCTGGTGCA
            BssH II
```

V$_H$-3', primer Hlink (SEQ ID NO: 16)

```
5'-ACCGCCAGAGCCACCTCCGCC
```

V$_L$-5', primer AF7

(SEQ ID NO: 17)

```
5'-GATCGATGGTGTGCACTCGGACATCCAGATGACCCAGTCT
            ApaL I
```

V$_L$-3', primer AF24':

(SEQ ID NO: 18)

```
5'-CTATTCCTTAATTAAGTTAGATCTATTCTACTCACGTTTGATCTCCA
            Pac I
GCTTGTCCCTCC
```

The forward and reverse primers carry the respective restriction sites for cloning into the respective IgG4 conversion vector. PCR reactions were run at 94° C. for 2 min, followed by 94° C. for 1 min., 55° C. for 1 min., 72° C. for 1 min. (30 cycles); followed by a final hold at 72° C. for 5 min.

(SEQ ID NO: 1)
```
CAGGTGCAGC TGGTGCAGTC TGGGGCTGAG GTGAGGAAGC CTGGGGCCTC AGTGAAGGTC

TCCTGCAAGG CTTCTGGAGA CACCTTCAGC AGCTATGCTA TCAGCTGGGT GCGACAGGCC

CCTGGACAAG GGCTTGAGTG GATGGGAGGG ATCATCCCTA TTTTTGGTAC AGCAAACTAC

GCACAGAAGT TCCAGGGCAG AGTCACGATT ACCGCGGACG AATCCACGAG TACAGCCTAC

ATGGAGCTGA GCAGCCTGAG ATCTGAAGAC ACGGCCATTT ATTACTGCGC GAGAGATAAC

CCGACACTAC TCGGCTCTGA CTACTGCGGC AAGGGAACCC TGGTCACCGT CTCGAGTGGT

GGAGGCGGTT CAGGCGGAGG TGGCAGCGGC GGTGGCGGAT CGGACATCCA GATGACCCAG

TCTCCTTCCA CCCTGTCTGC ATCTATTGGA GACAGAGTCA CCATCACCTG CCGGGCCAGT

GAGGGTATTT ATCACTGGTT GGCCTGGTAT CAGCAGAAGC CAGGGAAAGC CCCTAAACTC

CTGATCTATA AGGCCTCTAG TTTAGCCAGT GGGGCCCCAT CAAGGTTCAG CGGCAGTGGA

TCTGGGACAG ATTTCACTCT CACCATCAGC AGCCTGCAGC CTGATGATTT TGCAACTTAT

TACTGCCAAC AATATAGTAA TTATCCGCTC ACTTTCGGCG GAGGGACCAA GCTGGAGATC

AAA
```

PCR-amplified V$_H$ is as follows:

(SEQ ID NO: 19)
```
          BssH II
CTCTCCACAG GCGCGCACTC CCAGGTGCAG CTGGTGCAGT CTGGGGCTGA GGTGAGGAAG

CCTGGGGCCT CAGTGAAGGT CTCCTGCAAG GCTTCTGGAG ACACCTTCAG CAGCTATGCT

ATCAGCTGGG TGCGACAGGC CCCTCGACAA GGCCTTGAGT GGATGGGAGG GATCATCCCT

ATTTTTGGTA CAGCAAACTA CGCACAGAAG TTCCAGGGCA GAGTCACGAT TACCGCGGAC

GAATCCACGA GTACAGCCTA CATGGAGCTG AGCAGCCTGA GATCTGAAGA CACGGCCATT

TATTACTGCG CCAGAGATAA CCCGACACTA CTCGGCTCTG ACTACTCGGG CAACGGAACC

CTGGTCACCG TCTCGAGTGG TGGAGGCGGT TCAGGCGGAG GTGGCTCTGG CGGT
   GGTCACCG
     BstE II
```

PCR-amplified V$_L$ is as follows:

(SEQ ID NO: 20)
```
          ApaL I
GATCGATGGT GTGCACTCGG ACATCCAGAT GACCCAGTCT CCTTCCACCC TGTCTGCATC

TATTGGAGAC AGAGTCACCA TCACCTGCCG GGCCAGTGAG GGTATTTATC ACTGGTTGGC

CTGGTATCAG CAGAACCCAG GGAAAGCCCC TAAACTCCTG ATCTATAAGG CCTCTAGTTT

AGCCAGTGGG GCCCCATCAA GGTTCAGCGG CAGTGGATCT GGGACAGATT TCACTCTCAC

CATGAGCAGC CTGCAGCCTG ATGATTTTGC AACTTATTAC TGCCAACAAT ATAGTAATTA

TCCGCTCACT TTCGCCGGAG GGACCAAGCT GGAGATCAAA CGTGACTAGA ATAGATCTAA

CTTAATTAAG GAATAG.
   Pac I
```

Vector pEU8.2 (IgG4) was used for D5 V$_H$ and pEU3.2 (kappa) for D5 V$_L$ (see discussion infra). Primer PECSEQ1 and 8.2 rev were used for PCR and sequence confirmation of V$_H$ clones. Primer P168 and P362 for PCR and sequence confirmation of V$_L$ clones. V$_H$ (BssHII and BstEII) and V$_L$ (ApaLI and PacI) PCR products were subjected to restriction endonulcease digestion to promote subcloning into pEU8.2 and pEU3.2, respectively.

PECSEQ1
5'-GCAGGCTTGAGGTCTGGAC   (SEQ ID NO: 21)

-continued 8.2Reverse
5'-CCAGGGGGAAGACCGATG   (SEQ ID NO: 22)

P168
5'-CTTGAGGTCTGGACATATATATGGGTGACAATG   (SEQ ID NO: 23)

p362
5'-TCCTGGGAGTTACCCGATTCGAGGGCGTTA   (SEQ ID NO: 24)

The clone selected for transfection encodes the D5 V$_H$ amino acid sequence as follows:

(SEQ ID NO: 4)
QVQLVQSGAE VRKPGASVKV SCKASGDTFS SYAISWVRQA PCQGLEWNGG IIPIFGTANY

AQKFQGRVTI TADESTSTAY MELSSLRSED TAIYYCARDN PTLLGSDYWG KGTLVTVSS.

The clone selected for transfection encodes the D5 V$_L$ amino acid sequence as follows:

(SEQ ID NO: 6)
DIQMTQSPST LSASIGDRVT ITCRASEGIY HWLAWYQQKP GKAPKLLIYK ASSLASGAPS

RFSGSGSGTD FTLTISSLQP DDFATYYCQQ YSNYPLTFGG GTKLEIK.

Table 3 shows the alignment of the nucleotide and amino acid sequence of the D5 scFv.

TABLE 3

```
D5  CAGGTGCAGCTGGTGCAGTCTGGGGCTGAGGTGAGGAAGCCTGGGGCCTCAGTGAAGGTC
     Q  V  Q  L  V  Q  S  G  A  E  V  R  K  P  G  A  S  V  K  V

D5  TCCTGCAAGGCTTCTGGAGACACCTTCAGCAGCTATGCTATCAGCTGGGTGCGACAGGCC
     S  C  K  A  S  G  D  T  F  S  S  Y  A  I  S  W  V  R  Q  A

D5  CCTGGACAAGGGCTTGAGTGGATGGGAGGGATCATCCCTATTTTTGGTACAGCAAACTAC
     P  G  Q  G  L  E  W  M  G  G  I  I  P  I  F  G  T  A  N  Y

D5  GCACAGAAGTTCCAGGGCAGAGTCACGATTACCGCGGACGAATCCACGAGTACAGCCTAC
     A  Q  K  F  Q  G  R  V  T  I  T  A  D  E  S  T  S  T  A  Y

D5  ATGGAGCTGAGCAGCCTGAGATCTGAAGACACGGCCATTTATTACTGCGCGAGAGATAAC
     M  E  L  S  S  L  R  S  E  D  T  A  I  Y  Y  C  A  R  D  N

D5  CCGACACTACTCGGCTCTGACTACTGGGGCAAGGGAACCCTGGTCACCGTCTCGAGTGGT
     P  T  L  L  G  S  D  Y  W  G  K  G  T  L  V  T  V  S  S  0

D5  GGAGGCGGTTCAGGCGGAGGTGGCAGCGGCGGTGGCGGATCGGACATCCAGATGACCCAG
     G  G  G  S  G  G  G  S  G  G  G  S  D  I  Q  M  T  Q

D5  TCTCCTTCCACCCTGTCTGCATCTATTGGAGACAGAGTCACCATCACCTGCCGGGCCAGT
     S  P  S  T  L  S  A  S  I  G  D  R  V  T  I  T  C  R  A  S

D5  GAGGGTATTTATCACTGGTTGGCCTGGTATCAGCAGAAGCCAGGGAAAGCCCCTAAACTC
     E  G  I  Y  H  W  L  A  W  Y  Q  Q  K  P  G  K  A  P  K  L

D5  CTGATCTATAAGGCCTCTAGTTTAGCCAGTGGGGCCCCATCAAGGTTCAGCGGCAGTGGA
     L  I  Y  K  A  S  S  L  A  S  G  A  P  S  R  F  S  G  S  G

D5  TCTGGGACAGATTTCACTCTCACCATCAGCAGCCTGCAGCCTGATGATTTTGCAACTTAT
     S  G  T  D  F  T  L  T  I  S  S  L  Q  P  D  D  F  A  T  Y

D5  TACTGCCAACAATATAGTAATTATCCGCTCACTTTCGGCGGAGGGACCAAGCTGGAGATC
     Y  C  Q  Q  Y  S  N  Y  P  L  T  F  G  G  G  T  K  L  E  I

D5  AAA  (SEQ ID NO: 1)
     K   (SEQ ID NO: 2)
```

Restriction digested DNA was purified using a QIAquick Nucleotide Removal Kit (Qiagen). The $V_H$- and $V_L$-restriction digestion PCR products were ligated into inserted into pEU8.2 (IgG4 heavy chain; see FIG. 5A (vector) and FIG. 5B (nucleotide sequence)) for D5 $V_H$ and pEU3.2 (kappa light chain; see FIG. 6A (vector) and FIG. 6B (nucleotide sequence)) for D5 $V_L$. Plasmid pEU8.2 is a 9.3 kB mammalian expression plasmid vector developed by CAT (FIG. 5A) which contains a human gamma 4 heavy chain expression cassette and a neo (G418R) selectable marker for mammalian cells and ampicillin resistant marker for E. coli cells. The completed gamma 4 heavy chain vector (i.e., with a $V_H$ region such as D5 $V_H$) can be co-transfected with a light chain gene plasmid into a mammalian cell line such as HBEK-BENA or COS cells for transient expression of IgG. The $V_H$ PCR product is cloned as a BssHII-BstEII fragment into polylinker between the secretory leader and gamma 1 constant region sequences. The secretory leader sequence, MGWSCII-FLVATATGAHS (SEQ ID NO:25), is derived from a mouse heavy chain sequence while transcription is driven from the EF-1α promoter and terminated by the SV40 termination/poly A sequence. The Epstein Barr virus origin of replication is upstream of the EF-1a promoter. The oriP sequence enhances level of transient expression from human embryonic kidney 293-EBNA cells. Each ligation reaction was transfected into E. coli DH5α cells and plated on appropriate media/selectable marker. Plasmid pEU3.2 (FIG. 6A) contains an expression cassette for human kappa light chains and ampicillin resistant marker for E. coli cells. The $V_L$ PCR product is cloned as a ApaLI-PacI fragment into polylinker between the secretory leader and the human kappa constant domain sequences. Plasmid pEU3.2 contains a secretory leader peptide from a mouse heavy chain sequence transcription is driven from the EF-1a promoter and terminated by the human kappa light chain gene/ploy A sequence. Plasmid pEU3.2 also contains the Epstein Barr virus origin of replication upstream of the EF-1α promoter as well as the oriP sequence. The kappa light chain vector can be co-transfected with a heavy chain gene plasmid into HEK-BENA or COS cells for transient expression of IgG.

Growth and preparation of HEK-EBNA cells for transfection—HEK-EBNA stock cells are maintained in Dulbecco's Modified Eagle Medium (DMEM) containing 10% fetal bovine serum (v/v), 10% DMSO (v/v). Three to 4 days prior to transfection, stock culture cells are plated in Dulbecco's Modified Eagle Medium (GIBCO) containing 10% fetal bovine serum, 4 mM glutamine, 1× non essential amino acids, 1× penicillin/streptomycin. On the day before transfection, cells are split in 75 ml of Dulbecco's Modified Eagle Medium containing 10% fetal bovine serum, 4 mM glutamine, 1× non essential amino acids, 1× penicillin/streptomycin with cell numbers of 7-9×10⁶ in a T150 tissue culture flask. After 1 day growth, cells are 60% confluent and therefore suitable for transfection. The culture is inoculated with the $V_H$- or $V_L$-containing clone in 100 ml of 2×YT medium with 50 μg/ml of Ampicillin. The culture is grown overnight at 37° C. at 280 rpm. After incubation, a 1 ml sample of the culture is added to 1 ml of 40% glycerol and stored at −80° C. Plasmid DNA is extracted from the remainder of the overnight culture using a QIAgen Maxiprep kit according to the manufacturer's instructions. Plasmid DNA is re-dissolved in 100 µl of water and the concentration of DNA determined by absorbance at 260 nm. Forty micrograms of each plasmid DNA is diluted in DMEM (no serum) to a total volume of 1.5 ml in a 15 ml Falcon tissue culture tube. The tube is mixed and 400 µl of PolyFect Transfection Reagent (Qiagen) is added to the DNA solution, vortexed for 10 seconds and incubated for 15 min at RT. Fifty five ml of Dulbecco's Modified Eagle Medium containing 10% fetal bovine serum, 4 mM glutamine, 1× non essential amino acids, 1× penicillin/streptomycin are added to the cell culture. Five ml of cell growth medium is added to the reaction tube containing the transfection complexes, which are mixed and the total volume immediately transferred to cell culture. After overnight incubation, the medium is removed and replaced with 75 ml of OPTI-MEM1 (Reduced Serum Medium-GIBCO). Immediately prior to transfection, the medium is replaced with 20 ml of fresh DMEM containing 2% fetal bovine serum and 1× penicillin/streptomycin. One thousand millileters of filter sterilized 2×HEPES buffered saline (2×HBS) is warmed in a 37° C. water bath. One hundred microliters of $CaCl_2$ (2.5 M) is added to 100 µl of DNA mixture which contains 50 µg of each plasmid in a 15 ml Falcon tissue culture tube. The pre-warmed DNA mixture is added to IBS drop wise while mixing on a vortex mixer and incubated for 2-5 min at 37° C. The HBS/DNA solution is added to the HEK-EBNA cells and incubated overnight, followed by replacement of the medium with 25 ml of fresh CD-CHO medium containing 8 mM glutamine, 1× penicillin/streptomycin supplement, 1× hypoxanthine/thymidine supplement.

Culture of transfected cells and harvesting of IgG—The cells are incubated overnight at 37° C., 5% $CO_2$ concentration, with humidification. The medium is harvested, filter sterilized and stored at 4° C. The culture is replaced with fresh medium and harvesting was continued at 2-3 day intervals for up to 12 days, each time filter sterilizing the harvested medium and pooling with previously harvested medium from the culture.

Capture ELISA for IgG—Initial analysis of IgG4 concentration in the culture medium is carried out using capture ELISA, which monitors the success of the transfection through an approximation of the concentration of IgG present in the harvested medium. Fragment goat anti-human IgG (H+L) (Jackson ImmunoReseach Lab) is diluted to 10 µg/ml with 50 mM Tris, pH 9.5. Each well of a Nunc Immunosorb plate (NUNC) is coated with 100 µl of diluted capture antibody. The plate is sealed, incubated overnight at 4° C., washed three times with PBS/Tween 20 [0.5% (v/v)], three times with PBS and blotted dry with paper towels. The wells are then blocked with 150 µl of PBS/3% powdered milk per well for 1 h at 37° C. Plates are then washed three 3 times with PBS/Tween 20, three times with PBS and blotted dry. One hundred microliters of PBS/3% powdered milk is added to all wells except for A1, B1, A12 and B12. An appropriate standard antibody (hu IgG-Sigma) was diluted in PBS/3% powdered milk to a final concentration of 2.5 µg/ml and 200 µl of the standard Ab is added to A1 and B1 mix by pipetting and transferring 100 pt of the antibody from A1 to A2 and B1 to B2. This dilution step is repeated down to A10 and B10. One hundred microliters of the antibody dilution from is removed and discarded from wells A10 and BIO to ensure equal volumes in the wells, resulting in a 1 in 2 serial dilution of antibody standard (2.5 µg/ml ~0 05 µg/ml) in rows A and B up to column 10. One hundred microliters of filtered culture medium containing IgG is diluted in 400 µl PBS/3% powdered milk. One hundred microliters is added to duplicate wells on adjacent column 1, mixed by pipetting and 100 µl transferred to the next column (e.g. C2 and D2) and 1 in 2 serial dilutions were continued down each column. One hundred microliters is discarded from column 12 to ensure equal volumes in the wells. One hundred microliters of un-inoculated medium is added to wells A12 and B12 as medium (negative) controls. The plate is incubated at 37° C. for 2 h, washed five times with PBS/Tween 20 and five times with PBS, and blotted dry with paper towels. Appropriate amounts of horseradish peroxidase (HRP) conjugated detection antibody (Goat anti human IgG, FC specific-Sigma) are diluted in PBS/3% powdered milk (1 in 10000 dilutions) and 100 µl of the diluted detection antibody was added to each well, incubated at 37° C. for 1 h, washed five times with PBS/Tween 20 and five times with PBS, and blotted dry with paper towels. Finally, 100 µl of 3,3',5,5'-tetramethylbenzidine (TMB) is added to each well and incubated at RT until color developed (approximately 1-5 rain). Fifty microliters of 0.5 M sulphuric acid is added to stop the color reaction and the plates were read at 450 nm.

Purification of IgGs from harvested supernatant using protein A sepharose—A Protein A sepharose (Amersham) column (1 ml for 1 L of cell supernatant) is pre-equilibrated in 20 ml of buffer PBS, 0.02% Tween 20 prior to addition of the samples. Harvested supernatant is loaded onto the column using a peristatic pump at 4° C., with the flow rate not allowed to exceed 3 ml $min^{-1}$. The unbound fraction is reloaded 2 additional times prior to washing the column with 100 column volumes of buffer PBS, 0.02% Tween 20. The antibody is eluted by using 5 ml of 0.1M glycine pH 2.8 and collected directly into 0.5 ml of 2M Tris pH 8.0. The eluting step is repeated three times, the column washed with 20 ml of 0.1M glycine pH 2.8 and 100 ml of buffer PBS, 0.02% Tween 20. The eluted fractions are analyzed by SDS PAGE, and then buffer exchanged and concentrated by using Amicon Ultra 15 (MILLIPORE). The sample is quantitated by ELISA or OD280 where 1.34 mg per ml gives an absorbance of 1.0. Purification is completed at ambient temp, while reagent vessels and fractions kept on ice and samples subsequently stored and −20° C.

EXAMPLE 3

Conversion of B11 scFv to IgG1

The B11 scFv DNA sequence is as follows:

(SEQ ID NO: 7)
```
CAGGTGCAGC TGGTGCAATC TGGGGCTGAG GTGAAGAAGC CTGGGTCCTC GGTGAAGGTC

TCCTGCAAGG CTTCTGGAGG CACCTTCAGC AGCTATGCTA TCAGCTGGGT GCGACAGGCC

CCTGGACAAG GGCTTGAGTG GATGGGAGGG ATCATCCCTC TCTTTGATAC ATCAAACTAC

GCACAGAACT TCCAGGGCAG AATCACGATA ACTGCGGACA AATCCACGAG TACAGCCTAC
```

-continued

```
ATGGAACTGA GCAGCCTGAG ATTTGAGGAC ACGGCCATTT ATTACTGTGC GAGAGATAAC

CCTTTACTTC TCGCTATGGA TGTCTGGGGG AAAGGGACCA CGGTCACCGT CTCGAGTGGT

GGAGGCGGTT CAGGCGGAGG TGGCAGCGGC GGTGGCGGAT CGGACATCCA GATGACCCAG

TCTCCTTCCA CCCTGTCTGC ATCTATTGGA GACAGAGTCA CCATCACCTG CCGGGCCAGT

GAGGGTATTT ATCACTGGTT GGCCTGGTAT CAGCAGAAGC CAGGGAAAGC CCCTAAACTC

CTGATCTATA AGGCCTCTAG TTTAGCCAGT GGGGCCCCAT CAAGGTTCAG CGGCAGTGGA

TCTGGGACAG ATTTCACTCT CACCATCAGC AGCCTGCAGC CTGATGATTT TGCAACTTAT

TACTGCCAAC AATATAGTAA TTATCCGCTC ACTTTCGGCG GAGGGACCAA GCTGGAGATC

AAA.
```

PCR amplification of B11 scFv $V_H$ and $V_L$ regions—Bacterial colonies containing scFv B11 were inoculated in 2YTA medium into the wells of a microliter plate and grown overnight at 30° C., 120 rpm. PCR reactions contained 2×PCR mastermix (Abgene) and 10 μM of both the forward and reverse primers. $V_H$ and $V_L$ primers were as follows:

$V_H$-5', primer AF18
(SEQ ID NO: 15)
```
5'-CTCTCCACAGGCGCGCACTCCCAGGT (GC) CAGCTGGTGCA
            BssH II
```

$V_H$-3', primer Hlink
(SEQ ID NO: 16)
```
5'-ACCGCCAGAGCCACCTCCGCC
```

$V_L$-5', primer AF7
(SEQ ID NO: 17)
```
5'-GATCGATGGTGTGCACTCGGACATCCAGATGACCCAGTCT
              ApaL I
```

$V_L$-3', primer AF24':
(SEQ ID NO: 18)
```
5'-CTATTCCTTAATTAAGTTAGATCTATTCTACTCACGTTTGATCTCCA
           Pac I
GCTTGTCCCTCC
```

The forward and reverse primers carry the respective restriction sites for cloning into the respective IgG1 conversion vector. PCR reactions were run at 94° C. for 2 min, followed by 94° C. for 1 min., 55° C. for 1 min., 72° C. for 1 min. (30 cycles); followed by a final hold at 72° C. for 5 min.

PCR-amplified $V_H$ is as follows:

(SEQ ID NO: 26)
```
            BssH II
CTCTCCACAG GCGCGCACTC CCAGGTGCAG CTGGTGCAAT CTGGGGCTGA GGTGAAGAAG CCTGGGTCCT

CGGTGAAGGT CTCCTGCAAG GCTTCTGGAG GCACCTTCAG CAGCTATGCT ATCAGCTGGG TGCGACAGGC

CCCTGGACAA GGGCTTGAGT GGATGGGAGG GATCATCCCT CTCTTTGATA CATCAAACTA CGCACAGAAC

TTCCAGGGCA GAATCACGAT AACTGCGGAC AAATCCACGA GTACAGCCTA CATGGAACTG AGCAGCCTGA

GATTTGAGGA CACGGCCATT TATTACTGTG CGAGAGATAA CCCTTTACTT CTCGCTATGG ATGTCTGGGG

GAAAGGGACC ACGGTCACCG TCTCGAGTGG TGGAGGCGGT TCAGGCGGAG GTGGCTCTGG CGGT
             BstE II
```

PCR-amplified $V_L$ is as follows:

(SEQ ID NO: 27)
```
        ApaL I
GATCGATGGT GTGCACTCGG ACATCCAGAT GACCCAGTCT CCTTCCACCC TGTCTGCATC TATTGGAGAC

AGAGTCACCA TCACCTGCCG GGCCAGTGAG GGTATTTATC ACTGGTTGGC CTGGTATCAG CAGAAGCCAG

GGAAAGCCCC TAAACTCCTG ATCTATAAGG CCTCTAGTTT AGCCAGTGGG GCCCCATCAA GGTTCAGCGG

CAGTGGATCT GGGACAGATT TCACTCTCAC CATCAGCAGC CTGCAGCCTG ATGATTTTGC AACTTATTAC

TGCCAACAAT ATAGTAATTA TCCGCTCACT TTCGGCGGAG GGACCAAGCT GGAGATCAAA CGTGAGTAGA

ATAGATCTAA CTTAATTAAG GAATAG.
          Pac I
```

Vector pEU1.2 (IgG1) was used for B11 $V_H$ and pEU3.2 (kappa) for B11 $V_L$ (see discussion infra). Primer PECSEQ1 and 1.2 rev were used for PCR and sequence confirmation of $V_H$ clones. Primer P168 and P362 for PCR and sequence confirmation of $V_L$ clones. $V_H$ (BssHII and BstEII) and $V_L$ (ApaLI and PacI) PCR products were subjected to restriction endonulcease digestion to promote subcloning into pEU1.2 and pEU3.2, respectively.

```
                              (SEQ ID NO: 21)
PECSEQ1     5'-GCAGGCTTGAGGTCTGGAC
                              (SEQ ID NO: 22)
1.2Reverse  5'-CAGAGGTGCTCTTGGAGGAGGGTGC
                              (SEQ ID NO: 23)
P168        5'-CTTGAGGTCTGGACATATATATGGGTGACAATG
                              (SEQ ID NO: 24)
p362        5'-TCCTGGGAGTTACCCGATTGGAGGGCGTTA
```

The clone selected for transfection encodes the B11 $V_H$ amino acid sequence as follows:

```
                                           (SEQ ID NO: 10)
QVQLVQSGAE VKKPGSSVKV SCKASGGTFS SYAISWVRQA

PGQGLEWMGG IIPLFDTSNY AQNFQGRITI TADKSTSTAY

MELSSLRFED TAIYYCARDN PLLLAMDVWG KGTTVTVSS.
```

The clone selected for transfection encodes the B11 $V_L$ amino acid sequence as follows:

```
                                           (SEQ ID NO: 12)
DIQMTQSPST LSASIGDRVT ITCRASEGIY HWLAWYQQKP

GKAPKLLIYK ASSLASGAPS RFSGSGSGTD FTLTISSLQP

DDFATYYCQQ YSNYPLTFGG GTKLEIK.
```

Table 4 shows the alignment of the nucleotide and amino acid sequence of the B11 scFv.

TABLE 4

```
B11 CAGGTGCAGCTGGTGCAATCTGGGGCTGAGGTGAAGAAGCCTGGGTCCTCGGTGAAGGTC  (SEQ ID NO:
                                                                   7)
      Q  V  Q  L  V  Q  S  G  A  E  V  K  K  P  G  S  S  V  K  V   (SEQ ID NO:
                                                                   8)

B11 TCCTGCAAGGCTTCTGGAGGCACCTTCAGCAGCTATGCTATCAGCTGGGTGCGACAGGCC
      S  C  K  A  S  G  G  T  F  S  S  Y  A  I  S  W  V  R  Q  A

B11 CCTGGACAAGGGCTTGAGTGGATGGGAGGGATCATCCCTCTCTTTGATACATCAAACTAC
      P  G  Q  G  L  E  W  M  G  G  I  I  P  L  F  D  T  S  N  Y

B11 GCACAGAACTTCCAGGGCAGAATCACGATAACTGCGGACAAATCCACGAGTACAGCCTAC
      A  Q  N  F  Q  G  R  I  T  I  T  A  D  K  S  T  S  T  A  Y

B11 ATGGAACTGAGCAGCCTGAGATTTGAGGACACGGCCATTTATTACTGTGCGAGAGATAAC
      M  E  L  S  S  L  R  F  E  D  T  A  I  Y  Y  C  A  R  D  N

B11 CCTTTACTTCTCGCTATGGATGTCTGGGGAAAGGGACCACGGTCACCGTCTCGAGTGGT
      P  L  L  L  A  M  D  V  W  G  K  G  T  T  V  T  V  S  S  G

B11 GGAGGCGGTTCAGGCGGAGGTGGCAGCGGCGGTGGCGGATCGGACATCCAGATGACCCAG
      G  G  G  S  G  G  G  G  S  G  G  G  G  S  D  I  Q  M  T  Q

B11 TCTCCTTCCACCCTGTCTGCATCTATTGGAGACAGAGTCACCATCACCTGCCGGGCCAGT
      S  P  S  T  L  S  A  S  I  G  D  R  V  T  I  T  C  R  A  S

B11 GAGGGTATTTATCACTGGTTGGCCTGGTATCAGCAGAAGCCAGGGAAAGCCCCTAAACTC
      E  G  I  Y  H  W  L  A  W  Y  Q  Q  K  P  G  K  A  P  K  L

B11 CTGATCTATAAGGCCTCTAOTTTAOCCAGTGGGGCCCCATCAAGGTTCAGCGGCAGTGGA
      L  I  Y  K  A  S  S  L  A  S  G  A  P  S  R  F  S  G  S  G

B11 TCTGGGACAGATTTCACTCTCACCATCAGCAGCCTGCAGCCTGATGATTTTGCAACTTAT
      S  G  T  D  F  T  L  T  I  S  S  L  Q  P  D  D  F  A  T  Y

B11 TACTGCCAACAATATAGTAATTATCCGCTCACTTTCGGCGGAGGGACCAAGCTGGAGATC
      Y  C  Q  Q  Y  S  N  Y  P  L  T  F  G  G  G  T  K  L  E  I

B11 AAA
      K
```

Restriction digested DNA was purified using a QIAquick Nucleotide Removal Kit (Qiagen). The $V_H$- and $V_L$-restriction digestion PCR products were ligated into inserted into pEU1.2 (IgG1 heavy chain; see FIG. 7A (vector) and FIG. 7B (nucleotide sequence)) for B11 $V_H$ and pEU3.2 (kappa light chain; see FIG. 8A (vector) and FIG. 8B (nucleotide sequence))) for B11 $V_L$ Plasmid pEU1.2 is a 9.3 kB mammalian expression plasmid vector developed by CAT (FIG. 7A) which contains a human gamma 1 heavy chain expression cassette and a neo (G418R) selectable marker for mammalian cells and ampicillin resistant marker for *E. coli* cells. The completed gamma 1 heavy chain vector (i.e., with a $V_H$ region such as B11 $V_H$) can be co-transfected with a light chain gene plasmid into a mammalian cell line such as HEK-BENA or COS cells for transient expression of IgG. The $V_H$ PCR product is cloned as a BssHII-BstEII fragment into polylinker between the secretory leader and gamma 1 constant region sequences. The secretory leader sequence, MGWSCII-FLVATATGAHS (SEQ ID NO:25), is derived from a mouse heavy chain sequence while transcription is driven from the EF-1a promoter and terminated by the SV40 termination/poly A sequence. The Epstein Barr virus origin of replication is upstream of the EF-1α promoter. The oriP sequence enhances level of transient expression from human embryonic kidney 293-EBNA cells. Each ligation reaction was transfected into *E. coli* DH5a cells and plated on appropriate media/selectable marker. Plasmid pEU3.2 (FIG. 8A) contains an expression cassette for human kappa light chains and ampicillin resistant marker for *E. coli* cells. The $V_L$ PCR product is cloned as a ApaLI-PacI fragment into polylinker between the secretory leader and the human kappa constant domain sequences. Plasmid pEU3.2 contains a secretory leader peptide from a mouse heavy chain sequence transcription is driven from the EF-1c promoter and terminated by the human kappa light chain gene/ploy A sequence. Plasmid pEU3.2 also contains the Epstein Barr virus origin of replication upstream of the EF-1α promoter as well as the oriP sequence. The kappa light chain vector can be co-transfected with a heavy chain gene plasmid into HEK-BENA or COS cells for transient expression of IgG.

Growth and preparation of HEK-EBNA cells for transfection—HEK-EBNA stock cells were maintained in Dulbecco's Modified Eagle Medium (DMEM) containing 10% fetal bovine serum (v/v), 10% DMSO (v/v). Three to 4 days prior to transfection, stock culture cells were plated in Dulbecco's Modified Eagle Medium (GIBCO) containing 10% fetal bovine serum, 4 mM glutamine, 1× non essential amino acids, 1× penicillin/streptomycin. On the day before transfection, cells were split in 75 ml of Dulbecco's Modified Eagle Medium containing 10% fetal bovine serum, 4 mM glutamine, 1× non essential amino acids, 1× penicillin/streptomycin with cell numbers of 7-9×10$^6$ in a T150 tissue culture flask. After 1 day growth, cells were 60% confluent, and therefore suitable for transfection. The culture was inoculated with the $V_H$- or $V_L$-containing clone in 100 ml of 2xYT medium with 50 μg/ml of Ampicillin. The culture was grown overnight at 37° C. at 280 rpm. After incubation, a 1 ml sample of the culture was added to 1 ml of 40% glycerol and stored at −80° C. Plasmid DNA was extracted from the remainder of the overnight culture using a QIAgen Maxiprep kit according to the manufacturer's instructions. Plasmid DNA was re-dissolved in 100 μl of water and the concentration of DNA was determined by absorbance at 260 nm. Forty micrograms of each plasmid DNA was diluted in DMEM (no serum) to a total volume of 1.5 ml in a 15 ml Falcon tissue culture tube. The tube was mixed and 400 μl of PolyFect Transfection Reagent (Qiagen) was added to the DNA solution, vortexed for 10 seconds and incubated for 15 min at RT. Fifty five ml of Dulbecco's Modified Eagle Medium containing 10% fetal bovine serum, 4 mM glutamine, 1× non essential amino acids, 1× penicillin/streptomycin was added to the cell culture. Five ml of cell growth medium was added to the reaction tube containing the transfection complexes, which were mixed and the total volume was immediately transferred to cell culture. After overnight incubation, the medium was removed and replaced with 75 ml of OPTI-MEM1 (Reduced Serum Medium-GIBCO). Immediately prior to transfection, the medium was replaced with 20 ml of fresh DMEM containing 2% fetal bovine serum and 1× penicillin/streptomycin. One thousand milliliters of filter sterilized 2×HEPES buffered saline (2×HBS) was warmed in a 37° C. water bath. One hundred microliters of $CaCl_2$ (2.5 M) was added to 100 μl of DNA mixture which contains 50 μg of each plasmid in a 15 ml Falcon tissue culture tube. The pre-warmed DNA mixture was added to HBS drop wise while mixing on a vortex mixer and incubated for 2-5 min at 37° C. The HBS/DNA solution was added to the HEK-EBNA cells and incubated overnight, followed by replacement of the medium with 25 ml of fresh CD-CHO medium containing 8 mM glutamine, 1× penicillin/streptomycin supplement, 1× hypoxanthine/thymidine supplement.

Culture of transfected cells and harvesting of IgG—The cells were incubated overnight at 37° C., 5% $CO_2$ concentration, with humidification. The medium was harvested, filter sterilized and stored at 4° C. The culture was replaced with fresh medium and harvesting was continued at 2-3 day intervals for up to 12 days, each time filter sterilizing the harvested medium and pooling with previously harvested medium from the culture.

Capture ELISA for IgG—Initial analysis of IgG1 concentration in the culture medium was carried out using capture ELISA, which monitors the success of the transfection through an approximation of the concentration of IgG present in the harvested medium. Fragment goat anti-human IgG (H+L) (Jackson ImmunoReseach Lab) was diluted to 10 μg/ml with 50 mM Tris, pH 9.5. Each well of a Nunc Immunosorb plate (NUNC) was coated with 100 μl of diluted capture antibody. The plate was sealed, incubated overnight at 4° C., washed three times with PBS/Tween 20 [0.5% (v/v)], three times with PBS and blotted dry with paper towels. The wells were then blocked with 150 μl of PBS/3% powdered milk per well for 1 h at 37° C. Plates were then washed three 3 times with PBS/Tween 20, three times with PBS and blotted dry. One hundred microliters of PBS/3% powdered milk was added to all wells except for A1, B1, A12 and B12. An appropriate standard antibody (hu IgG-Sigma) was diluted in PBS/3% powdered milk to a final concentration of 2.5 μg/ml and 200 μl of the standard Ab was added to A1 and B1 mix by pipetting and transferring 100 μl of the antibody from A1 to A2 and B1 to B2. This dilution step was repeated down to A10 and B10. One hundred microliters of the antibody dilution from was removed and discarded from wells A10 and B10 to ensure equal volumes in the wells, resulting in a 1 in 2 serial dilution of antibody standard (2.5 μg/ml-0.05 μg/ml) in rows A and B up to column 10. One hundred microliters of filtered culture medium containing IgG was diluted in 400 μl PBS/3% powdered milk. One hundred microliters was added to duplicate wells on adjacent column 1, mixed by pipetting and 100 μl transferred to the next column (e.g. C2 and D2) and 1 in 2 serial dilutions were continued down each column. One hundred microliters was discarded from column 12 to ensure equal volumes in the wells. One hundred microliters of un-inoculated medium was added to wells A12 and B12 as medium (negative) controls. The plate was incubated at 37°

C. for 2 h, washed five times with PBS/Tween 20 and five times with PBS, and blotted dry with paper towels. Appropriate amounts of horseradish peroxidase (HRP) conjugated detection antibody (Goat anti human IgG, FC specific-Sigma) were diluted in PBS/3% powdered milk (1 in 10000 dilutions) and 100 µl of the diluted detection antibody was added to each well, incubated at 37° C. for 1 h, washed five times with PBS/Tween 20 and five times with PBS, and blotted dry with paper towels. Finally, 1001 of 3,3', 5,5'-tetramethylbenzidine (TMB) was added to each well and incubated at RT until color developed (approximately 1-5 min). Fifty microliters of 0.5 M sulphuric acid was added to stop the color reaction and the plates were read at 450 nm.

Purification of IgGs from harvested supernatant using protein A sepharose—A Protein A sepharose (Amersham) column (1 ml for 1 L of cell supernatant) was pre-equilibrated in 20 ml of buffer PBS, 0.02% Tween 20 prior to addition of the samples. Harvested supernatant was loaded onto the column using a peristatic pump at 4° C., with the flow rate not allowed to exceed 3 ml min$^{-1}$. The unbound fraction was reloaded 2 additional times prior to washing the column with 100 column volumes of buffer PBS, 0.02% Tween 20. The antibody was eluted by using 5 ml of 0.1M glycine pH 2.8 and collected directly into 0.5 ml of 2M Tris pH 8.0. The eluting step was repeated three times, the column washed with 20 ml of 0.1M glycine pH 2.8 and 100 ml of buffer PBS, 0.02% Tween 20. The eluted fractions were analyzed by SDS PAGE, and then buffer exchanged and concentrated by using Amicon Ultra 15 (MILLIPORE). The sample is quantitated by ELISA or OD280 where 1.34 mg per ml gives an absorbance of 1.0. Purification was completed at ambient temp, while reagent vessels and fractions were kept on ice and samples were subsequently stored and −20° C.

EXAMPLE 4

Assays for Determination of D5 HIV-1 Neutralizing Activity

Materials and Methods—Design of vectors for HIV Reporter Particle (HIVRP) assay—The plasmid pMM310, encoding a vpr-BlaM fusion protein, was constructed by fusion PCR. A vpr coding sequence was amplified from the YU2 provirus template (AIDS research and reference reagent program) using primers MM425 (5'-GGATCCGAA-CAAGCCCCAGAA GAC-3' [SEQ ID NO:28]) and MM426 (5'-GGGCTCGAGTTAGGATCTACTGGCTCC-3' [SEQ ID NO:29]). A β-lactamase coding sequence was amplified from pCMV-BlaM (Aurora Biosciences) using primers MM423 (5'-GGAAGCTTGG TACCACCATGG—3' [SEQ ID NO:30]) and MM424 (5'-TGGGGCTTGTTCGGATC-CCCAATGCT TAATCAGTGA-3' [SEQ ID NO:31]). A mixture of these fragments was re-amplified with primers MM423 and MM426 to yield the fusion sequence, which was cloned into pcDNA3.1/zeo$^{(+)}$ as a HindIII/XhoI fragment and verified by nucleotide sequencing.

HIV Reporter Particle (HIVRP) assay —HIV particles containing active β-lactamase were generated by co-transfecting 293T cells with a chimeric NL4-3 provirus DNA containing the envelope gene of the HXB2 strain (5 µg/T75 flask) and pMM310 (5 µg/T75 flask) using the Fugene6 reagent (60 µl/T75 flask) according to the manufacturer's instructions (Roche, Basel, Switzerland). Supernatants harvested 48 h later contained HIV particles used for subsequent experiments. Supernatants (90 µl) and SuP-T1 cells stably expressing CCR5 (622 F) (0.5-1×105 cells/well) were mixed in Costar (Corning, N.Y.) 3603 96-well plates with or without scFvs, incubated at 37° C. for 3 hours to allow virus binding and entry, loaded with 1 µM of CCF4-AM (Aurora Biosciences, San Diego, Calif.) and incubated at room temperature an additional 16-18 h. Fluorescence was quantified using a bottom-reading BMG PolarStar fluorometer (Durham, N.C.) with the following filters (Chroma Technologies, Brattleboro, N.H.): 410±12 nm (excitation), 460±12 nm (blue emission), and 530±12 nm (green emission).

Single-cycle HIV infectivity assay —HIV strains HXB2, BaL, 89.6, MN-1, and NL4-3 were purchased from Advanced Biotechnology Inc. (Bethesda, Md.). HIV pseudotyped with the VSV-G protein was generated by transfecting 293T cells with the proviral DNA construct R8.env and pCMV-VSV-G (gift of J. Kappes, University of Alabama Birmingham). P4-2/R5 cells (gift of N. Landau, Salk Institute) are HeLa cells stably expressing human CD4 and CCR5 and harboring a β-galactosidase reporter gene driven by a tat-responsive fragment of the HIV-2 LTR. P4-2/R5 cells were maintained at 37° C. and 5% $CO_2$ in phenol red-free Dulbecco's modified Eagle's medium, 10% fetal bovine serum. For infectivity assays, cells were seeded in 96-well plates (Costar) at 2.5×10$^3$ cells/well and infected the following day with the various strains of HIV-1 at a multiplicity of infection of ~0.01 in the presence of scFvs or antibodies. After incubating an additional 48 h at 37° C./5% $CO_2$, cells were lysed and β-galactosidase activity was quantified using GalScreen chemiluminescent substrate (Tropix, Bedford, Mass.) according to the manufacturer's instructions.

ALPHASCREEN™ based gp41 N—C peptide interaction assay—As discussed herein, IZN36 is a chimeric peptide, composed of sequences that form a leucine zipper (IZ) and the HR1 region of the gp41 ecto-domain (N36). This peptide naturally forms a trimer. Using a homogenous ALPHAS-CREEN™ detection kit PERKINELMER® (Wellesley, MA) Cat.# 6760612), a specific interaction was observed between a biotinylated version of IZN36 and a synthetic peptide derived from the gp41 HR2 region fused to a hemagglutinin epitope tag at its C-terminus (C34-HA) (C34: WMEW-DRENNYTSILHSLIEESQNQQEKNEQELLGGGYPYD VPDYAGPG-NH$_2$ (SEQ ID NO:32). The interaction occurred between bio-IZN36 peptide that was captured by streptavidin coated donor beads and C34-HA captured by anti-HA antibody coated acceptor beads. The peptide concentrations selected for subsequent experimentation were 9 nM bio-IZN36 and 18 nM C34-HA in a buffer containing 25 mM HEPES (pH 7.4)/100 mM NaCl/0.1% BSA. Peptide/bead complexes were incubated for ~18h at room temperature in the presence or absence of antibody.

ALPHASCREEN™-based D5 IgG/IQN17 binding assay—Using an ALPHASCREEN™ detection kit involving streptavidin coated donor beads that captured biotinylated-IQN17 and protein—A coated acceptor beads, which captured D5 IgG, an interaction between D5 and IQN17 was readily observed. Subsequent experimentation was performed with 3.3 nM of D5 antibody and bio-IQN17. Increasing concentrations of various mutant IZN17 peptides were incubated with D5 coated acceptor beads for 1h prior to addition of bio-IQN17 coated donor beads. These mixtures were incubated for an additional 18 hours.

Results—Identification of 5-Helix/IZN36 cross-reactive antibodies that neutralize HIV-1-Bacteriophage expressing scFvs (96 in total) that interacted with 5-Helix and IZN36 were isolated. The scFvs, which contain hexa-histidine tags were purified and concentrated on Nickel columns. These purified scFvs were tested for ability to prevent HIV-1 (envelope from strain HXB2) entry using a reporter particle assay (HIVRP). Two scFvs, termed 5H/I1-BMV-D5 and 5H/I1-

Figure 9:
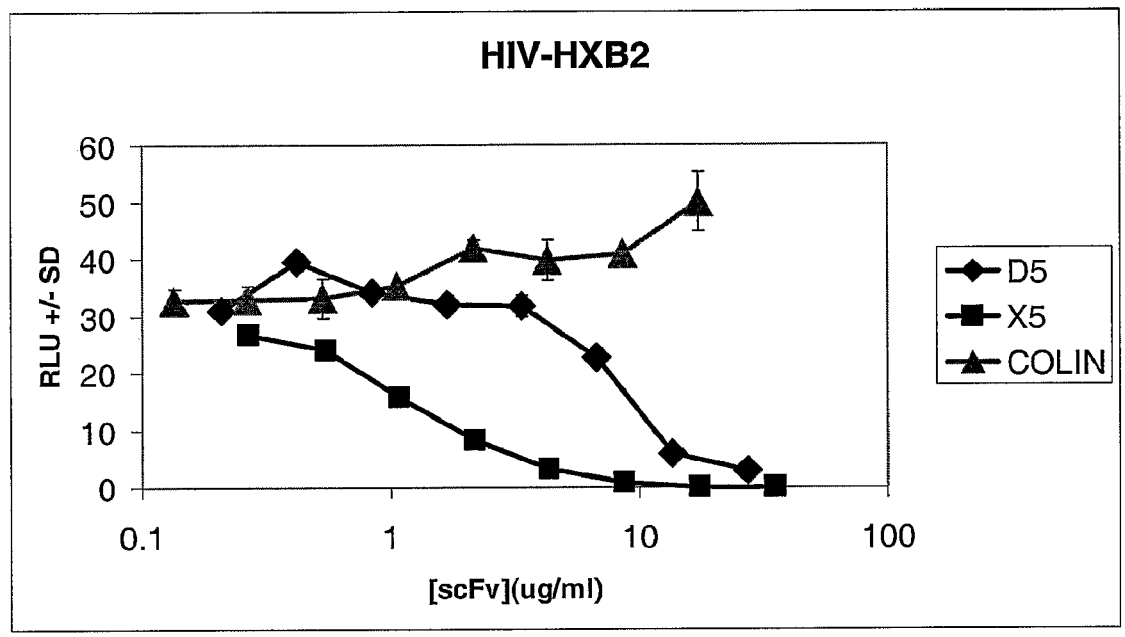
FIG. 9 shows the ability of D5 scFv to inhibit infectivity of the CXCR4 HIV-1 stain, HX2B. X5 is a gp120 specific scFv and scFv COLIN is utilized as a negative control.

BMV-B11 (also referred to herein as "D5" and "B11" scFvs) were capable of inhibiting HIV-1 entry. To assess whether D5 and B11 scFvs possessed broader anti-viral activity, they were tested in a single cycle infectivity assay against the CXCR4-tropic HIV-1 strain HXB2 and the CCR5-tropic strain BaL. Consistent with the results observed in the HIVRP assay, D5 scFv inhibited HIV—HXB2 replication in this single cycle infectivity assay (FIG. 9). ScFv D5 appeared less potent than the X5 scFv, which interacts with the co-receptor binding area on the HIV surface protein gp120. The negative control scFv COLIN had no effect on HIV replication. D5 scFv also inhibited replication of HIV-BaL but again seemed less potent than X5 scFv. To determine whether this anti-viral effect of D5 scFv was specific for HIV envelopes, it was tested against HIV particles pseudotyped with the surface protein of the Vesicular Stomatitis Virus (VSV-G). Neither D5 nor X5 scFvs prevented infection by these viral particles. Similar to D5 scFv, the B11 scFv displayed anti-viral properties against the HIV—HXB2 strain in this single cycle infectivity assay but appeared less potent than D5. Extensive titrations of D5 scFv were performed against HIV—HXB2 and HIV-BaL in order to derive an Inhibitory Concentration 50 ($IC_{50}$) against each virus. The $IC_{50}$ of D5 scFv against HIV—HXB2 was 320 nM (8 ug/ml) and 600 nM (15 ug/ml) for HIV-BaL.

To determine if the variable heavy ($V_H$) and variable light ($V_L$) regions of D5 and B11 scFvs can be transferred to an IgG molecule and confer anti-viral activity, these two regions were sub-cloned into Immunoglobulin Heavy and Light chain mammalian expression vectors, as described in Example Sections 1 and 2. Co-transfection of these vectors in 293 cells resulted in the production of full length IgG1 molecules. These antibodies were tested for anti-viral activity in a single cycle infectivity assay against HIV—HXB2. The IgG1 version of D5 was capable of inhibiting HIV—HXB2 with comparable potency to the D5 scFv. The $IC_{50}$ of the D5 IgG was 261 nM and the $TC_{50}$ of the scFv is 238 nM. Both D5 agents were less potent than the gp120 co-receptor binding site-specific X5 scFv ($IC_{50}$=30 nM). This result demonstrates that synthetic gp41 mimetic peptides can select for HIV neutralizing antibodies.

Additional HIV strains were tested in the single cycle infectivity assay to assess the breadth of D5 and B11 neutralization potential (Table 5). The CCR5-tropic strain BaL was approximately 3-fold more sensitive to D5 IgG with an average $IC_{50}$ of 93 nM. In contrast, the dual tropic strain (CCR5 and CXCR4) HIV 89.6 was approximately 6-fold less susceptible to neutralization by D5 IgG. Finally, strains MN-1 and NL4-3 appeared to display a similar degree of susceptibility as was noted for HXB2 with average $IC_{50}$ of 393 and 226 nM, respectively. B11 IgG appeared to produce a similar pattern of neutralization potencies (Table 5). This panel of five viruses revealed a 13-20-fold range in neutralization potencies for D5 and B11 IgGs.

TABLE 5

| Envelope | D5 IgG $IC_{50}$ (nM) | B11 IgG $IC_{50}$ (nM) | Gp41 HR1 sequence Differences from HXB2 in BOLD |
|---|---|---|---|
| HXB2 | 310 (n = 6) | 290 (n = 2) | SGIVQQQNNLLRAIEAQQHLLQLTVWGIKQLQARILA (SEQ ID NO: 33) |
| BaL | 93 (n = 4) | 73 (n = 2) | SGIVQQQNNLLRAIEAQQHLLQLTVWGIKQLQARVLA (SEQ ID NO: 34) |
| 89.6 | 1750 (n = 2) | 943 (n = 1) | SGIVQQQNNLLRAIEAQQHMLQLTVWGIKQLQARVLA (SEQ ID NO: 35) |
| MN-1 | 393 (n = 4) | 244 (n = 2) | SGIVQQQNNLLRAIEAQQHMLQLTVWGIKQLQARVLA (SEQ ID NO: 36) |
| NL4-3 | 226 (n = 1) | N. D. | SDIVQQQNNLLRAIEAQQHLLQLTVWGIKQLQARILA (SEQ ID NO: 37) |
| VSV-G | Not active | N.D. | N/A |

Figure 10:
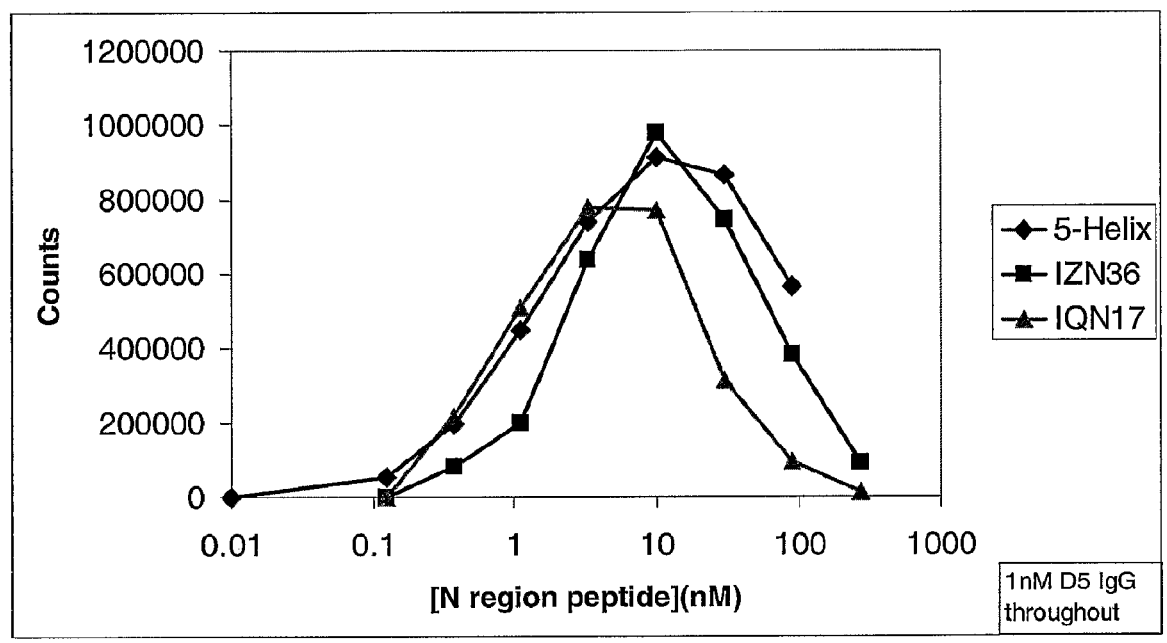
FIG. 10 shows the ability of D5 IgG4 to interact with 5-helix, IZN36, and IQN17 in an Alpha Screen assay.
Figure 11:
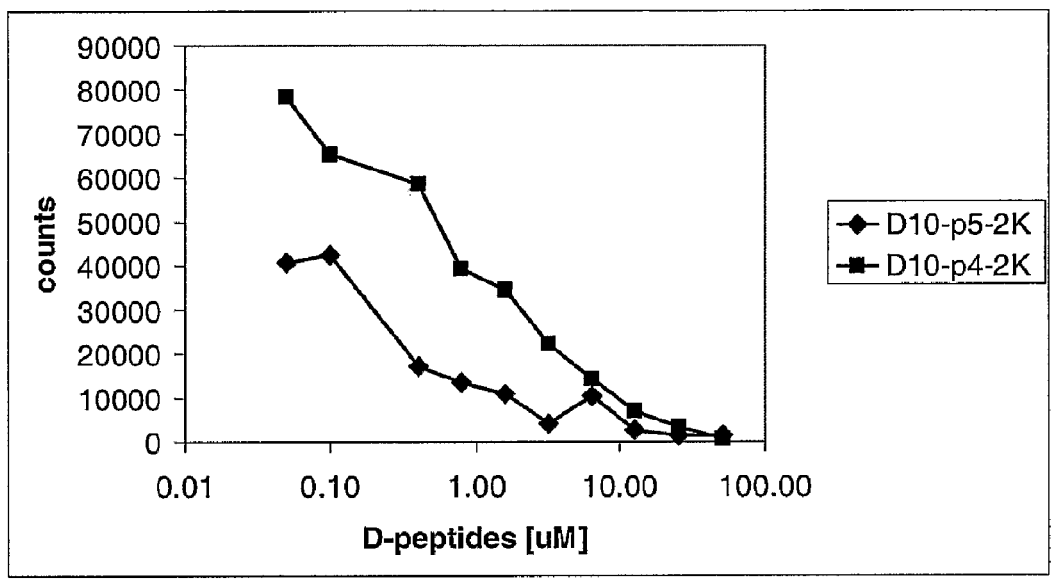
FIG. 11 shows the ability of two D-peptide inhibitors (D10-p5-2K and D10-p4-2K, which target the hydrophobic pocket within adjacent HR1 pre-hairpin coils) to inhibit interaction of D5 IgG4 with biotinylated 5-Helix in an Alpha Screen assay.
Figure 12:
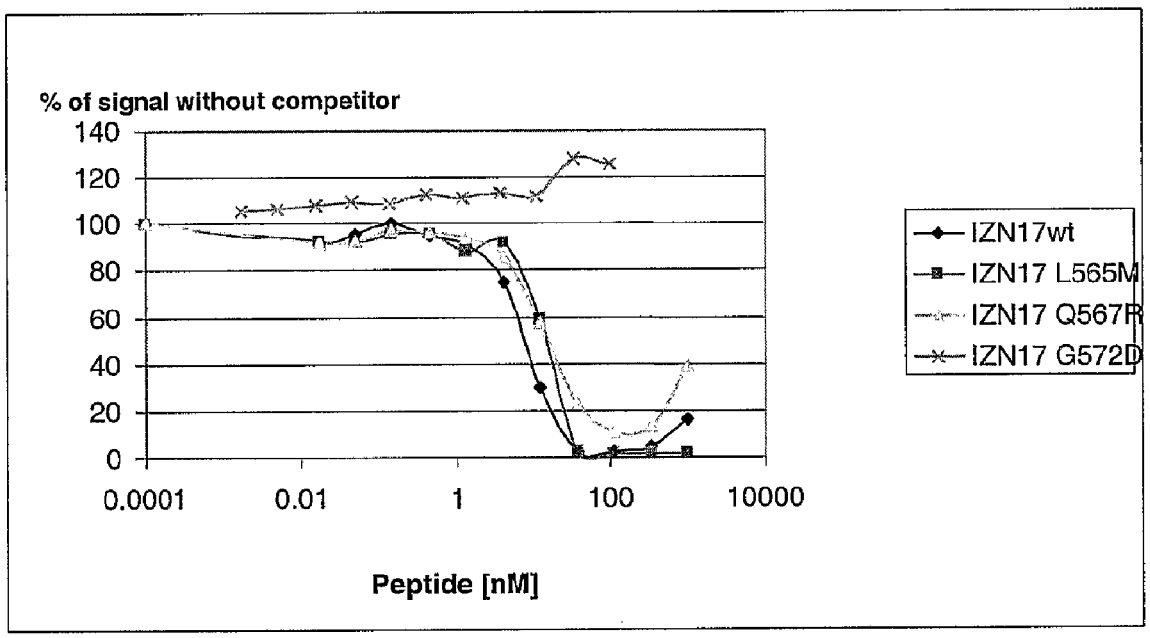
FIG. 12 shows the effect that mutations within IZN17 (IZN17 L565M, IZN17 Q567R, IZN17 G572D) have on D5 IgG4 binding in an Alpha Screen assay. These mutation represent changes within the hydrophobic pocket region of gp41.
Figure 13:
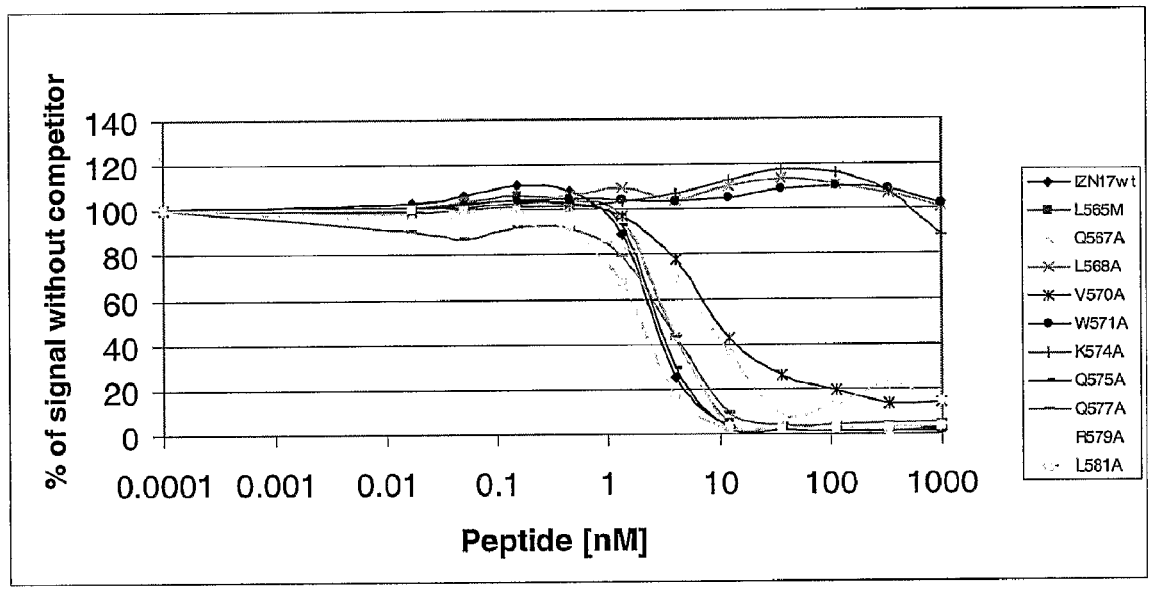
FIG. 13 shows an IZN17-based alanine scanning experiment which indicates critical amino acids within the hydrophobic pocket necessary for D5 IgG binding.

Identification of the D5 IgG binding site in the Heptad Repeat-1 region—Since the D5 scFv was isolated by virtue of its cross-reactivity to 5-Helix and IZN36, studies were conducted to determine if the gp41 epitope lies in the groove formed by adjacent Heptad Repeat-1 (HR1). To confirm that D5 IgG does indeed interact with both 5-Helix and IZN36, an ALPHASCREEN™ based assay was devised in which biotinylated versions of both peptides were captured by streptavidin coated donor beads and D5 IgG was bound by protein-A coated acceptor beads. Using this proximity assay, a clear interaction between D5 antibody and both peptides was observed with peak signals noted at peptide concentrations of 10 nM and antibody concentrations of 1nM (FIG. 10). As noted supra, a well defined hydrophobic pocket is formed by the C-termini of adjacent HR1 domains. This pocket accommodates three key amino acids from the HR2 region during the formation of the 6-helical bundle, a structure believed to represent a late stage intermediate of the virus-mediated fusion process. The integrity of this pocket is crucial for HIV infectivity. To determine whether D5 IgG interacts directly with this hydrophobic pocket, ALPHASCREEN™ donor beads were coupled with biotinylated IQN17. This small peptide effectively recreates the hydrophobic pocket. Mixing IQN17-coupled donor beads with D5 IgG coupled acceptor beads produced an evident interaction between D5 antibody and IQN17. This finding indicates that D5 IgG interacts with the hydrophobic pocket formed by the HR1 region of the gp41 ecto-domain. To bolster this finding, cyclic D-peptides that specifically interact with the hydrophobic pocket and represent low micromolar inhibitors of HIV infection were tested for ability to prevent the interaction of D5 IgG with biotinylated 5-Helix. Two peptides termed D10-p5-2K and D10-p4-2K (Eckert et al., 1999, *Cell* 99:103-115) with differing affinities for the hydrophobic pocket were tested in this assay. Both peptides effectively prevented the interaction of D5 IgG with 5-Helix (FIG. 11). D10-p5-2K, which has a slightly higher affinity for the pocket (KD=1.2 uM), appeared to inhibit D5 IgG binding to 5-Helix more effectively. To ensure that this inhibitory effect was specific for D5 IgG, these peptides were next examined for ability to impede the attachment of a mouse monoclonal antibody (F19) that interacts with 5-Helix but in a region distinct from the pocket. Neither peptide had an appreciable impact on the attachment of F19 to 5-Helix, indicating that the cyclic D-peptides D10-p5-2K and D10-p4-2K inhibit the binding of D5 IgG specifically. This result confirms that D5 IgG engages 5-Helix in the area of the hydrophobic pocket.

Delineation of the D5 epitope—To identify specific amino acids of the hydrophobic pocket that are required for attachment of D5 IgG, a series of mutant IZN17 peptides were tested for ability to compete the binding of D5 IgG with biotinylated IQN17 in an ALPHASCREEN™ format. Amino acid substitutions were engineered into IZN17, specifically targeting solvent exposed residues. First, an IZN17 mutant in which Glycine at position 572 was replaced with aspartic acid was tested. This mutation effectively introduced a large side-chain into the hydrophobic pocket of IZN17 thus filling this cavity. This G572D mutant was completely incapable of competing D5 binding to IQN17. This result indicates that introduction of a bulky side chain into the hydrophobic pocket impedes binding of D5 IgG (FIG. 12). Three additional IZN17 mutants were incapable of competing D5 binding. Alanine substitutions at positions K574, L568 and W571 in IZN17 completely abolished binding of D5 indicating that these three amino acids likely form the D5 epitope (FIG. 13). One additional mutant (V570A) appeared to compete D5 binding less effectively than WT IZN17 peptide, perhaps suggesting that V570 forms a minor contact point for D5 IgG (again, see FIG. 13). These four amino acid residues, as well as the spatial requirement met by G572, are shown in FIG. 14 to represent the conformational epitope for D5 binding to adjacent N17 coils of the pre-hairpin trimeric structure.

Affinity of D5 IgG for the hydrophobic pocket of HR1—The affinity of D5 IgG for various peptides was next determined by surface plasmon resonance (Biacore). The KD of D5 for 5-Helix and IZN17 was 0.26 and 0.1 nM, respectively (Table 6). Introduction of proline residues into IQN17 disrupts the helicity of the peptide which in turn alters the integrity of the hydrophobic pocket (IQN17-2pro). The affinity of D5 for such a peptide was significantly reduced (KD=240 nM). Finally, consistent with the finding of the previous section indicating that the IZN17 G572D mutant fails to interact with D5, the affinity of D5 for this mutant is considerably reduced (KD=550 nM) when compared to WT IZN17.

TABLE 6

| Peptide | KD (nM) | On (1/Ms) | Off (1/S) |
|---|---|---|---|
| 5-Helix | 0.26 | 3.9e5 | 1.0e−4 |
| IZN17 | 0.1 | 6.1e6 | 5.9e−4 |
| IZN17-G572D | 550 | 5.5e3 | 3.0e−3 |
| IZN17-L565M | 0.3 | 3.0e6 | 8.9e−4 |
| IZN17-Q567R | 1.5 | 8.0e5 | 1.2e−3 |
| IQN17-2Pro | 240 | 9.0e3 | 2.2e−3 |

Mechanism of Action of D5 IgG—It is shown herein that D5 IgG binds the hydrophobic pocket of HR1, which normally accommodates critical residues of the HR2 region during the formation of the six helical bundle. It is conceivable that D5 blocks HIV infection by preventing the formation of 6-Helix. To explore this possibility, a novel N—C peptide interaction assay was developed. Using ALPHASCREEN™ technology, biotinylated IZN36, coupled to streptavidin coated donor beads was observed to interact specifically with C34-HA, captured by acceptor beads coated with anti-HA antibodies (FIG. 15). In this assay, D5 IgG prevented the interaction of C34-HA with IZN36 suggesting that this novel antibody may function like T20/Fuzeon by preventing HR2 from engaging HR1. To ensure that the D5-mediated inhibitory effect observed in this assay was specific, a mouse monoclonal antibody (D13) raised against 5-Helix but which does not bind the hydrophobic pocket was tested. D13 did not affect the interaction of C34-HA with IZN36 (again, see FIG. 15).

EXAMPLE 5

HIV-1 gp41 5-Helix-D5 (Fab) Complex

Protein expression, complex formation and purification—HIV-1 gp41-derived 5-Helix was expressed in bacteria and then refolded. The D5 Mab was expressed by transient transfection in EBNA-293 cells as discussed herein. D5 was purified from the supernatant on a protein A column. The Fab was generated by papain cleavage of the D5 Ab and then further purified by SEC chromatography on an analytical Superdex-200 (20 mM Tris-HCl buffer and 100 mM NaCl). Complex formation was monitored by titration of 5-Helix with the D5-Fab and followed by Native-Page gel shifts. The complex was obtained by mixing these two proteins approximately in a 1:1 molar stochiometry. The mixture was the further purified by SEC chromatography on a Superdex-200 analytical column (100 mM NaCl and 10 mM Tris HCl 20 mM) to remove the excess Fab or 5-helix. In gel filtration the complex migrates as a 75 KDa protein consistent with a 1:1 complex. The complex was finally concentrated to 8 mg/ml and used in crystallization experiments.

Crystallization—Crystals suitable for structure determination were obtained using the hanging drop crystallization method. 1 ul of complex solution was mixed with 1 ul of a crystallization solution containing 18% PEG4000 200 mM Li2SO4 and 100 mM Tris-HCl pH 8.5. Crystals appeared after 2-3 days. A complete 2.3 A native data set was collected at the Elettra Sinchrotron (Trieste) from flash-cryocooled crystals. For cryo-cooling the crystals were first transferred in a solution of the same composition of the crystallization solution with an addition of 20% glycerol and then cryo-cooled on a N2 stream (100K). The crystals belong to the C2 monoclinic space group with cell parameters a0=b=c=with only one copy of the complex in the asymmetric unit (1 Fab and 1 5-helix molecule).

Structure solution and refinement—The structure was solved by standard Molecular Replacement techniques using the “Molrep” program (CCP4 suite of programs). A Fab V- and C-domains (separately and after deletion of the CDRs) and a 5-helix model (derived from the gp41 structure after removal of one C-helix) were used in the Molecular Replacement search. The Molecular Replacement solution model showed that the V— and C— chains are close in space and form the D5-Fab and the V-chain is in proximity of 5-helix. Moreover the solution showed good crystal packing. This solution was used to generate Sigmaa-weighted 2|Fo-Fc| electron density maps and Sigmaa-weighted 2|Fo-Fc| composite-omit electron density maps with CNS. Several cycles of model building with the programs “0” and Quanta and refinement with the CNS program have resulted in the present model that includes approximately 95% of the residues of the complex. No density is present for the linker connecting the helices of 5-helix. The quality of the electron density is very good and well defined for both the CDRs loops and for 5-helix. At present the Rwork is of 30% and Rfree of 33%. Further refinement of the structure is ongoing.

Figure 17:
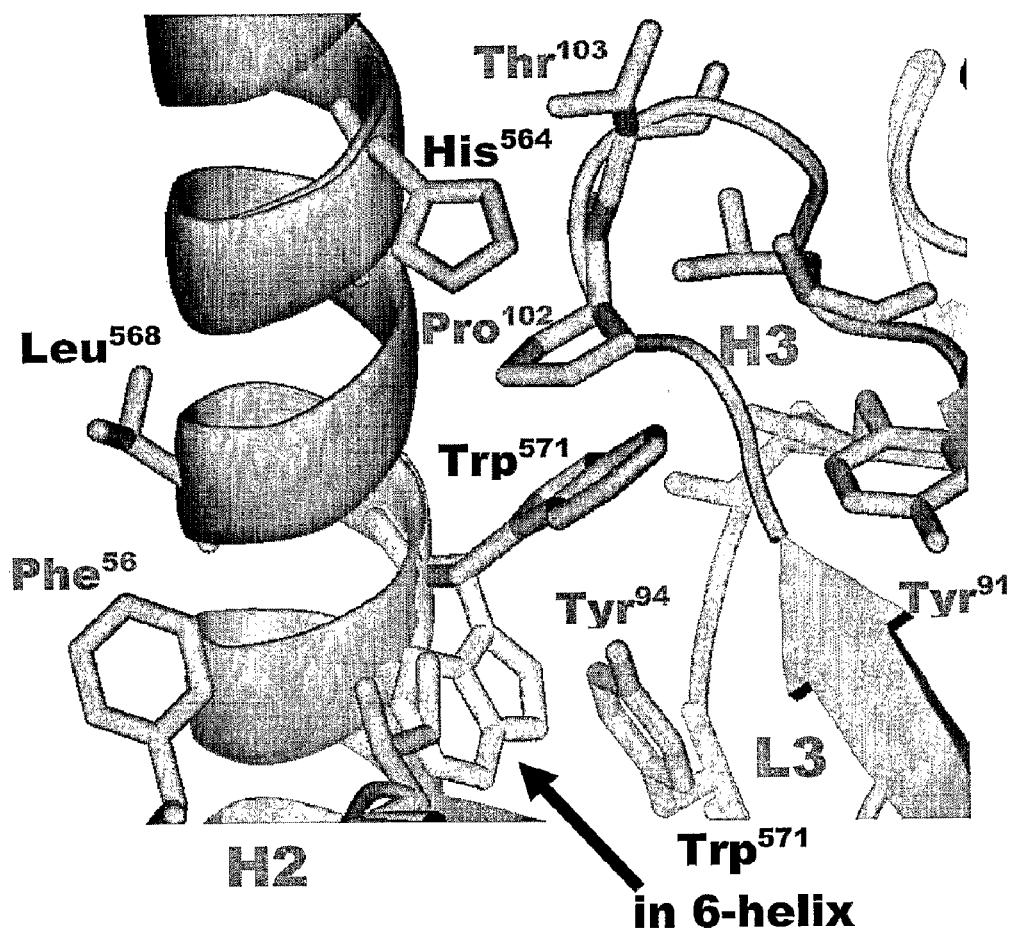
FIG. 17 shows Tryptophan 571 of gp41 surrounded by several residues CDRs side chains and in the complex adopts a different rotamer (top, darker) compared to what observed in gp41 (e.g., 6-helix; bottom).

Structure description—The structure confirmed the anticipated stochiometry of one D5-Fab per one 5-helix molecule. A preliminary analysis of the structure shows that several Fab CDRs loops contact an extended surface on 5 helix. A surface of almost 2000A2 (roughly 1000A2 on each molecule) is buried in this interaction. Three aspects of the molecular interaction are immediately apparent from this structure. The Fab heavy chain CDR2 loop and in particular Phenylalanine 56 binds to the gp41 "hydrophobic pocket" occupying a position equivalent to Tryptophan 631 and Tryptophan 628 of the C-peptide in the gp41 6-helix core structure (FIG. 16A-B). The N-helix Tryptophan 571 that forms an edge of the "pocket" in the gp41 structure assumes a different rotamer in the complex and is surrounded by several Fab residues (mainly heavy and light chains CDR3s) (FIG. 17; Table 7). A similar conformation of this Tryptophan was observed in a previous structural study with a gp41 inhibitor complex (Zhou et al., 2002, *Bioorg Med Chem.* 8(9):2219-2227) and could also be present in the unbound 5-helix. Third, residues in the light chain CDR1 contact a proximal C-peptide of 5-helix. These contacts account only for approximately 20% of the total buried surface.

TABLE 7

List of Contacts

| D5 | | | | 5-helix | | | | |
|---|---|---|---|---|---|---|---|---|
| HCDR2 | | | | N-peptide1 | | | | |
| Ile | 55G | O | ... | Lys | 574A | CE | ... | 3.53 |
|  |  |  | ... | Lys | 574A | NZ | ... | 3.25*** |
|  |  |  | ... | Lys | 574A | CD | ... | 3.08 |
| Phe | 56G | CB | ... | Ile | 573A | CG2 | ... | 3.87 |
| Phe | 56G | CG | ... | Ile | 573A | CG2 | ... | 3.67 |
| Phe | 56G | CD2 | ... | Ile | 573A | CB | ... | 3.95 |
|  |  |  | ... | Ile | 573A | CG2 | ... | 3.71 |
| Phe | 56G | O | ... | Gln | 577A | CB | ... | 3.24 |
|  |  |  | ... | Gln | 577A | CG | ... | 3.31 |
| Gly | 57G | C | ... | Gln | 577A | CG | ... | 3.71 |
|  |  |  | ... | Gln | 577A | CD | ... | 3.99 |
|  |  |  | ... | Gln | 577A | OE1 | ... | 3.98 |
| Gly | 57G | O | ... | Gln | 577A | CD | ... | 3.84 |
|  |  |  | ... | Gln | 577A | OE1 | ... | 3.54* |
| Thr | 58G | N | ... | Gln | 577A | CG | ... | 3.36 |
|  |  |  | ... | Gln | 577A | CD | ... | 3.87 |
| Thr | 58G | CA | ... | Gln | 577A | CG | ... | 3.38 |
|  |  |  | ... | Gln | 577A | CD | ... | 3.52 |
|  |  |  | ... | Gln | 577A | NE2 | ... | 3.69 |
| Thr | 58G | CB | ... | Gln | 577A | CG | ... | 3.71 |
| HCRD2 | | | | N-peptide2 | | | | |
| Ile | 53G | CG2 | ... | Leu | 568E | CG | ... | 3.96 |
| Ile | 53G | CG1 | ... | Gln | 575E | OE1 | ... | 3.40 |
| Ile | 53G | CD1 | ... | Gly | 572E | CA | ... | 3.64 |
|  |  |  | ... | Gln | 575E | OE1 | ... | 3.41 |
|  |  |  | ... | Trp | 571E | CB | ... | 3.67 |
|  |  |  | ... | Trp | 571E | C | ... | 3.81 |
|  |  |  | ... | Gly | 572E | N | ... | 3.50 |
|  |  |  | ... | Gln | 575E | CD | ... | 3.90 |
| Ile | 55G | CD1 | ... | Leu | 568E | CD2 | ... | 3.37 |
| Phe | 56G | CD1 | ... | Gly | 572E | CA | ... | 3.92 |
| Phe | 56G | CE1 | ... | Leu | 568E | C | ... | 3.88 |
|  |  |  | ... | Leu | 568E | O | ... | 3.24 |
|  |  |  | ... | Gly | 572E | CA | ... | 3.98 |
| Phe | 56G | CZ | ... | Leu | 568E | O | ... | 3.84 |
|  |  |  | ... | Thr | 569E | CG2 | ... | 3.92 |
|  |  |  | ... | Thr | 569E | CA | ... | 3.83 |
| Thr | 58G | CA | ... | Gln | 575E | OE1 | ... | 3.96 |
| Thr | 58G | CB | ... | Gln | 575E | OE1 | ... | 3.34 |

TABLE 7-continued

List of Contacts

| D5 | | | | 5-helix | | | | |
|---|---|---|---|---|---|---|---|---|
| Thr | 58G | OG1 | ... | Gln | 575E | OE1 | ... | 2.86*** |
|  |  |  | ... | Gln | 575E | CD | ... | 3.66 |
|  |  |  | ... | Gly | 572E | O | ... | 3.60* |
|  |  |  | ... | Gln | 575E | CB | ... | 3.01 |
|  |  |  | ... | Gln | 575E | CG | ... | 3.83 |
| Thr | 58G | CG2 | ... | Gly | 572E | CA | ... | 3.99 |
|  |  |  | ... | Gln | 575E | OE1 | ... | 2.83 |
| Thr | 58G | C | ... | Gln | 575E | OE1 | ... | 3.32 |
| Thr | 58G | O | ... | Gln | 575E | OE1 | ... | 3.34* |
| Ala | 59G | N | ... | Gln | 575E | OE1 | ... | 3.49* |
|  |  |  | ... | Arg | 579E | NH2 | ... | 3.00*** |
| Ala | 59G | CA | ... | Gln | 575E | OE1 | ... | 3.76 |
|  |  |  | ... | Arg | 579E | NH2 | ... | 3.45 |
| Ala | 59G | CB | ... | Arg | 579E | NH2 | ... | 3.76 |
| Ala | 59G | C | ... | Arg | 579E | NH2 | ... | 3.28 |
| Ala | 59G | O | ... | Arg | 579E | NH1 | ... | 3.92* |
|  |  |  | ... | Arg | 579E | CZ | ... | 3.44 |
|  |  |  | ... | Arg | 579E | NH2 | ... | 2.52*** |
|  |  |  | ... | Gln | 575E | CB | ... | 3.89 |
| Asn | 60G | N | ... | Gln | 575E | NE2 | ... | 3.98* |
| Asn | 60G | CB | ... | Gln | 575E | NE2 | ... | 3.90 |
| Asn | 60G | OD1 | ... | Ala | 578E | CB | ... | 3.94 |
| HCDR1 | | | | N-peptide2 | | | | |
| Ser | 32G | CB | ... | His | 564E | CE1 | ... | 3.59 |
| Ser | 32G | C | ... | His | 564E | CE1 | ... | 3.81 |
|  |  |  | ... | Leu | 568E | CD2 | ... | 3.68 |
| Ser | 32G | O | ... | His | 564E | ND1 | ... | 3.65* |
|  |  |  | ... | His | 564E | CE1 | ... | 2.85 |
|  |  |  | ... | His | 564E | NE2 | ... | 3.82* |
|  |  |  | ... | Leu | 568E | CD1 | ... | 3.80 |
|  |  |  | ... | Leu | 568E | CD2 | ... | 3.61 |
| Tyr | 33G | CE1 | ... | His | 564E | NE2 | ... | 3.49 |
| Tyr | 33G | CZ | ... | His | 564E | NE2 | ... | 3.75 |
| Tyr | 33G | OH | ... | His | 564E | NE2 | ... | 3.95* |
| HCDR3 | | | | N-peptide2 | | | | |
| Asp | 100G | CB | ... | Trp | 571E | CZ3 | ... | 3.87 |
|  |  |  | ... | Trp | 571E | CH2 | ... | 3.94 |
| Asp | 100G | O | ... | Trp | 571E | CZ3 | ... | 3.81 |
| Asn | 101G | ND2 | ... | His | 564E | CD2 | ... | 3.84 |
|  |  |  | ... | His | 564E | NE2 | ... | 3.71* |
| Asn | 101G | C | ... | Trp | 571E | CH2 | ... | 3.77 |
| Asn | 101G | O | ... | Trp | 571E | CH2 | ... | 3.97 |
| Pro | 102G | N | ... | Trp | 571E | CZ3 | ... | 3.86 |
|  |  |  | ... | Trp | 571E | CH2 | ... | 3.46 |
| Pro | 102G | CD | ... | Trp | 571E | CZ3 | ... | 3.93 |
|  |  |  | ... | His | 564E | CE1 | ... | 4.00 |
|  |  |  | ... | His | 564E | NE2 | ... | 3.85 |
| Pro | 102G | CA | ... | Trp | 571E | CZ3 | ... | 3.93 |
|  |  |  | ... | Trp | 571E | CZ2 | ... | 3.83 |
|  |  |  | ... | Trp | 571E | CH2 | ... | 3.40 |
| Pro | 102G | CB | ... | Trp | 571E | CZ3 | ... | 3.88 |
|  |  |  | ... | Trp | 571E | CH2 | ... | 3.87 |
|  |  |  | ... | His | 564E | O | ... | 3.55 |
|  |  |  | ... | Gln | 567E | CG | ... | 3.96 |
| Pro | 102G | CG | ... | His | 564E | CG | ... | 3.96 |
|  |  |  | ... | His | 564E | CD2 | ... | 3.86 |
|  |  |  | ... | His | 564E | ND1 | ... | 3.64 |
|  |  |  | ... | His | 564E | CE1 | ... | 3.35 |
|  |  |  | ... | His | 564E | NE2 | ... | 3.48 |
|  |  |  | ... | His | 564E | O | ... | 3.56 |
|  |  |  | ... | Leu | 568E | CD1 | ... | 3.91 |
| Pro | 102G | O | ... | Gln | 567E | CB | ... | 3.76 |
|  |  |  | ... | Gln | 567E | CG | ... | 3.35 |
| Thr | 103G | CB | ... | His | 564E | CD2 | ... | 3.74 |
| Thr | 103G | OG1 | ... | His | 564E | CB | ... | 3.46 |
|  |  |  | ... | His | 564E | CG | ... | 3.29 |
|  |  |  | ... | His | 564E | CD2 | ... | 2.64 |
|  |  |  | ... | His | 564E | NE2 | ... | 3.80* |
| Leu | 105G | CD1 | ... | Gln | 567E | CG | ... | 3.98 |
| LCDR3 | | | | N-peptide2 | | | | |
| Ser | 92F | C | ... | Lys | 574E | NZ | ... | 3.96 |
| Ser | 92F | O | ... | Lys | 574E | NZ | ... | 2.73*** |

TABLE 7-continued

List of Contacts

| D5 | | | | 5-helix | | | |
|---|---|---|---|---|---|---|---|
| Asn | 93F | OD1 | ... | Lys | 574E | NZ | ... | 3.70* |
| | | | ... | Lys | 574E | CD | ... | 3.59 |
| Tyr | 94F | CE1 | ... | Trp | 571E | O | ... | 3.86 |
| | | | ... | Gln | 575E | CG | ... | 3.87 |
| Tyr | 94F | CD2 | ... | Gln | 575E | NE2 | ... | 3.88 |
| Tyr | 94F | CE2 | ... | Gln | 575E | NE2 | ... | 3.31 |
| Tyr | 94F | CZ | ... | Gln | 575E | NE2 | ... | 3.47 |
| Tyr | 94F | OH | ... | Trp | 571E | CB | ... | 3.52 |
| | | | ... | Trp | 571E | CG | ... | 3.42 |
| | | | ... | Trp | 571E | CD2 | ... | 3.57 |
| | | | ... | Trp | 571E | CE3 | ... | 3.90 |
| | | | ... | Gln | 575E | NE2 | ... | 3.68* |
| | | | ... | Trp | 571E | CD1 | ... | 4.00 |

| LCDR1 | | | | C-peptide | | | |
|---|---|---|---|---|---|---|---|
| Tyr | 30F | CE1 | ... | Asn | 636D | OD1 | ... | 3.97 |
| | | | ... | Asn | 636D | CG | ... | 3.67 |
| | | | ... | Asn | 636D | ND2 | ... | 3.74 |
| Tyr | 30F | CE2 | ... | Asn | 636D | CB | ... | 3.63 |
| Tyr | 30F | CZ | ... | Asn | 636D | CB | ... | 3.61 |
| | | | ... | Asn | 636D | CG | ... | 3.72 |
| | | | ... | Asn | 636D | ND2 | ... | 3.80 |
| Tyr | 30F | OH | ... | Asn | 636D | CB | ... | 3.88 |
| | | | ... | Asn | 636D | CG | ... | 4.00 |
| | | | ... | Asn | 636D | ND2 | ... | 3.67* |
| Trp | 32F | CE2 | ... | Asn | 636D | OD1 | ... | 3.72 |

TABLE 7-continued

List of Contacts

| D5 | | | | 5-helix | | | |
|---|---|---|---|---|---|---|---|
| Trp | 32F | CD1 | ... | Asn | 636D | OD1 | ... | 3.46 |
| Trp | 32F | NE1 | ... | Asn | 636D | OD1 | ... | 2.63*** |
| | | | ... | Asn | 636D | CG | ... | 3.74 |
| Trp | 32F | CZ3 | ... | His | 643D | ND1 | ... | 3.78 |
| | | | ... | His | 643D | CE1 | ... | 3.65 |
| Trp | 32F | CH2 | ... | His | 643D | ND1 | ... | 3.66 |
| | | | ... | His | 643D | CE1 | ... | 3.57 |

| LCDR2 | | | | C-peptide | | | |
|---|---|---|---|---|---|---|---|
| Lys | 50F | CD | ... | His | 643D | ND1 | ... | 3.77 |
| | | | ... | His | 643D | CE1 | ... | 3.81 |
| Lys | 50F | CE | ... | His | 643D | ND1 | ... | 3.91 |
| | | | ... | His | 643D | CE1 | ... | 3.53 |
| Lys | 50F | NZ | ... | His | 643D | NE2 | ... | 3.31* |
| | | | ... | His | 643D | CG | ... | 3.77 |
| | | | ... | His | 643D | ND1 | ... | 3.52* |
| | | | ... | His | 643D | CE1 | ... | 3.24 |
| | | | ... | His | 643D | CD2 | ... | 3.64 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

---

What is claimed is:

1. An isolated HIV monoclonal antibody comprising an antibody binding portion that interacts with a conformational epitope within a groove of adjacent coils of a trimeric pre-hairpin intermediate structure of the heptad repeat 1 (HR1) region of the ectodomain of gp41, wherein said conformational epitope comprises amino acids Leu568, Trp571 and Lys574 that occupy one or the other of the adjacent coils within the trimeric pre-hairpin structure and wherein said antibody inhibits HIV infection of a target cell in vitro, wherein said antibody comprises a heavy chain variable ($V_H$) region and a light chain variable ($V_L$) region, wherein said $V_H$ region and said $V_L$ region each comprise three complementarity determining regions (CDR) and four framework (FW) regions arranged from the $NH_2$ terminus to the COOH terminus as follows: FW1, CDR1, FW2, CDR2, FW3, CDR3, FW4, and wherein:
- (a) said $V_H$ CDR1 comprises amino acids 31-35 of SEQ ID NO:4;
- (b) said $V_H$ CDR2 comprises amino acids 50-66 of SEQ ID NO:4;
- (c) said $V_H$ CDR3 comprises amino acids 99-108 of SEQ ID NO:4;
- (d) said $V_L$ CDR1 comprises amino acids 31-35 of SEQ ID NO:6;
- (e) said $V_L$ CDR2 comprises amino acids 50-56 of SEQ ID NO:6; and,
- (f) said $V_L$ CDR3 comprises amino acids 89-97 of SEQ ID NO:6.

2. The antibody of claim 1 comprising a heavy chain variable ($V_H$) region which comprises SEQ ID NO:4 and a light chain variable ($V_L$) region which comprises SEQ ID NO:6.

3. The antibody of claim 2 which is a scFv.

4. The antibody of claim 2 which is an immunoglobulin G (IgG).

5. An isolated HIV monoclonal antibody comprising an antibody binding portion that interacts with a conformational epitope within a groove of adjacent coils of a trimeric pre-hairpin intermediate structure of the heptad repeat 1 (HR1) region of the ectodomain of gp41, wherein said conformational epitope comprises amino acids Leu568, Trp571 and Lys574 that occupy one or the other of the adjacent coils within the trimeric pre-hairpin structure and wherein said antibody inhibits HIV infection of a target cell in vitro, wherein said antibody comprises a heavy chain variable ($V_H$) region and a light chain variable ($V_L$) region, wherein said $V_H$ region and said $V_L$ region each comprise three complementarity determining regions (CDR) and four framework (FW) regions arranged from the $NH_2$ terminus to the COOH terminus as follows: FW1, CDR1, FW2, CDR2, FW3, CDR3, FW4, and wherein:
- (a) said VH CDR1 comprises amino acids 31-35 of SEQ ID NO:10;
- (b) said $V_H$ CDR2 comprises amino acids 50-66 of SEQ ID NO:10;
- (c) said $V_H$ CDR3 comprises amino acids 99-108 of SEQ ID NO:10;
- (e) said $V_L$ CDR1 comprises amino acids 31-35 of SEQ ID NO:12;
- (e) said $V_L$ CDR2 comprises amino acids 50-56 of SEQ ID NO:12; and,
- (f) said $V_L$ CDR3 comprises amino acids 89-97 of SEQ ID NO:12.

6. The antibody of claim 5 comprising a heavy chain variable ($V_H$) region which comprises SEQ ID NO:10 and a light chain variable ($V_L$) region which comprises SEQ ID NO:12.

7. The antibody of claim 6 which is a scFv.

8. The antibody of claim 6 which is an immunoglobulin G (IgG).

9. An isolated HIV monoclonal antibody comprising an antibody binding portion that interacts with a conformational epitope within a groove of adjacent coils of a trimeric pre-hairpin intermediate structure of the heptad repeat 1 (HR1) region of the ectodomain of gp41, wherein said conformational epitope comprises amino acids Leu568, Trp571 and Lys574 that occupy one or the other of the adjacent coils within the trimeric pre-hairpin structure and wherein said antibody inhibits HIV infection of a target cell in vitro, wherein said antibody comprises a heavy chain variable ($V_H$) region and a light chain variable ($V_L$) region, wherein the heavy chain variable ($V_H$) region comprises SEQ ID NO:4 or SEQ ID NO:10.

10. The antibody of claim 9, wherein the heavy chain variable ($V_H$) region comprises SEQ ID NO:4.

11. The antibody of claim 9, wherein the heavy chain variable ($V_H$) region comprises SEQ ID NO:10.

* * * * *

SEQUENCE LISTING

```
<160> NUMBER OF SEQ ID NOS: 37

<210> SEQ ID NO 1
<211> LENGTH: 723
<212> TYPE: DNA
<213> ORGANISM: Homo sapien
<220> FEATURE:
<221> NAME/KEY: CDS
<222> LOCATION: (1)...(723)

<400> SEQUENCE: 1 cag gtg cag ctg gtg cag tct ggg gct gag gtg agg aag cct ggg gcc        48
Gln Val Gln Leu Val Gln Ser Gly Ala Glu Val Arg Lys Pro Gly Ala
1               5                  10                  15 tca gtg aag gtc tcc tgc aag gct tct gga gac acc ttc agc agc tat       96
Ser Val Lys Val Ser Cys Lys Ala Ser Gly Asp Thr Phe Ser Ser Tyr
            20                  25                  30 gct atc agc tgg gtg cga cag gcc cct gga caa ggg ctt gag tgg atg      144
Ala Ile Ser Trp Val Arg Gln Ala Pro Gly Gln Gly Leu Glu Trp Met
        35                  40                  45 gga ggg atc atc cct att ttt ggt aca gca aac tac gca cag aag ttc      192
Gly Gly Ile Ile Pro Ile Phe Gly Thr Ala Asn Tyr Ala Gln Lys Phe
    50                  55                  60 cag ggc aga gtc acg att acc gcg gac gaa tcc acg agt aca gcc tac      240
Gln Gly Arg Val Thr Ile Thr Ala Asp Glu Ser Thr Ser Thr Ala Tyr
65                  70                  75                  80 atg gag ctg agc agc ctg aga tct gaa gac acg gcc att tat tac tgc      288
Met Glu Leu Ser Ser Leu Arg Ser Glu Asp Thr Ala Ile Tyr Tyr Cys
                85                  90                  95 gcg aga gat aac ccg aca cta ctc ggc tct gac tac tgg ggc aag gga      336
Ala Arg Asp Asn Pro Thr Leu Leu Gly Ser Asp Tyr Trp Gly Lys Gly
            100                 105                 110
```

```
acc ctg gtc acc gtc tcg agt ggt gga ggc ggt tca ggc gga ggt ggc      384
Thr Leu Val Thr Val Ser Ser Gly Gly Gly Gly Ser Gly Gly Gly Gly
        115                 120                 125 agc ggc ggt ggc gga tcg gac atc cag atg acc cag tct cct tcc acc      432
Ser Gly Gly Gly Gly Ser Asp Ile Gln Met Thr Gln Ser Pro Ser Thr
    130                 135                 140 ctg tct gca tct att gga gac aga gtc acc atc acc tgc cgg gcc agt      480
Leu Ser Ala Ser Ile Gly Asp Arg Val Thr Ile Thr Cys Arg Ala Ser
145                 150                 155                 160 gag ggt att tat cac tgg ttg gcc tgg tat cag cag aag cca ggg aaa      528
Glu Gly Ile Tyr His Trp Leu Ala Trp Tyr Gln Gln Lys Pro Gly Lys
                165                 170                 175 gcc cct aaa ctc ctg atc tat aag gcc tct agt tta gcc agt ggg gcc      576
Ala Pro Lys Leu Leu Ile Tyr Lys Ala Ser Ser Leu Ala Ser Gly Ala
            180                 185                 190 cca tca agg ttc agc ggc agt gga tct ggg aca gat ttc act ctc acc      624
Pro Ser Arg Phe Ser Gly Ser Gly Ser Gly Thr Asp Phe Thr Leu Thr
        195                 200                 205 atc agc agc ctg cag cct gat gat ttt gca act tat tac tgc caa caa      672
Ile Ser Ser Leu Gln Pro Asp Asp Phe Ala Thr Tyr Tyr Cys Gln Gln
    210                 215                 220 tat agt aat tat ccg ctc act ttc ggc gga ggg acc aag ctg gag atc      720
Tyr Ser Asn Tyr Pro Leu Thr Phe Gly Gly Gly Thr Lys Leu Glu Ile
225                 230                 235                 240 aaa                                                                   723
Lys

<210> SEQ ID NO 2
<211> LENGTH: 241
<212> TYPE: PRT
<213> ORGANISM: Homo sapien

<400> SEQUENCE: 2

Gln Val Gln Leu Val Gln Ser Gly Ala Glu Val Arg Lys Pro Gly Ala
 1               5                  10                  15

Ser Val Lys Val Ser Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Asn Pro Thr Leu Leu Gly Ser Asp Tyr Trp Gly Lys Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Thr
    130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190
```

```
Pro Ser Arg Phe Ser Gly Ser Gly Ser Gly Thr Asp Phe Thr Leu Thr
        195                 200                 205

Ile Ser Ser Leu Gln Pro Asp Asp Phe Ala Thr Tyr Tyr Cys Gln Gln
        210                 215                 220

Tyr Ser Asn Tyr Pro Leu Thr Phe Gly Gly Gly Thr Lys Leu Glu Ile
225                 230                 235                 240

Lys

<210> SEQ ID NO 3
<211> LENGTH: 357
<212> TYPE: DNA
<213> ORGANISM: Homo sapien
<220> FEATURE:
<221> NAME/KEY: CDS
<222> LOCATION: (1)...(357)

<400> SEQUENCE: 3 cag gtg cag ctg gtg cag tct ggg gct gag gtg agg aag cct ggg gcc    48
Gln Val Gln Leu Val Gln Ser Gly Ala Glu Val Arg Lys Pro Gly Ala
 1               5                  10                  15 tca gtg aag gtc tcc tgc aag gct tct gga gac acc ttc agc agc tat    96
Ser Val Lys Val Ser Cys Lys Ala Ser Gly Asp Thr Phe Ser Ser Tyr
            20                  25                  30 gct atc agc tgg gtg cga cag gcc cct gga caa ggg ctt gag tgg atg   144
Ala Ile Ser Trp Val Arg Gln Ala Pro Gly Gln Gly Leu Glu Trp Met
        35                  40                  45 gga ggg atc atc cct att ttt ggt aca gca aac tac gca cag aag ttc   192
Gly Gly Ile Ile Pro Ile Phe Gly Thr Ala Asn Tyr Ala Gln Lys Phe
    50                  55                  60 cag ggc aga gtc acg att acc gcg gac gaa tcc acg agt aca gcc tac   240
Gln Gly Arg Val Thr Ile Thr Ala Asp Glu Ser Thr Ser Thr Ala Tyr
65                  70                  75                  80 atg gag ctg agc agc ctg aga tct gaa gac acg gcc att tat tac tgc   288
Met Glu Leu Ser Ser Leu Arg Ser Glu Asp Thr Ala Ile Tyr Tyr Cys
                85                  90                  95 gcg aga gat aac ccg aca cta ctc ggc tct gac tac tgg ggc aag gga   336
Ala Arg Asp Asn Pro Thr Leu Leu Gly Ser Asp Tyr Trp Gly Lys Gly
            100                 105                 110 acc ctg gtc acc gtc tcg agt                                       357
Thr Leu Val Thr Val Ser Ser
        115

<210> SEQ ID NO 4
<211> LENGTH: 119
<212> TYPE: PRT
<213> ORGANISM: Homo sapien

<400> SEQUENCE: 4

Gln Val Gln Leu Val Gln Ser Gly Ala Glu Val Arg Lys Pro Gly Ala
 1               5                  10                  15

Ser Val Lys Val Ser Cys Lys Ala Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Ile Tyr Tyr Cys
                85                  90                  95
```

Ala Arg Asp Asn Pro Thr Leu Leu Gly Ser Asp Tyr Trp Gly Lys Gly
                100                 105                 110

Thr Leu Val Thr Val Ser Ser
        115

<210> SEQ ID NO 5
<211> LENGTH: 321
<212> TYPE: DNA
<213> ORGANISM: Homo sapien
<220> FEATURE:
<221> NAME/KEY: CDS
<222> LOCATION: (1)...(321)

<400> SEQUENCE: 5 gac atc cag atg acc cag tct cct tcc acc ctg tct gca tct att gga     48
Asp Ile Gln Met Thr Gln Ser Pro Ser Thr Leu Ser Ala Ser Ile Gly
 1               5                  10                  15 gac aga gtc acc atc acc tgc cgg gcc agt gag ggt att tat cac tgg     96
Asp Arg Val Thr Ile Thr Cys Arg Ala Ser Glu Gly Ile Tyr His Trp
            20                  25                  30 ttg gcc tgg tat cag cag aag cca ggg aaa gcc cct aaa ctc ctg atc    144
Leu Ala Trp Tyr Gln Gln Lys Pro Gly Lys Ala Pro Lys Leu Leu Ile
        35                  40                  45 tat aag gcc tct agt tta gcc agt ggg gcc cca tca agg ttc agc ggc    192
Tyr Lys Ala Ser Ser Leu Ala Ser Gly Ala Pro Ser Arg Phe Ser Gly
    50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
65                  70                  75                  80 gat gat ttt gca act tat tac tgc caa caa tat agt aat tat ccg ctc    288
Asp Asp Phe Ala Thr Tyr Tyr Cys Gln Gln Tyr Ser Asn Tyr Pro Leu
                85                  90                  95 act ttc ggc gga ggg acc aag ctg gag atc aaa                        321
Thr Phe Gly Gly Gly Thr Lys Leu Glu Ile Lys
            100                 105

<210> SEQ ID NO 6
<211> LENGTH: 107
<212> TYPE: PRT
<213> ORGANISM: Homo sapien

<400> SEQUENCE: 6

Asp Ile Gln Met Thr Gln Ser Pro Ser Thr Leu Ser Ala Ser Ile Gly
 1               5                  10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys
            100                 105

<210> SEQ ID NO 7
<211> LENGTH: 723
<212> TYPE: DNA

<210> SEQ ID NO 7
<211> LENGTH: 723
<212> TYPE: DNA
<213> ORGANISM: Homo sapien
<220> FEATURE:
<221> NAME/KEY: CDS
<222> LOCATION: (1)...(723)

<400> SEQUENCE: 7

| cag | gtg | cag | ctg | gtg | caa | tct | ggg | gct | gag | gtg | aag | aag | cct | ggg | tcc | 48 |
| Gln | Val | Gln | Leu | Val | Gln | Ser | Gly | Ala | Glu | Val | Lys | Lys | Pro | Gly | Ser | |
| 1   |     |     |     | 5   |     |     |     |     | 10  |     |     |     |     | 15  |     | |

| tcg | gtg | aag | gtc | tcc | tgc | aag | gct | tct | gga | ggc | acc | ttc | agc | agc | tat | 96 |
| Ser | Val | Lys | Val | Ser | Cys | Lys | Ala | Ser | Gly | Gly | Thr | Phe | Ser | Ser | Tyr | |
|     |     |     | 20  |     |     |     |     | 25  |     |     |     |     | 30  |     |     | |

| gct | atc | agc | tgg | gtg | cga | cag | gcc | cct | gga | caa | ggg | ctt | gag | tgg | atg | 144 |
| Ala | Ile | Ser | Trp | Val | Arg | Gln | Ala | Pro | Gly | Gln | Gly | Leu | Glu | Trp | Met | |
|     | 35  |     |     |     |     | 40  |     |     |     |     | 45  |     |     |     |     | |

| gga | ggg | atc | atc | cct | ctc | ttt | gat | aca | tca | aac | tac | gca | cag | aac | ttc | 192 |
| Gly | Gly | Ile | Ile | Pro | Leu | Phe | Asp | Thr | Ser | Asn | Tyr | Ala | Gln | Asn | Phe | |
| 50  |     |     |     |     | 55  |     |     |     |     | 60  |     |     |     |     |     | |

| cag | ggc | aga | atc | acg | ata | act | gcg | gac | aaa | tcc | acg | agt | aca | gcc | tac | 240 |
| Gln | Gly | Arg | Ile | Thr | Ile | Thr | Ala | Asp | Lys | Ser | Thr | Ser | Thr | Ala | Tyr | |
| 65  |     |     |     | 70  |     |     |     |     | 75  |     |     |     |     | 80  |     | |

| atg | gaa | ctg | agc | agc | ctg | aga | ttt | gag | gac | acg | gcc | att | tat | tac | tgt | 288 |
| Met | Glu | Leu | Ser | Ser | Leu | Arg | Phe | Glu | Asp | Thr | Ala | Ile | Tyr | Tyr | Cys | |
|     |     |     |     | 85  |     |     |     |     | 90  |     |     |     |     | 95  |     | |

| gcg | aga | gat | aac | cct | tta | ctt | ctc | gct | atg | gat | gtc | tgg | ggg | aaa | ggg | 336 |
| Ala | Arg | Asp | Asn | Pro | Leu | Leu | Leu | Ala | Met | Asp | Val | Trp | Gly | Lys | Gly | |
|     |     |     | 100 |     |     |     |     | 105 |     |     |     |     | 110 |     |     | |

| acc | acg | gtc | acc | gtc | tcg | agt | ggt | gga | ggc | ggt | tca | ggc | gga | ggt | ggc | 384 |
| Thr | Thr | Val | Thr | Val | Ser | Ser | Gly | Gly | Gly | Gly | Ser | Gly | Gly | Gly | Gly | |
|     |     | 115 |     |     |     |     | 120 |     |     |     |     | 125 |     |     |     | |

| agc | ggc | ggt | ggc | gga | tcg | gac | atc | cag | atg | acc | cag | tct | cct | tcc | acc | 432 |
| Ser | Gly | Gly | Gly | Gly | Ser | Asp | Ile | Gln | Met | Thr | Gln | Ser | Pro | Ser | Thr | |
|     | 130 |     |     |     |     | 135 |     |     |     |     | 140 |     |     |     |     | |

| ctg | tct | gca | tct | att | gga | gac | aga | gtc | acc | atc | acc | tgc | cgg | gcc | agt | 480 |
| Leu | Ser | Ala | Ser | Ile | Gly | Asp | Arg | Val | Thr | Ile | Thr | Cys | Arg | Ala | Ser | |
| 145 |     |     |     |     | 150 |     |     |     |     | 155 |     |     |     |     | 160 | |

| gag | ggt | att | tat | cac | tgg | ttg | gcc | tgg | tat | cag | cag | aag | cca | ggg | aaa | 528 |
| Glu | Gly | Ile | Tyr | His | Trp | Leu | Ala | Trp | Tyr | Gln | Gln | Lys | Pro | Gly | Lys | |
|     |     |     |     | 165 |     |     |     |     | 170 |     |     |     |     | 175 |     | |

| gcc | cct | aaa | ctc | ctg | atc | tat | aag | gcc | tct | agt | tta | gcc | agt | ggg | gcc | 576 |
| Ala | Pro | Lys | Leu | Leu | Ile | Tyr | Lys | Ala | Ser | Ser | Leu | Ala | Ser | Gly | Ala | |
|     |     |     | 180 |     |     |     |     | 185 |     |     |     |     | 190 |     |     | |

| cca | tca | agg | ttc | agc | ggc | agt | gga | tct | ggg | aca | gat | ttc | act | ctc | acc | 624 |
| Pro | Ser | Arg | Phe | Ser | Gly | Ser | Gly | Ser | Gly | Thr | Asp | Phe | Thr | Leu | Thr | |
|     |     | 195 |     |     |     |     | 200 |     |     |     |     | 205 |     |     |     | |

| atc | agc | agc | ctg | cag | cct | gat | gat | ttt | gca | act | tat | tac | tgc | caa | caa | 672 |
| Ile | Ser | Ser | Leu | Gln | Pro | Asp | Asp | Phe | Ala | Thr | Tyr | Tyr | Cys | Gln | Gln | |
|     | 210 |     |     |     |     | 215 |     |     |     |     | 220 |     |     |     |     | |

| tat | agt | aat | tat | ccg | ctc | act | ttc | ggc | gga | ggg | acc | aag | ctg | gag | atc | 720 |
| Tyr | Ser | Asn | Tyr | Pro | Leu | Thr | Phe | Gly | Gly | Gly | Thr | Lys | Leu | Glu | Ile | |
| 225 |     |     |     | 230 |     |     |     |     | 235 |     |     |     |     | 240 |     | |

| aaa | | | | | | | | | | | | | | | | 723 |
| Lys | | | | | | | | | | | | | | | | |

<210> SEQ ID NO 8
<211> LENGTH: 241
<212> TYPE: PRT
<213> ORGANISM: Homo sapien

<400> SEQUENCE: 8

Gln Val Gln Leu Val Gln Ser Gly Ala Glu Val Lys Lys Pro Gly Ser

```
                1               5                   10                  15
            Ser Val Lys Val Ser Cys Lys Ala Ser Gly Gly Thr Phe Ser Ser Tyr
                            20                  25                  30

Ala Ile Ser Trp Val Arg Gln Ala Pro Gly Gln Gly Leu Glu Trp Met
                        35                  40                  45

Gly Gly Ile Ile Pro Leu Phe Asp Thr Ser Asn Tyr Ala Gln Asn Phe
                    50                  55                  60

Gln Gly Arg Ile Thr Ile Thr Ala Asp Lys Ser Thr Ser Thr Ala Tyr
            65                  70                  75                  80

Met Glu Leu Ser Ser Leu Arg Phe Glu Asp Thr Ala Ile Tyr Tyr Cys
                            85                  90                  95

Ala Arg Asp Asn Pro Leu Leu Leu Ala Met Asp Val Trp Gly Lys Gly
                            100                 105                 110

Thr Thr Val Thr Val Ser Ser Gly Gly Gly Ser Gly Gly Gly Gly
                        115                 120                 125

Ser Gly Gly Gly Gly Ser Asp Ile Gln Met Thr Gln Ser Pro Ser Thr
                    130                 135                 140

Leu Ser Ala Ser Ile Gly Asp Arg Val Thr Ile Thr Cys Arg Ala Ser
            145                 150                 155                 160

Glu Gly Ile Tyr His Trp Leu Ala Trp Tyr Gln Gln Lys Pro Gly Lys
                            165                 170                 175

Ala Pro Lys Leu Leu Ile Tyr Lys Ala Ser Ser Leu Ala Ser Gly Ala
                        180                 185                 190

Pro Ser Arg Phe Ser Gly Ser Gly Ser Gly Thr Asp Phe Thr Leu Thr
                    195                 200                 205

Ile Ser Ser Leu Gln Pro Asp Asp Phe Ala Thr Tyr Tyr Cys Gln Gln
            210                 215                 220

Tyr Ser Asn Tyr Pro Leu Thr Phe Gly Gly Gly Thr Lys Leu Glu Ile
            225                 230                 235                 240

Lys
```

<210> SEQ ID NO 9
<211> LENGTH: 357
<212> TYPE: DNA
<213> ORGANISM: Homo sapien
<220> FEATURE:
<221> NAME/KEY: CDS
<222> LOCATION: (1)...(357)

<400> SEQUENCE: 9

```
cag gtg cag ctg gtg caa tct ggg gct gag gtg aag aag cct ggg tcc        48
Gln Val Gln Leu Val Gln Ser Gly Ala Glu Val Lys Lys Pro Gly Ser
1               5                   10                  15 tcg gtg aag gtc tcc tgc aag gct tct gga ggc acc ttc agc agc tat        96
Ser Val Lys Val Ser Cys Lys Ala Ser Gly Gly Thr Phe Ser Ser Tyr
            20                  25                  30 gct atc agc tgg gtg cga cag gcc cct gga caa ggg ctt gag tgg atg       144
Ala Ile Ser Trp Val Arg Gln Ala Pro Gly Gln Gly Leu Glu Trp Met
        35                  40                  45 gga ggg atc atc cct ctc ttt gat aca tca aac tac gca cag aac ttc       192
Gly Gly Ile Ile Pro Leu Phe Asp Thr Ser Asn Tyr Ala Gln Asn Phe
    50                  55                  60 cag ggc aga atc acg ata act gcg gac aaa tcc acg agt aca gcc tac       240
Gln Gly Arg Ile Thr Ile Thr Ala Asp Lys Ser Thr Ser Thr Ala Tyr
65                  70                  75                  80 atg gaa ctg agc agc ctg aga ttt gag gac acg gcc att tat tac tgt       288
Met Glu Leu Ser Ser Leu Arg Phe Glu Asp Thr Ala Ile Tyr Tyr Cys
```

```
                       85                  90                  95
gcg aga gat aac cct tta ctt ctc gct atg gat gtc tgg ggg aaa ggg            336
Ala Arg Asp Asn Pro Leu Leu Leu Ala Met Asp Val Trp Gly Lys Gly
            100                 105                 110 acc acg gtc acc gtc tcg agt                                                357
Thr Thr Val Thr Val Ser Ser
        115

<210> SEQ ID NO 10
<211> LENGTH: 119
<212> TYPE: PRT
<213> ORGANISM: Homo sapien

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Asp Thr Ser Asn Tyr Ala Gln Asn Phe
    50                  55                  60

Gln Gly Arg Ile Thr Ile Thr Ala Asp Lys Ser Thr Ser Thr Ala Tyr
65                  70                  75                  80

Met Glu Leu Ser Ser Leu Arg Phe Glu Asp Thr Ala Ile Tyr Tyr Cys
                85                  90                  95

Ala Arg Asp Asn Pro Leu Leu Leu Ala Met Asp Val Trp Gly Lys Gly
            100                 105                 110

Thr Thr Val Thr Val Ser Ser
        115

<210> SEQ ID NO 11
<211> LENGTH: 321
<212> TYPE: DNA
<213> ORGANISM: Homo sapien
<220> FEATURE:
<221> NAME/KEY: CDS
<222> LOCATION: (1)...(321)

<400> SEQUENCE: 11 gac atc cag atg acc cag tct cct tcc acc ctg tct gca tct att gga            48
Asp Ile Gln Met Thr Gln Ser Pro Ser Thr Leu Ser Ala Ser Ile Gly
1               5                   10                  15 gac aga gtc acc atc acc tgc cgg gcc agt gag ggt att tat cac tgg            96
Asp Arg Val Thr Ile Thr Cys Arg Ala Ser Glu Gly Ile Tyr His Trp
            20                  25                  30 ttg gcc tgg tat cag cag aag cca ggg aaa gcc cct aaa ctc ctg atc           144
Leu Ala Trp Tyr Gln Gln Lys Pro Gly Lys Ala Pro Lys Leu Leu Ile
        35                  40                  45 tat aag gcc tct agt tta gcc agt ggg gcc cca tca agg ttc agc ggc           192
Tyr Lys Ala Ser Ser Leu Ala Ser Gly Ala Pro Ser Arg Phe Ser Gly
    50                  55                  60 agt gga tct ggg aca gat ttc act ctc acc atc agc agc ctg cag cct           240
Ser Gly Ser Gly Thr Asp Phe Thr Leu Thr Ile Ser Ser Leu Gln Pro
65                  70                  75                  80 gat gat ttt gca act tat tac tgc caa caa tat agt aat tat ccg ctc           288
Asp Asp Phe Ala Thr Tyr Tyr Cys Gln Gln Tyr Ser Asn Tyr Pro Leu
                85                  90                  95 act ttc ggc gga ggg acc aag ctg gag atc aaa                               321
Thr Phe Gly Gly Gly Thr Lys Leu Glu Ile Lys
```

<210> SEQ ID NO 12
<211> LENGTH: 107
<212> TYPE: PRT
<213> ORGANISM: Homo sapien

<400> SEQUENCE: 12

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys
            100                 105

<210> SEQ ID NO 13
<211> LENGTH: 226
<212> TYPE: PRT
<213> ORGANISM: Artificial Sequence
<220> FEATURE:
<223> OTHER INFORMATION: synthetic peptide - 5-Helix

<400> SEQUENCE: 13

Met Gln Leu Leu Ser Gly Ile Val Gln Gln Gln Asn Asn Leu Leu Arg
1               5                   10                  15

Ala Ile Glu Ala Gln Gln His Leu Leu Gln Leu Thr Val Trp Gly Ile
            20                  25                  30

Lys Gln Leu Gln Ala Arg Ile Leu Ala Gly Gly Ser Gly Gly His Thr
        35                  40                  45

Thr Trp Met Glu Trp Asp Arg Glu Ile Asn Asn Tyr Thr Ser Leu Ile
    50                  55                  60

His Ser Leu Ile Glu Glu Ser Gln Asn Gln Gln Lys Asn Glu Gln
65                  70                  75                  80

Glu Leu Leu Glu Gly Ser Ser Gly Gly Gln Leu Leu Ser Gly Ile Val
                85                  90                  95

Gln Gln Gln Asn Asn Leu Leu Arg Ala Ile Glu Ala Gln Gln His Leu
                100                 105                 110

Leu Gln Leu Thr Val Trp Gly Ile Lys Gln Leu Gln Ala Arg Ile Leu
        115                 120                 125

Ala Gly Gly Ser Gly Gly His Thr Thr Trp Met Glu Trp Asp Arg Glu
    130                 135                 140

Ile Asn Asn Tyr Thr Ser Leu Ile His Ser Leu Ile Glu Glu Ser Gln
145                 150                 155                 160

Asn Gln Gln Glu Lys Asn Glu Gln Glu Leu Leu Glu Gly Ser Ser Gly
                165                 170                 175

Gly Gln Leu Leu Ser Gly Ile Val Gln Gln Gln Asn Asn Leu Leu Arg
            180                 185                 190

Ala Ile Glu Ala Gln Gln His Leu Leu Gln Leu Thr Val Trp Gly Ile
        195                 200                 205

```
Lys Gln Leu Gln Ala Arg Ile Leu Ala Gly Gly His His His His
    210                 215                 220

His Gly
225

<210> SEQ ID NO 14
<211> LENGTH: 62
<212> TYPE: PRT
<213> ORGANISM: Artificial Sequence
<220> FEATURE:
<223> OTHER INFORMATION: synthetic peptide - IZN36
<220> FEATURE:
<221> NAME/KEY: ACETYLATION
<222> LOCATION: (1)...(1)

<400> SEQUENCE: 14

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Ser Gly Ile Val Gln Gln
            20                  25                  30

Gln Asn Asn Leu Leu Arg Ala Ile Glu Ala Gln Gln His Leu Leu Gln
        35                  40                  45

Leu Thr Val Trp Gly Ile Lys Gln Leu Gln Ala Arg Ile Leu
    50                  55                  60

<210> SEQ ID NO 15
<211> LENGTH: 38
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (27)...(27)
<223> OTHER INFORMATION: s=(g/c)

<400> SEQUENCE: 15
ctctccacag gcgcgcactc ccaggtscag ctggtgca                             38

<210> SEQ ID NO 16
<211> LENGTH: 21
<212> TYPE: DNA
<213> ORGANISM: Artificial Sequence
<220> FEATURE:
<223> OTHER INFORMATION: oligonucleotide

<400> SEQUENCE: 16
accgccagag ccacctccgc c                                               21

<210> SEQ ID NO 17
<211> LENGTH: 40
<212> TYPE: DNA
<213> ORGANISM: Artificial Sequence
<220> FEATURE:
<223> OTHER INFORMATION: oligonucleotide

<400> SEQUENCE: 17
gatcgatggt gtgcactcgg acatccagat gacccagtct                           40

<210> SEQ ID NO 18
<211> LENGTH: 59
<212> TYPE: DNA
<213> ORGANISM: Artificial Sequence
<220> FEATURE:
<223> OTHER INFORMATION: oligonucleotide
```

<400> SEQUENCE: 18
ctattcctta attaagttag atctattcta ctcacgtttg atctccagct tgtccctcc      59

<210> SEQ ID NO 19
<211> LENGTH: 414
<212> TYPE: DNA
<213> ORGANISM: Homo sapien

<400> SEQUENCE: 19
ctctccacag gcgcgcactc ccaggtgcag ctggtgcagt ctggggctga ggtgaggaag      60
cctggggcct cagtgaaggt ctcctgcaag gcttctggag acaccttcag cagctatgct     120
atcagctggg tgcgacaggc ccctggacaa gggcttgagt ggatgggagg gatcatccct     180 attttttggta cagcaaacta cgcacagaag ttccagggca gagtcacgat taccgcggac    240
gaatccacga gtacagccta catggagctg agcagcctga gatctgaaga cacggccatt     300
tattactgcg cgagagataa cccgacacta ctcggctctg actactgggg caagggaacc     360
ctggtcaccg tctcgagtgg tggaggcggt tcaggcggag gtggctctgg cggt            414

<210> SEQ ID NO 20
<211> LENGTH: 376
<212> TYPE: DNA
<213> ORGANISM: Homo sapien

<400> SEQUENCE: 20
gatcgatggt gtgcactcgg acatccagat gacccagtct ccttccaccc tgtctgcatc      60
tattggagac agagtcacca tcacctgccg ggccagtgag ggtatttatc actggttggc     120
ctggtatcag cagaagccag ggaaagcccc taaactcctg atctataagg cctctagttt     180
agccagtggg gccccatcaa ggttcagcgg cagtggatct gggacagatt tcactctcac     240
catcagcagc ctgcagcctg atgattttgc aacttattac tgccaacaat atagtaatta    300
tccgctcact ttcggcggag ggaccaagct ggagatcaaa cgtgagtaga atagatctaa     360
cttaattaag gaatag                                                     376

<210> SEQ ID NO 21
<211> LENGTH: 19
<212> TYPE: DNA
<213> ORGANISM: Artificial Sequence
<220> FEATURE:
<223> OTHER INFORMATION: oligonucleotide

<400> SEQUENCE: 21
gcaggcttga ggtctggac                                                   19

<210> SEQ ID NO 22
<211> LENGTH: 18
<212> TYPE: DNA
<213> ORGANISM: Artificial Sequence
<220> FEATURE:
<223> OTHER INFORMATION: oligonucleotide

<400> SEQUENCE: 22 ccaggggaa gaccgatg                                                     18

<210> SEQ ID NO 23
<211> LENGTH: 33
<212> TYPE: DNA
<213> ORGANISM: Artificial Sequence
<220> FEATURE:

-continued

<223> OTHER INFORMATION: oligonucleotide

<400> SEQUENCE: 23
cttgaggtct ggacatatat atgggtgaca atg                              33

<210> SEQ ID NO 24
<211> LENGTH: 30
<212> TYPE: DNA
<213> ORGANISM: Artificial Sequence
<220> FEATURE:
<223> OTHER INFORMATION: oligonucleotide

<400> SEQUENCE: 24
tcctgggagt tacccgattg gagggcgtta                                  30

<210> SEQ ID NO 25
<211> LENGTH: 18
<212> TYPE: PRT
<213> ORGANISM: Artificial Sequence
<220> FEATURE:
<223> OTHER INFORMATION: synthetic peptide

<400> SEQUENCE: 25

Met Gly Trp Ser Cys Ile Ile Phe Leu Val Ala Thr Ala Thr Gly Ala
 1               5                  10                  15

His Ser

<210> SEQ ID NO 26
<211> LENGTH: 414
<212> TYPE: DNA
<213> ORGANISM: Homo sapien

<400> SEQUENCE: 26
ctctccacag gcgcgcactc ccaggtgcag ctggtgcaat ctggggctga ggtgaagaag     60
cctgggtcct cggtgaaggt ctcctgcaag gcttctggag gcaccttcag cagctatgct    120
atcagctggg tgcgacaggc ccctggacaa gggcttgagt ggatgggagg gatcatccct    180
ctctttgata tcatcaaacta cgcacagaac ttccagggca gaatcacgat aactgcggac    240
aaatccacga gtacagccta catggaactg agcagcctga gatttgagga cacggccatt    300
tattactgtg cgagagataa ccctttactt ctcgctatgg atgtctgggg gaaagggacc    360
acggtcaccg tctcgagtgg tggaggcggt tcaggcggag gtggctctgg cggt            414

<210> SEQ ID NO 27
<211> LENGTH: 376
<212> TYPE: DNA
<213> ORGANISM: Homo sapien

<400> SEQUENCE: 27
gatcgatggt gtgcactcgg acatccagat gacccagtct ccttccaccc tgtctgcatc     60
tattggagac agagtcacca tcacctgccg ggccagtgag ggtatttatc actggttggc    120
ctggtatcag cagaagccag ggaaagcccc taaactcctg atctataagg cctctagttt    180
agccagtggg gccccatcaa ggttcagcgg cagtggatct gggacagatt tcactctcac    240
catcagcagc ctgcagcctg atgattttgc aacttattac tgccaacaat atagtaatta    300
tccgctcact ttcggcggag ggaccaagct ggagatcaaa cgtgagtaga atagatctaa    360
cttaattaag gaatag                                                      376

<210> SEQ ID NO 28

<211> LENGTH: 24
<212> TYPE: DNA
<213> ORGANISM: Artificial Sequence
<220> FEATURE:
<223> OTHER INFORMATION: oligonucleotide

<400> SEQUENCE: 28
ggatccgaac aagccccaga agac                                          24

<210> SEQ ID NO 29
<211> LENGTH: 27
<212> TYPE: DNA
<213> ORGANISM: Artificial Sequence
<220> FEATURE:
<223> OTHER INFORMATION: oligonucleotide

<400> SEQUENCE: 29
gggctcgagt taggatctac tggctcc                                       27

<210> SEQ ID NO 30
<211> LENGTH: 21
<212> TYPE: DNA
<213> ORGANISM: Artificial Sequence
<220> FEATURE:
<223> OTHER INFORMATION: oligonucleotide

<400> SEQUENCE: 30
ggaagcttgg taccaccatg g                                             21

<210> SEQ ID NO 31
<211> LENGTH: 36
<212> TYPE: DNA
<213> ORGANISM: Artificial Sequence
<220> FEATURE:
<223> OTHER INFORMATION: oligonucleotide

<400> SEQUENCE: 31
tggggcttgt tcggatcccc aatgcttaat cagtga                             36

<210> SEQ ID NO 32
<211> LENGTH: 49
<212> TYPE: PRT
<213> ORGANISM: Artificial Sequence
<220> FEATURE:
<223> OTHER INFORMATION: synthetic peptide

<400> SEQUENCE: 32

Trp Met Glu Trp Asp Arg Glu Ile Asn Asn Tyr Thr Ser Ile Leu His
 1               5                  10                  15

Ser Leu Ile Glu Glu Ser Gln Asn Gln Gln Glu Lys Asn Glu Gln Glu
            20                  25                  30

Leu Leu Gly Gly Gly Tyr Pro Tyr Asp Val Pro Asp Tyr Ala Gly Pro
        35                  40                  45

Gly

<210> SEQ ID NO 33
<211> LENGTH: 37
<212> TYPE: PRT
<213> ORGANISM: HIV-1
<220> FEATURE:

<400> SEQUENCE: 33

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
                20                  25                  30

Ala Arg Ile Leu Ala
        35

<210> SEQ ID NO 34
<211> LENGTH: 37
<212> TYPE: PRT
<213> ORGANISM: HIV-1
<220> FEATURE:

<400> SEQUENCE: 34

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg Val Leu Ala
        35

<210> SEQ ID NO 35
<211> LENGTH: 37
<212> TYPE: PRT
<213> ORGANISM: HIV-1

<400> SEQUENCE: 35

Ser Gly Ile Val Gln Gln Gln Asn Asn Leu Leu Arg Ala Ile Glu Ala
1               5                   10                  15

Gln Gln His Met Leu Gln Leu Thr Val Trp Gly Ile Lys Gln Leu Gln
                20                  25                  30

Ala Arg Val Leu Ala
        35

<210> SEQ ID NO 36
<211> LENGTH: 37
<212> TYPE: PRT
<213> ORGANISM: HIV-1

<400> SEQUENCE: 36

Ser Gly Ile Val Gln Gln Gln Asn Asn Leu Leu Arg Ala Ile Glu Ala
1               5                   10                  15

Gln Gln His Met Leu Gln Leu Thr Val Trp Gly Ile Lys Gln Leu Gln
                20                  25                  30

Ala Arg Val Leu Ala
        35

<210> SEQ ID NO 37
<211> LENGTH: 37
<212> TYPE: PRT
<213> ORGANISM: HIV-1

<400> SEQUENCE: 37

Ser Asp Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
                20                  25                  30

Ala Arg Ile Leu Ala
        35